(12) United States Patent  (10) Patent No.: US 8,290,790 B1
Jackson et al.  (45) Date of Patent: *Oct. 16, 2012

(54) SYSTEMS AND METHODS FOR MANAGING AND/OR ADMINISTERING PRESCRIPTION BENEFITS

(75) Inventors: William J. Jackson, West Orange, NJ (US); Yehuda Ecksein, New Hempstead, NY (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 724 days.

This patent is subject to a terminal disclaimer.

(21) Appl. No.: 11/515,122

(22) Filed: Sep. 1, 2006

Related U.S. Application Data

(60) Provisional application No. 60/713,532, filed on Sep. 1, 2005.

(51) Int. Cl.
*G06Q 10/00* (2012.01)
(52) U.S. Cl. ..................... 705/3; 705/1; 705/2
(58) Field of Classification Search ........ 705/3
See application file for complete search history.

(56) References Cited

U.S. PATENT DOCUMENTS

| | | | |
|---|---|---|---|
| 5,544,086 A * | 8/1996 | Davis et al. ............... | 705/68 |
| 5,845,255 A * | 12/1998 | Mayaud ...................... | 705/3 |
| 6,283,761 B1 * | 9/2001 | Joao ........................... | 434/236 |
| 6,694,298 B1 | 2/2004 | Teagarden et al. | |
| 6,697,783 B1 | 2/2004 | Brinkman et al. | |
| 7,020,618 B1 | 3/2006 | Ward | |
| 7,155,397 B2 * | 12/2006 | Alexander et al. ......... | 705/2 |
| 2002/0103680 A1 * | 8/2002 | Newman .................... | 705/4 |
| 2002/0143582 A1 * | 10/2002 | Neuman et al. ............ | 705/3 |
| 2003/0225595 A1 | 12/2003 | Helmus et al. | |
| 2004/0006490 A1 * | 1/2004 | Gingrich et al. ........... | 705/2 |
| 2004/0019502 A1 * | 1/2004 | Leaman et al. ............. | 705/2 |
| 2005/0060197 A1 | 3/2005 | Mayaud | |

* cited by examiner

*Primary Examiner* — Hiep V Nguyen
(74) *Attorney, Agent, or Firm* — Husch Blackwell LLP

(57) ABSTRACT

Systems and methods for allowing a user (e.g., a benefits administrator) to maintain and modify a contract or a group for a prescription drug plan may be provided. In response to receiving a request to modify a contract or a group, a prescription benefits management application may retrieve data relating to the contract or group and allow the user to input information relating to the contract or group, input broker information, input billing information, select a pharmacy network, select pricing options for the prescription plan, create a customized prescription plan, input brand/generic difference overrides, etc. In some embodiments, the modifications and/or additions made to a contract or group may be transmitted to a pharmacist, thereby allowing the pharmacist to fill one or more prescriptions in real-time or upon updating the system (e.g., within 48 to 72 hours).

38 Claims, 53 Drawing Sheets

The Medco Client Website — *medco*

Contact Us | email Profile | Privacy | Terms of Use | Search | Logout

Welcome | Benefit Services | Library

- Search
- Clients
- Special Requests
- Communication Setup
- Drug Plans
- Report

| | Client Name | Contract # | Status | Effective Date |
|---|---|---|---|---|
| ○ | TestClient35 | 5935CONT | ACTIVE | 5/16/2005 |
| ○ | TestClient36 | 5936CONT | ACTIVE | 5/26/2005 |
| ○ | TestClient37 | 5937CONT | ACTIVE | 6/15/2005 |
| ○ | TestClient38 | 5938CONT | ACTIVE | 6/15/2005 |
| ○ | TestClient39 | 5939CONT | ACTIVE | 6/15/2005 |
| ○ | ArkadiyClient01 | ARKADIYC | ACTIVE | 6/15/2005 |
| ○ | Bill Test 2 | BILLUAT2 | ACTIVE | 5/10/2005 |
| ○ | | CONT2111 | ACTIVE | 5/1/2004 |
| ○ | InsulinClient | INSULIN1 | ACTIVE | 4/21/2005 |
| ○ | Effective Date Check | INSULIN3 | ACTIVE | 4/21/2005 |
| ○ | insulin5 | INSULIN5 | ACTIVE | 4/21/2005 |
| ○ | TestIssue1 | ISSUES12 | ACTIVE | 1/1/2006 |
| ○ | Janet's Client | JANCL001 | ACTIVE | 5/16/2005 |
| ○ | Judo World | JUDO2936 | ACTIVE | 5/1/2005 |
| ○ | Karate USA | KARUSA36 | ACTIVE | 4/15/2005 |
| ○ | HAPMA | NAPMA936 | ACTIVE | 4/22/2005 |
| ○ | PerformanceTestClient | PERFCONT | ACTIVE | 6/1/2005 |
| ○ | srini111 | SRINI111 | ACTIVE | 5/1/2005 |
| ○ | Tiger Schulmans | TIGKAR36 | ACTIVE | 5/1/2005 |
| ○ | Bill Test | TUAT2936 | ACTIVE | 5/6/2005 |

ADD CLIENT    ADD GROUP ← 1210    VIEW GROUP LIST

Figure 22 (DAW 2)

Figure 23 (DAW 1)

Figure 24 (Additional charge)

The Medco Client Website

3600

Client Information

Organization Name: 12935 | Carrier Name: GATEST | Client Name: User Guide | Group Name: USER TEST Group Information | Co-payments | Deductible | CAP | Out of Pocket | Drug Plan | General Benefits | Communications

Group Add

General Benefits: General Benefits

Special Request | Help

Under what circumstances will you allow a refill override?
- ○ No override
- ○ Override for therapy change
- ○ Override for therapy change and vacation supplies
- ⦿ Override for therapy change, vacation supplies, and lost medication

How are syringes covered if dispensed with insulin in Retail?
- ○ Separate co-payments will be charged for insulin and syringes
- ○ No co-payment is charged for syringes

How are syringes covered if dispensed with insulin in Mail?
- ○ Separate co-payments will be charged for insulin and syringes
- ○ No co-payment is charged for syringes

Do you want to provide coverage for allergy serum?
- ○ Yes
- ⦿ No

[BACK] [CANCEL]          [NEXT]

Sidebar
- Search
- Clients
- Groups
- Primary Information
- Pricing
- Co-payment
- Deductible
- CAP
- Out of Pocket
- Drug Plan
- General Benefits
- Communications
- Group Summary
- Special Requests
- Communication Setup
- Drug Plans
- Report

| Carrier Number | Contract Number | Group Number | Flow Indica | Confirm Date | Finalize Date | Turnaround Time | Custom Drugplan Indicat | Custom Drugplan Comp Date | Spec Rqst Indicat | Speci Rqst Compl Date |
|---|---|---|---|---|---|---|---|---|---|---|
| 6184 | DEMO1205 | DEMOGRP010606 | Add | 01/06/2006 | 01/06/2006 | 0 | true | 01/06/2006 | true | 01/06/2006 |
| 6184 | DEMO1205 | DEMOGRP010606 | Maintain | 01/06/2006 | 01/06/2006 | 0 | true | 01/06/2006 | true | 01/06/2006 |
| 6184 | TEST1201 | DRUGPLAN1208 | Add | 12/08/2005 | 12/08/2005 | 0 | true | 12/08/2005 | true | 12/08/2005 |
| 6184 | GF011606 | GENF011606 | Add | 01/16/2006 | 01/16/2006 | 0 | true | 01/16/2006 | true | 01/16/2006 |
| 6184 | HIGHTEST | HTEST010506 | Add | 01/03/2006 | 01/03/2006 | 0 | true | 01/03/2006 | true | 01/03/2006 |
| 6184 | QATEST14 | QATEST1214 | Add | 12/14/2005 | 12/14/2005 | 0 | true | 12/14/2005 | true | 12/14/2005 |
| 6184 | QATEST14 | QATEST1214 | Maintain | 12/14/2005 | 12/14/2005 | 0 | true | 12/14/2005 | true | 12/14/2005 |
| 6184 | TESTA106 | TESTAGAIN10606 | Add | 01/06/2006 | 01/06/2006 | 0 | true | 01/06/2006 | true | 01/06/2006 |
| 6184 | TESTHM12 | TESTHMRK1207 | Add | 12/07/2005 | 12/07/2005 | 0 | true | 12/07/2005 | true | 12/07/2005 |
| 6184 | TEST1201 | TESTRET1 | Add | 12/06/2005 | 12/06/2005 | 0 | true | 12/06/2005 | true | 12/06/2005 |
| 6184 | TEST1201 | TESTRET2 | Add | 12/06/2005 | 12/06/2005 | 0 | true | 12/06/2005 | true | 12/06/2005 |
| 6184 | TEST1201 | TESTRET3 | Add | 12/06/2005 | 12/06/2005 | 0 | true | 12/06/2005 | true | 12/06/2005 |
| 6184 | TEST0101 | TESTSUE0117 | Add | 01/17/2006 | 01/17/2006 | 0 | true | 01/17/2006 | true | 01/17/2006 |
| 6184 | TEST1201 | TEST120705 | Add | 12/07/2005 | 12/07/2005 | 0 | true | 12/07/2005 | true | 12/07/2005 |
| 6184 | GF011606 | 12345678 | Add | 01/23/2006 | 01/23/2006 | 0 | true | 01/23/2006 | true | 01/23/2006 |

SYSTEMS AND METHODS FOR MANAGING AND/OR ADMINISTERING PRESCRIPTION BENEFITS

CROSS REFERENCE TO RELATED APPLICATIONS

This application claims the benefit under 35 U.S.C. §119(e) of U.S. Patent Application No. 60/713,532, filed Sep. 1, 2005, which is hereby incorporated by reference herein in its entirety.

FIELD OF THE INVENTION

The present invention generally relates to systems and methods for managing, administering and/or sponsoring prescription drug coverage. More particularly, the present invention relates to systems and methods for managing, administering, sponsoring and/or maintaining prescription benefit and coverage information for one or more users.

BACKGROUND OF THE INVENTION

Employers often provide employees with various benefits upon commencement of employment. These benefits typically include a prescription drug plan, which varies depending on the particular healthcare provider selected by the employer. The specific coverage offered to an employee may depend on several factors, such as, for example, the particular coverage program negotiated by the employer, the medical coverage desired by the employee, the number of tiers in the prescription drug plan, the co-pay amounts, the drug coverage rules, the prescription medication available to the employee, the preferred drug lists associated with the prescription drug plan, the usage of mail order for certain prescriptions, etc. Certain events may also affect an employer's prescription drug plan, such as the introduction of generic drugs, the introduction of a new drug, the introduction of new drug benefits, or a shift in a drug from prescription to over-the-counter. For example, effective Jan. 1, 2006, the United States government implemented the Medicare Part D Prescription Drug Benefit plan.

Regardless of the coverage, the healthcare provider will place certain restrictions and/or limitations on the prescription medication available to the employee. These restrictions determine whether the healthcare provider will cover the cost of a prescription claim in full or in part. For example, the healthcare provider may cover the cost of a prescription claim in full, if the employee is willing to substitute a generic form of the prescribed medication in place of the brand name drug. In another example, the healthcare provider may subsidize the cost of the prescription to different degrees depending on, for example, if the employee prefers to use a brand name form of the prescribed medication.

Healthcare providers can face difficulties in managing coverage plans depending on various factors. For example, a healthcare provider may render services to a number of employers, where each employer offers coverage to multiple patients (e.g., employees, their domestic partners, their spouses, their children, their dependents, etc.). The number of patients generally varies based on the size of the employer and availability of alternative coverage plans (e.g., alternative healthcare providers). In the case of a large employer with few alternative coverage plans, the healthcare provider may be responsible for managing benefits of a great deal of patients. This situation is further complicated if the healthcare provider extends coverage plans to additional large employers.

When healthcare providers receive claims, each claim must be reviewed to ensure that they are supported by the patient's coverage plan. In the case of filling prescriptions, immediate approval or denial is required while the pharmacist prepares the prescription. It can be difficult to quickly approve or deny the prescription if the patient's prescription plan includes a large number of restrictions. Further complications arise when the patient requires specialized medication. It is possible to mistakenly support the prescription claim through the coverage plan if a restriction is overlooked. It is also possible to mistakenly deny the prescription claim if a restriction is misinterpreted.

For example, when the Medicare Part D Prescription Drug Benefit was implemented in January 2006, pharmacies discovered a number of problems. In some cases, pharmacies attempting to fill prescriptions from these Medicare patients discovered that these patients were not yet enrolled or registered in the computer systems under their new drug prescription plan. In other cases, pharmacies found that it was difficult to determine whether the prescriptions requested by these patients were covered by the new prescription plan. As a result, Medicare patients were not receiving the medication they required in a timely manner, or pharmacies were providing small dosages of the medication to those in a life-or-death situation and hoping that the government or healthcare providers would reimburse them at a later time. In response, many states have declared a public health emergency, where the state would provide short-term aid to pharmacies to assist in getting these prescriptions filled.

Prior art methods do not effectively manage and/or administer prescription benefit plans as in the present invention. For example, U.S. Pat. No. 6,694,298, entitled "Computer implemented patient medication review system and process for the managed care, health care and/or pharmacy industry," and assigned to the assignee of the present invention, relates to an interactive computer assisted method that reviews, and analyzes, one or more medications of a patient. The method includes the steps of pre-selecting patients to obtain a preliminary set of patients eligible for the method responsive to first predetermined criteria, and filtering the preliminary set of patients to identify and form a secondary set of patients having a greater likelihood of benefiting from the interactive computer assisted method. The method also includes the steps of enrolling a patient from the secondary set of patients, and communicating with the patient to obtain information to assist the user in determining whether therapy and/or medication issues are relevant. The method also includes the steps of preliminarily evaluating whether the therapy and medication issues are relevant responsive to the information, and communicating to a physician same. The method also includes the steps of determining whether the therapy and/or medication issues are relevant, and suggesting therapy changes, medication changes, or no changes for the patient. Accordingly, while this patent provides excellent review of patient medications, it is not directly related to managing and/or administrating a prescription benefit plan or program.

U.S. Pat. No. 6,697,783, entitled "Computer implemented medical integrated decision support system," also assigned to the assignee of the present invention, relates to a software-based, integrated member decision support system that provides corporations, insurance carriers, health maintenance organizations, physicians, physician groups, or other clients to efficiently provide medical, pharmaceutical, and health benefit advice and information for an enrolled population. The system contains one or more databases which include member profiles, clinical information and guidelines, pharmaceutical information and guidelines, health benefit information, and optional additional information. A caller establishes communication with the system, which directs the caller to an operator who provides the caller with medical, pharmaceutical, and/or health benefit advice based on an inquiry from the caller and the information stored on the system. The system may automatically alert the caller or the operator of important medical or pharmaceutical information. At the conclusion of the call, the system or the system with the operator's input, may update the caller's member profile, request written materials, generate referrals, order prescriptions, or generate reports.

U.S. Pat. No. 5,845,255, entitled "Prescription Management System," relates to a wirelessly deployable, electronic prescription creation system for physician use captures into a prescription a patient condition-objective of the prescribed treatment and provides for patient record assembly from source elements, with privacy controls for patient and doctor, adverse indication review and online access to comprehensive drug information including scientific literature. Extensions to novel multi-drug packages and dispensing devices, and a remote data retrieval architecture as well as onscreen physician-to-pharmacy and physician-to-physician e-mail are also provided.

U.S. Pat. No. 7,020,618, entitled "Method and System for Customer Service Process Management," relates to a method and system for managing customer service processes for individual customers and populations of customers. A clinician creates or updates a draft care plan for a patient using generic or locally-adapted template metadata and tailors the draft care plan to the particular patient. The draft care plan includes a list of specific services (health care interventions) to be provided to the patient. The draft care plan can be routed to members of an inter-disciplinary team for input. Once finalized, workflow processes are instantiated for each intervention on the care plan. An itinerary is created for any required patient encounters, optimized using an algorithm that considers pre-existing process instances. A workflow automation server manages the execution of each workflow process instance, invoking resources according to workflow process specification metadata and workflow task type metadata. Care plans and encounter itineraries are automatically translated to a patient-understandable form and made available to patients online and via printed copy. Clinical practice and outcomes data are analyzed to identify opportunities for improvement of the metadata. The method and system also allows for the selection of a population of patients, the analysis of population data to identify opportunities for interventions (needed services), and the initiation of population interventions through batch updates to individual care plans.

U.S. patent application 2003/0225595 entitled "Prescription Management System," also assigned to the assignee of the present invention, relates to a medical prescription order processing method for mail order pharmacy industry, and involves processing an order by executing actions necessary to progress the order from an initial queue to a final queue. An imaging and workflow method, system, and computer readable medium and user interface is provided for processing information efficiently for medical prescription orders. The system includes support for document scanning, automated rules-based order processing, statistical reporting, document generation and document storage and retrieval. The system takes advantage of imaging technology to assist the user in scanning information into the system and software modules to improve the processing of orders. The system also includes database tables that identify to application processing logic the types and sequences of actions to be implemented for orders.

U.S. patent application 2005/0060197 entitled "Computerized Prescription System for Gathering and Presenting Information Relating to Pharmaceuticals," relates to professional data management systems useful in the production of product specification documents such as prescriptions, service or parts orders, insurance contracts and the like that require detailed product and history information from multiple extensive information sources, especially remote sources. More particularly, the system assists professionals perform their everyday work in specifying customized technical products. One embodiment relates to a computer-implemented prescription management system that assists physicians in prescribing and reviewing drugs.

Thus, none of the above patents directly deal with managing and/or administrating a prescription benefit plan or program. Accordingly, there exists a need for a prescription benefits management system that is effectively and efficiently managed, and that overcomes these and other deficiencies in prior art systems.

SUMMARY OF THE INVENTION

In accordance with the present invention, systems and methods for managing, administering, sponsoring and/or maintaining prescription benefit plans are provided (hereinafter "prescription benefits management application"). The prescription benefits management application comprises a web application constructed using WebSphere and Java technology with the business objective to exceed service levels in the Third Party Administrator, Health Plan, and Broker-Direct Markets for web-based transmission of prescription benefit and coverage information for new contracts and/or groups within, for example, 48 to 72 hours, or even faster.

The prescription benefits management application enables users to:

Add and maintain a client name and primary information

Add Broker involvement and contact information (if applicable)

Set-up billing, who's responsible to pay the prescription benefits manager, sponsor and/or administrator and where to send the invoices Add and maintain a group name and primary information Select and maintain program type (of prescription coverage; mail order, retail, combined)

Select pharmacy network (networks of retail pharmacies contracted by the prescription benefits manager, sponsor and/or administrator)

Select pricing options (how prescription claims will be priced at point of sale)

Set-up and maintain member co-payments/co-insurance

Set-up and maintain Brand/Generic difference overrides based on physician directions on the prescription to Dispense As Written (DAW)

Add and maintain Deductible, CAP, and Out Of Pocket (OOP) limitations

Select and maintain Prescription Drug Coverage (Drug Plan) and days supply coverage for program type Set-up and maintain Dependent Coverage Set-up and maintain General Benefits including overrides of specific benefit plan rules at point of sale Automatically creates and emails Summary documents containing the users' selections for adding a contract, a group, and group benefits According to some embodiments of the invention, the prescription benefits management application allows website users to electronically add a contract (client) to their existing carrier through the Client Website in a secure manner. By using the tool, clients can:

- Add a client name and primary information
- Add Broker involvement and contact information (if applicable)
- Set-up billing, who's responsible to pay the prescription benefits manager, sponsor and/or administrator and to what address the invoices (for payment) should be sent to
- Once the contract (client) has been successfully added, new groups and benefits can be added
- Clients can add contracts (clients) at any time. The tool is convenient to use and cost-effective—it allows users to add clients to their existing carrier using the Client Website. The user simply logs on the Client Website and clicks I Want To . . . 'Add Groups or Benefit Changes'. The user is taken to a list of exiting clients and clicks the ADD CLIENT button and completes the set-up and clicks CONFIRM.
- The prescription benefits management application is designed for clients to add contracts (clients) to their existing carrier from their desktop PC through the Client Website. Ideal clients include:
- Current System Third Party Administrator (TPA) clients that submit requests to add contracts (clients) via current manual processes. By using the tool, clients can significantly expedite and streamline the Add Contract process and reduce mailing/phone costs.
- New System TPA clients that want to add contracts (clients) using the Internet.

According to some embodiments of the invention, the Group Add tool allows website users to electronically add groups to an existing plan design and contract (client) or modify existing group's plan design through the Client Website in a secure manner. By using the tool, clients can:

- Add a group name and primary information
- Select program type
- Select pharmacy network
- Select pricing options
- Set-up member co-payments/co-insurance
- Set-up Brand/Generic difference overrides
- Add Deductible/CAP/OOP
- Select Drug Plan and days supply coverage for program type
- Set-up Dependent Coverage
- Clients can add groups and benefits at any time. The tool is convenient to use and cost-effective—it allows users to add clients to their existing carrier using the Client Website. The user simply logs on the Client Website and clicks I Want To . . . 'Add Groups or Benefit Changes'. The user is taken to a list of exiting clients, selects a client and clicks the ADD GROUP button and completes the set-up and clicks CONFIRM.
- Clients can modify group benefits at any time. The tool is convenient to use and cost-effective—it allows users to add clients to their existing carrier using the Client Website. The user simply logs on the Client Website and clicks I Want To . . . 'Add Groups or Benefit Changes'. The user is taken to a list of exiting clients, selects a client, selects a group, and clicks on the type of benefit they wish to modify on the left navigation bar.
    - Co-payment (co-insurance), Deductible, CAP, Out of Pocket (OOP), Drug Plan, General Benefits, Communications
- Clients can view Audit Summary of Group Benefit changes. The Audit Summary is available on the Group Summary page. This report allows the user to easily verify recent changes made to the benefit and who made them. If needed, the user can request a full audit summary report from their account management team.

In some embodiments of the present invention, the prescription benefits management application supports web-based transmission of prescription benefit and coverage information for new contracts and/or groups or changes to existing information within 48 hours. Assigning client specific contract and group numbers is also optionally supported.

In some embodiments of the present invention, the prescription benefits management application supports one or more of the following application functionality:

1. Search for Contract/Group Record
2. List Contracts
3. List Groups
4. Add Contract
5. Add Group
6. Add Group Benefit Choices
7. Add Group Drug Plan (Coverage)
8. Add Group Copay
9. Add Group Pricing
10. Maintain Contract
11. Maintain Group Benefit Choices
12. Maintain Drug Categories
13. Maintain Copay
14. Display Contract and Group Summary Information
15. Display On Line Help Information
16. View Audit Trail Information
17. Terminate Contract
18. Terminate Group
19. Administer User Roles supported
20. Secure User Log-in In accordance with the present invention, systems and methods are provided for managing, administering, sponsoring and maintaining prescription benefit and coverage information for one or more users.

In accordance with some embodiments of the present invention, methods and systems for managing prescription drug benefits are provided, where in response to receiving a request from a user computing device to access an account, the user computing device is provided with account information. The account may include one or more contracts. Account information may include, for example, information relating to each contract. In response to receiving a request to add a new contract to the account, the user computing device is provided with an opportunity to input information relating to the new contract. Such information includes information relating to prescription benefits and coverage, information relating to a broker, and information relating to billing. Upon adding the new contract, a contract summary for display on the user computing device is automatically generated.

In accordance with some embodiments of the present invention, the methods and systems for managing prescription drug benefits provide features for modifying and/or maintaining group members associated with a contract. For example, in response to receiving a request from the user computing device to modify a group member of one of the contracts, the user computing device is provided with an opportunity to input information relating to the group member. The information includes at least one of information relating to a type of prescription program, pharmacy network, pricing options, co-payments, prescription overrides, deductibles, drug plan, and prescription benefits and coverage. In response to modifying and/or maintaining the group member, a group summary for display on the user computing device is automatically generated.

In accordance with some embodiments of the present invention, the user computing device may create a customized drug plan. In some embodiments, the user at the user computing device may indicate that a plurality of generic prescription drugs and/or a plurality of brand prescription drugs be included in a customized drug plan.

In accordance with some embodiments of the present invention, the methods and systems for managing prescription drug benefits allow a pharmacist at another user computing device to access the prescription benefits management application. In response to receiving a request from the user computing device to modify a group member of one of the contracts, the user computing device is provided with an opportunity to input information relating to the group member. The information includes at least one of information relating to a type of prescription program, pharmacy network, pricing options, co-payments, prescription overrides, deductibles, drug plan, prescription benefits and/or prescription coverage. In response to modifying and/or maintaining the group member, a notification informing the pharmacist of the modification is transmitted to the pharmacist at another user computing device. In response, the pharmacist may access information relating to the group member, thereby allowing the pharmacist to fill one or more prescriptions for the group member using the transmitted information.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments, different combinations of embodiments described herein, and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

Additional embodiments of the invention, its nature and various advantages, will be more apparent upon consideration of the following detailed description, taken in conjunction with the accompanying drawings, in which like reference characters refer to like parts throughout, and in which:

FIG. 6 is an illustrative client content information screen that may be provided by the prescription benefits management application in accordance with some embodiments of the present invention;

Figure 7:
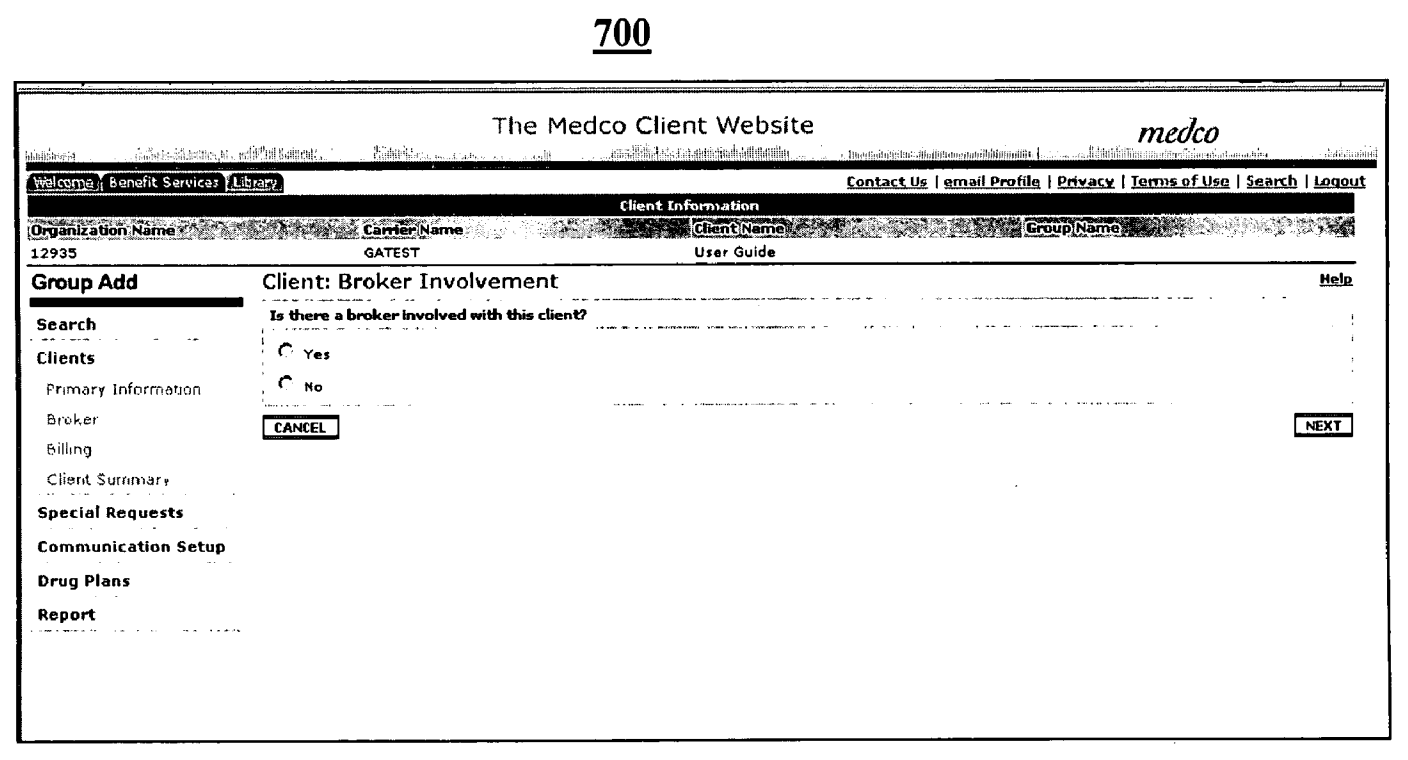

FIG. 7 is an illustrative broker involvement screen that may be provided by the prescription benefits management application in accordance with some embodiments of the present invention;

Figure 8:
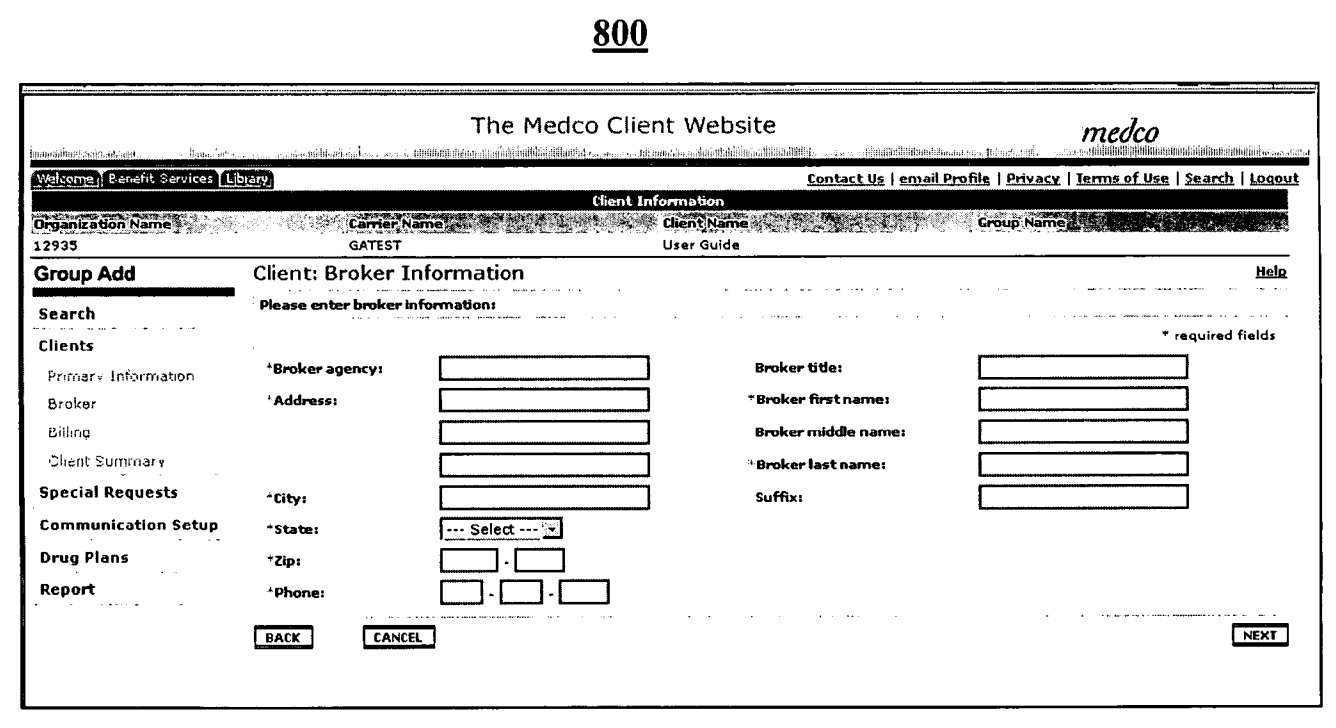

FIG. 8 is an illustrative broker information screen that may be provided by the prescription benefits management application in accordance with some embodiments of the present invention;

FIG. 9 is an illustrative billing information screen that may be provided by the prescription benefits management application in accordance with some embodiments of the present invention;

FIG. 10 is an illustrative billing address information screen that may be provided by the prescription benefits management application in accordance with some embodiments of the present invention;

FIG. 11 is an illustrative client summary screen that may be provided by the prescription benefits management application in accordance with some embodiments of the present invention;

FIG. 12 is an illustrative client listing screen that may be provided by the prescription benefits management application in accordance with some embodiments of the present invention;

FIG. 13 is an illustrative group information screen that may be provided by the prescription benefits management application in accordance with some embodiments of the present invention;

FIG. 14 is an illustrative program selection screen that may be provided by the prescription benefits management application in accordance with some embodiments of the present invention;

FIG. 16 is an illustrative reimbursement option screen that may be provided by the prescription benefits management application in accordance with some embodiments of the present invention;

FIG. 17 is an illustrative pricing option summary screen that may be provided by the prescription benefits management application in accordance with some embodiments of the present invention;

FIG. 18 is an illustrative co-payment program type screen that may be provided by the prescription benefits management application in accordance with some embodiments of the present invention;

FIG. 19 is an illustrative co-payment claim different screen that may be provided by the prescription benefits management application in accordance with some embodiments of the present invention;

FIG. 20 is an illustrative co-payment calculation screen that may be provided by the prescription benefits management application in accordance with some embodiments of the present invention;

FIG. 21 is an illustrative co-payment values screen that may be provided by the prescription benefits management application in accordance with some embodiments of the present invention;

FIGS. 25-27 are illustrative deductible information screens that may be provided by the prescription benefits management application in accordance with some embodiments of the present invention;

FIGS. 28-30 are illustrative CAP information screen that may be provided by the prescription benefits management application in accordance with some embodiments of the present invention;

A CAP is a means to limit the benefits allowed to a plan participant. The CAP is the maximum benefit allowed. Benefit period CAPs are the most common and limit the amount an individual or family unit can collect under the plan during a specified time period.

Figure 31:
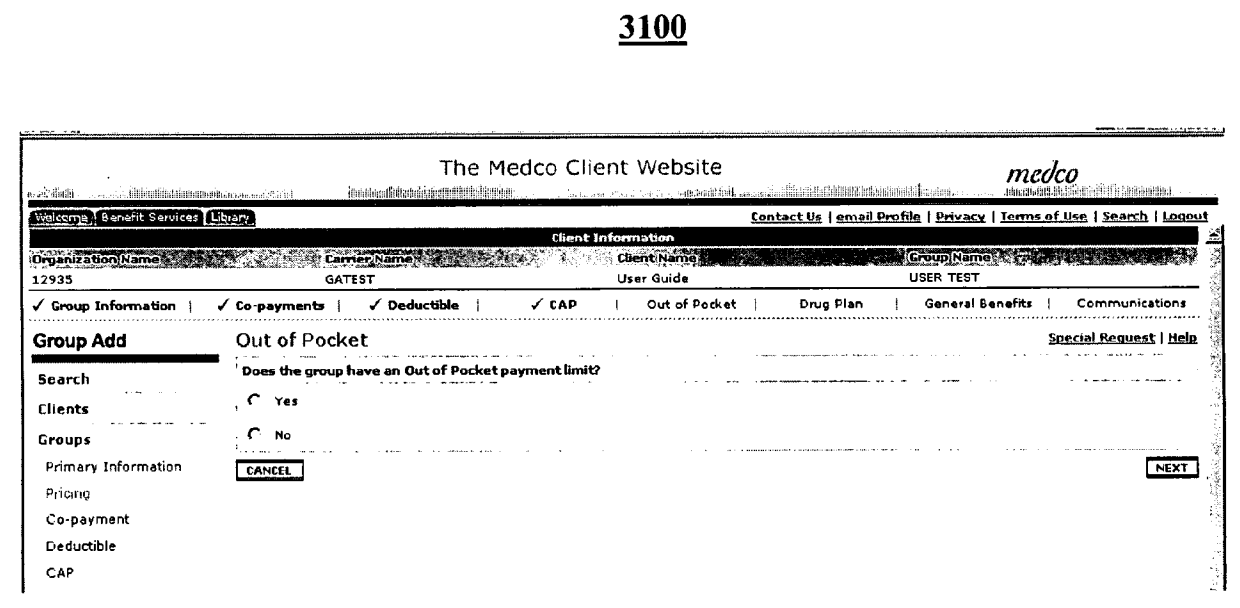
Figure 32:
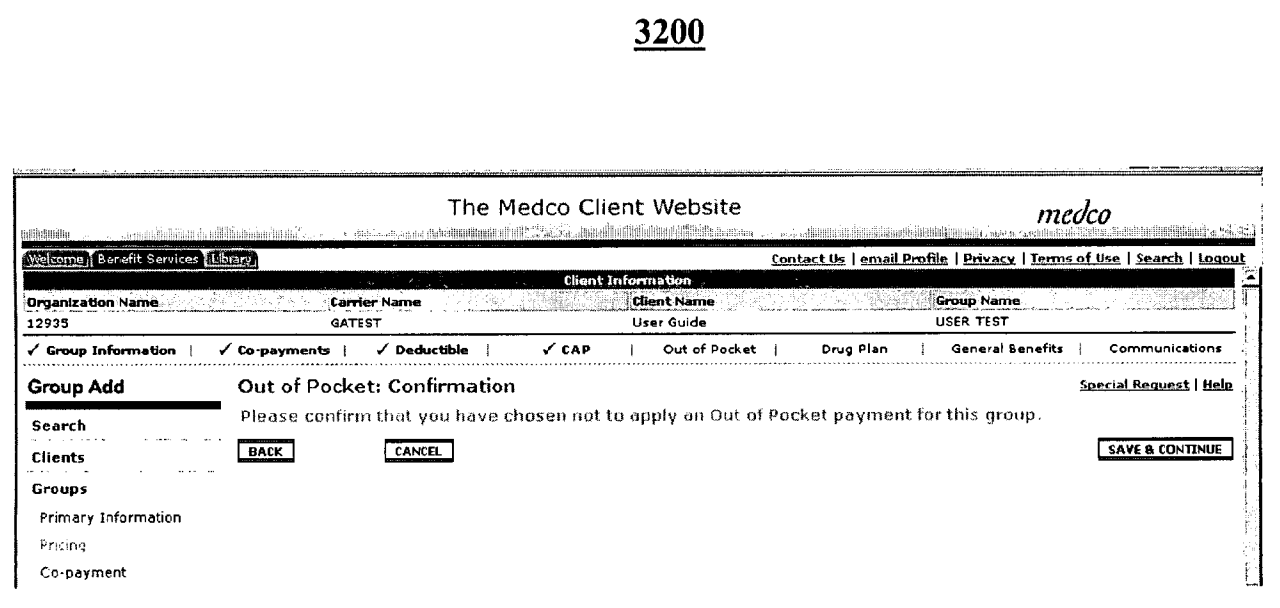
Figure 33:
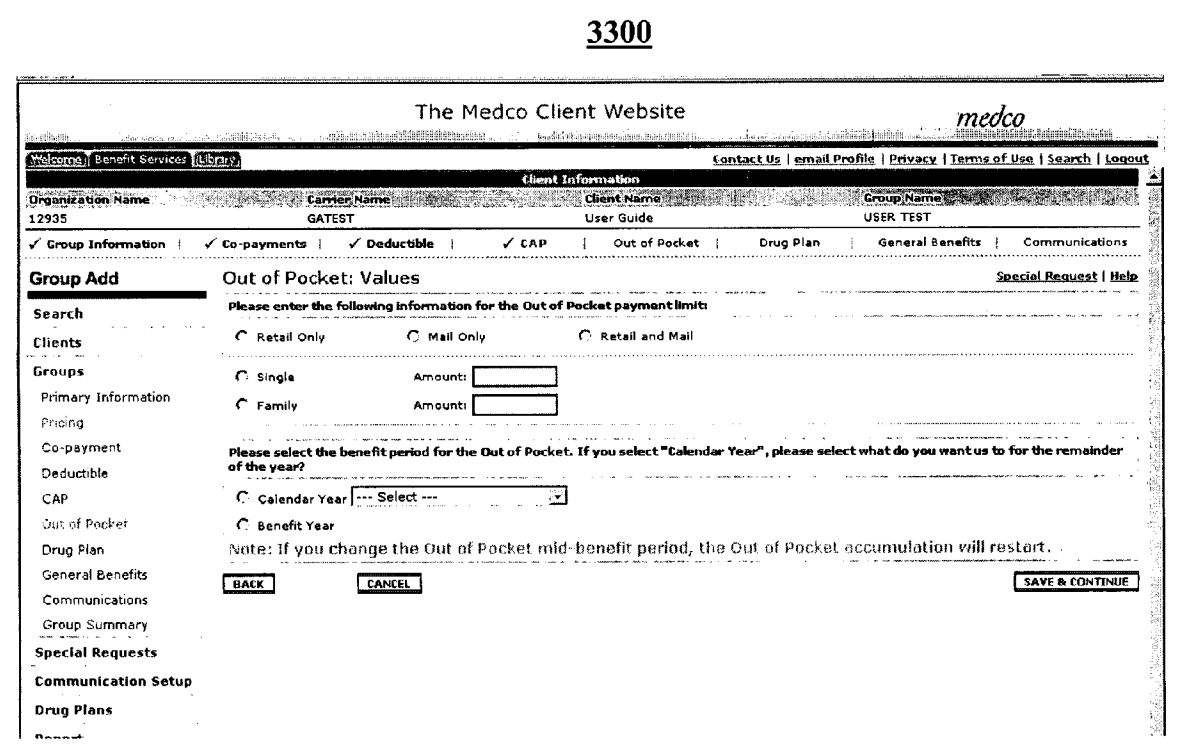

FIGS. 31-33 are illustrative out-of-pocket (OOP) information screen that may be provided by the prescription benefits management application in accordance with some embodiments of the present invention;

An Out-of-Pocket is the maximum amount that a plan participant is required to pay out of his/her own pocket for drugs.

Figure 34:
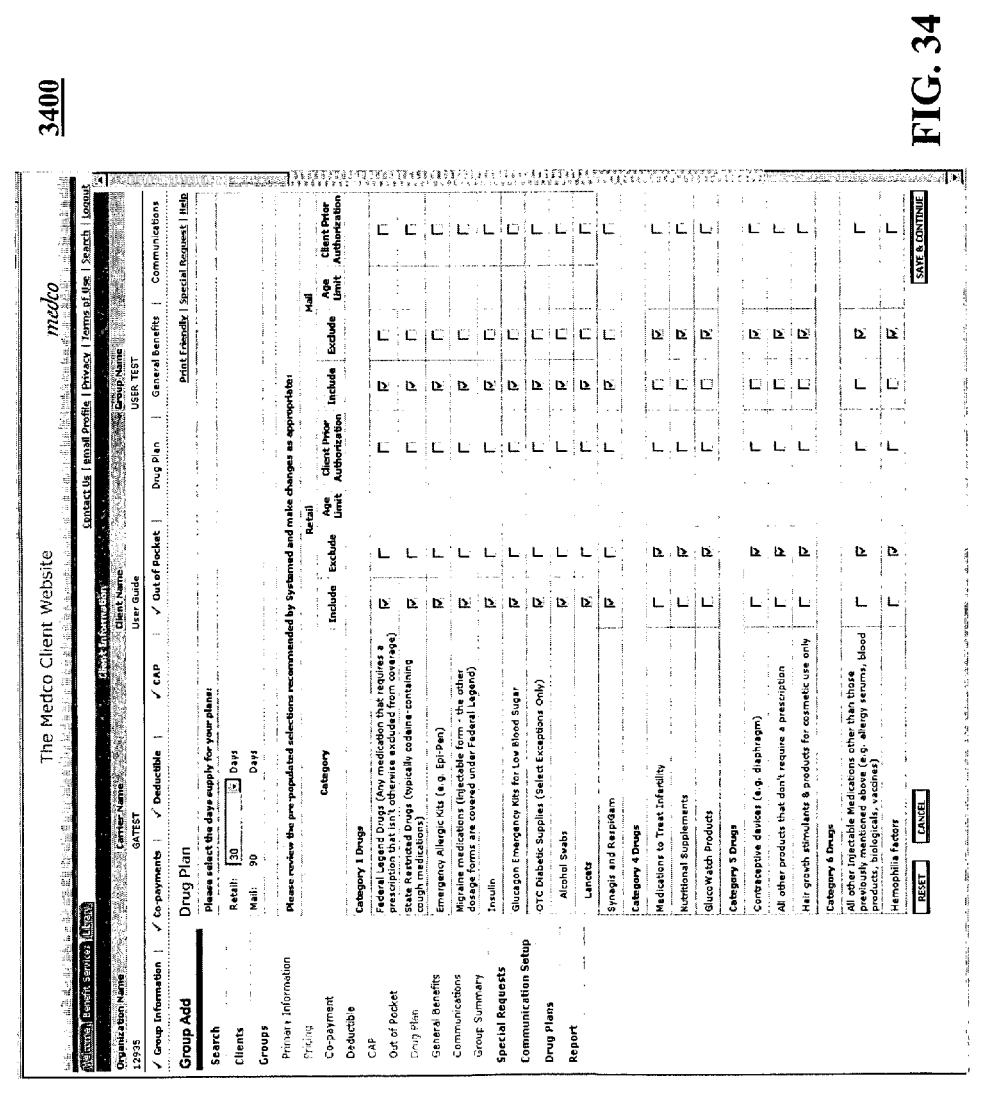
Figure 38:
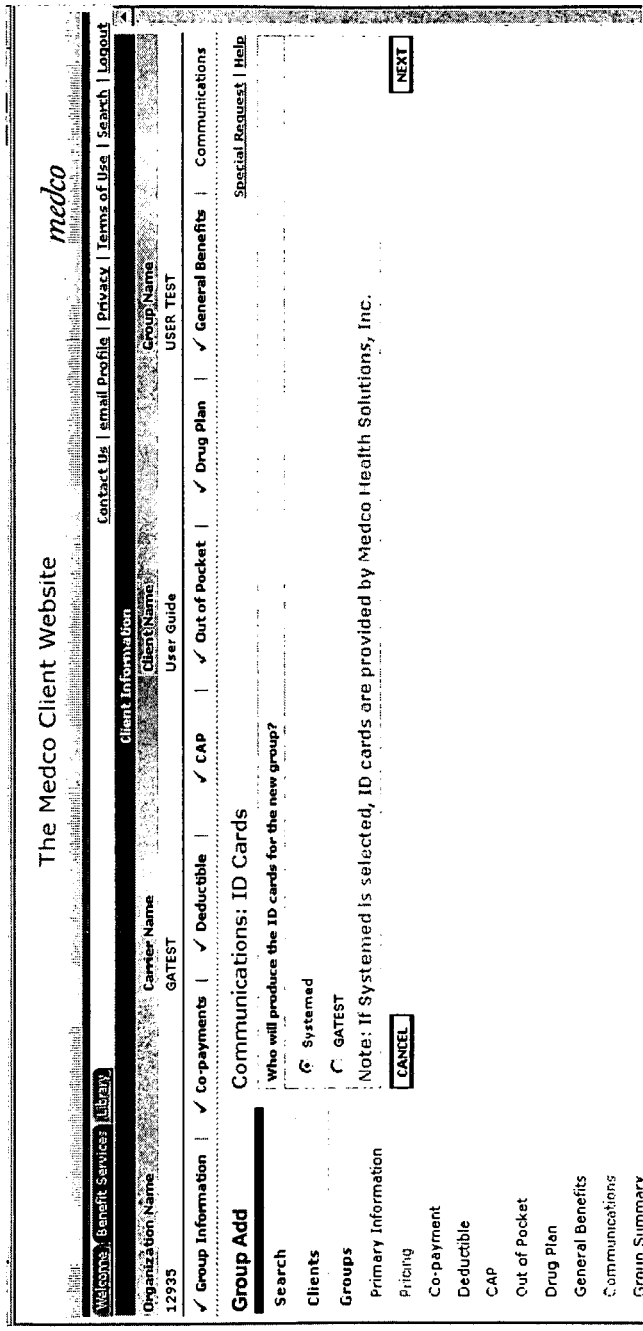
Figure 40:
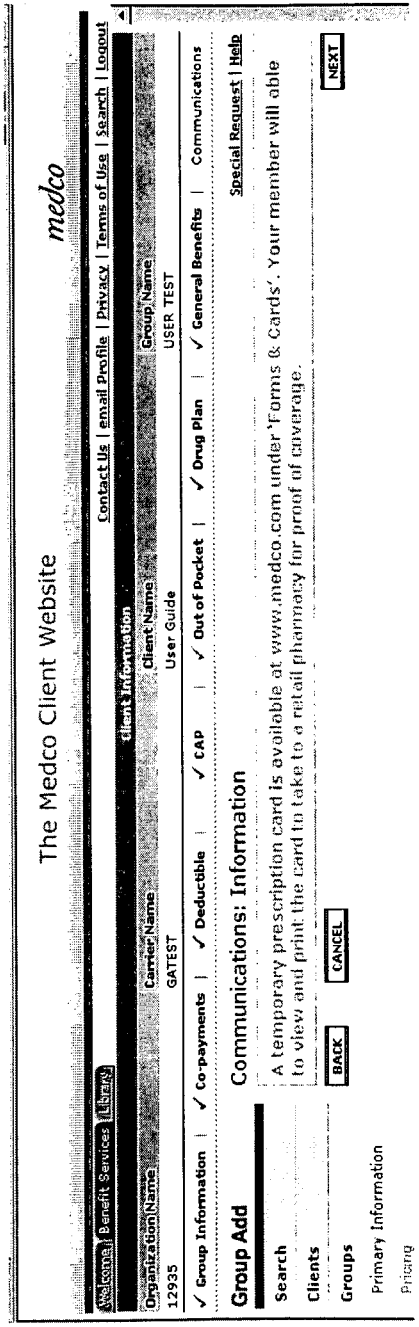
Figure 42:
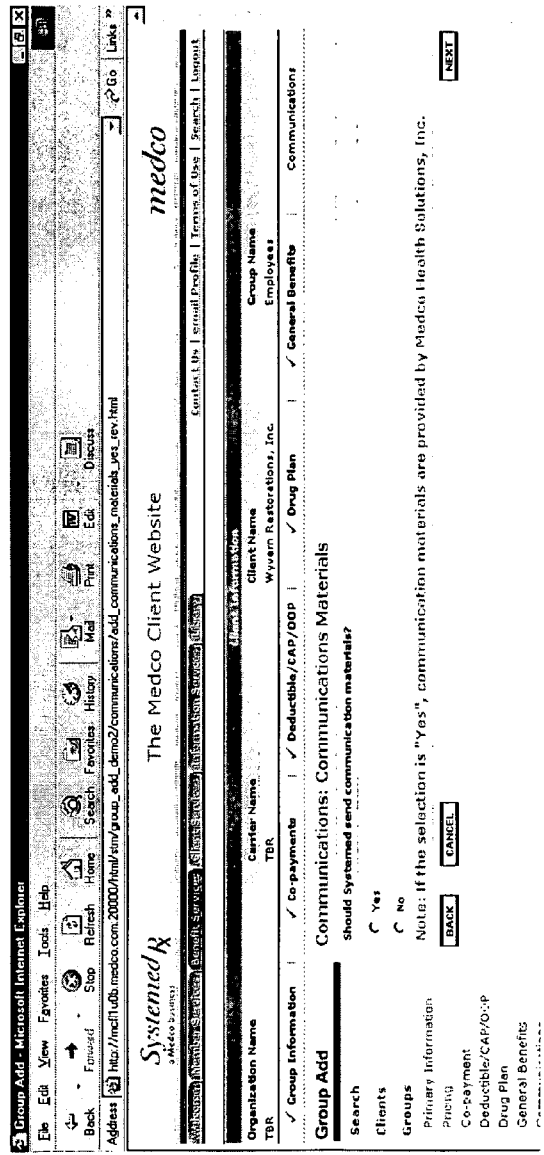
Figure 43:
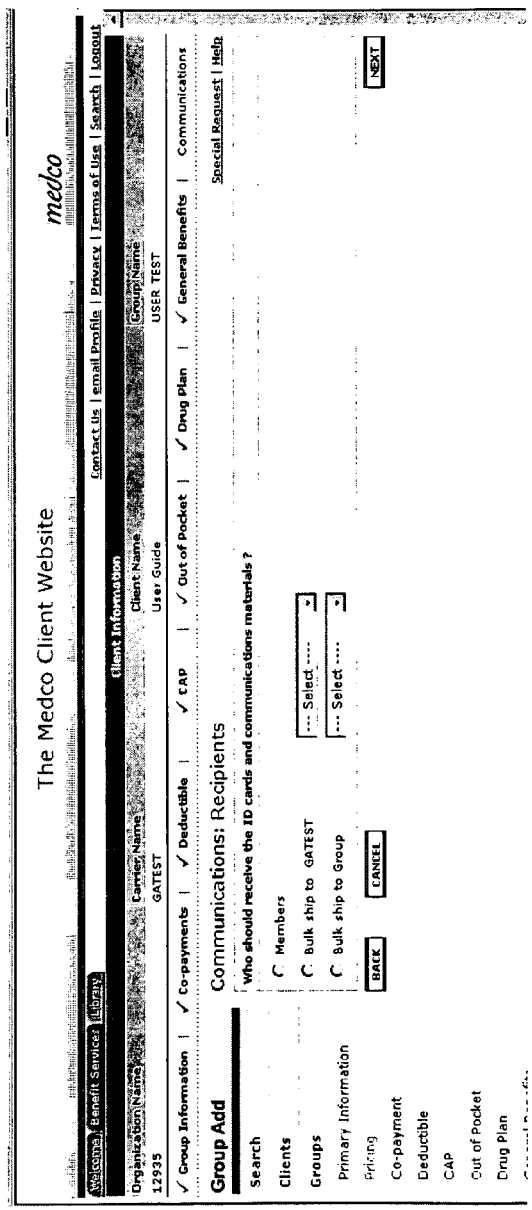
Figure 46:
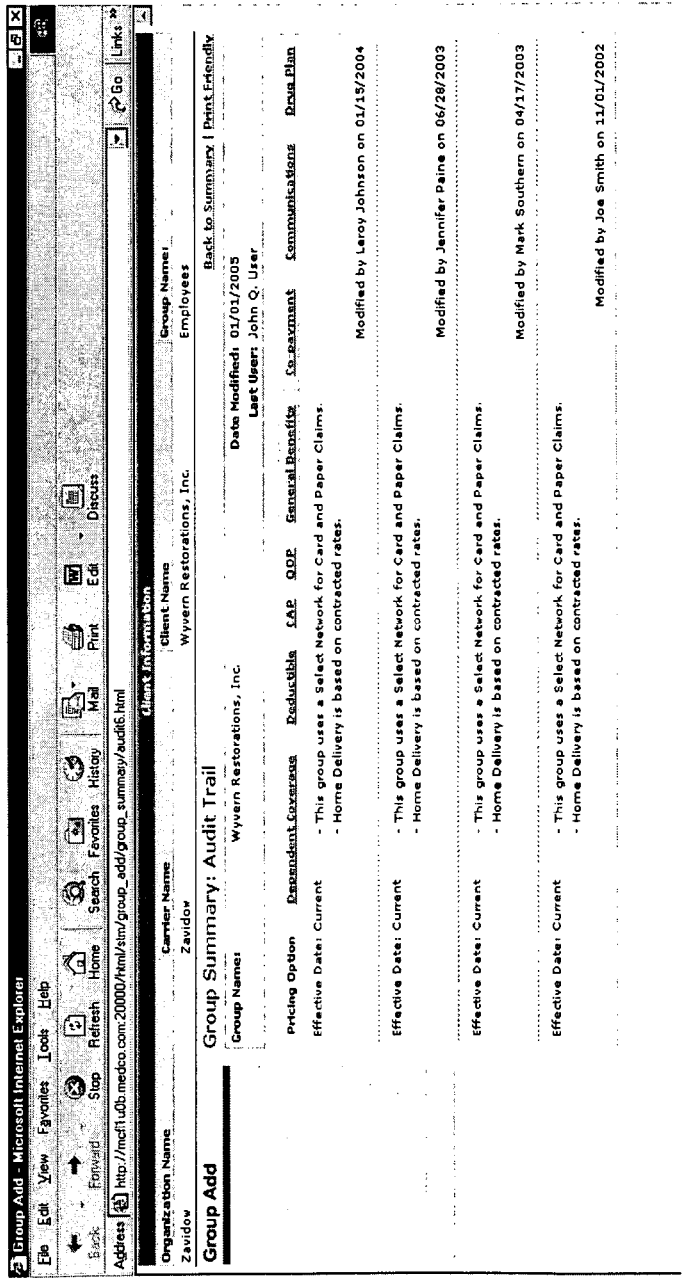
Figure 48:
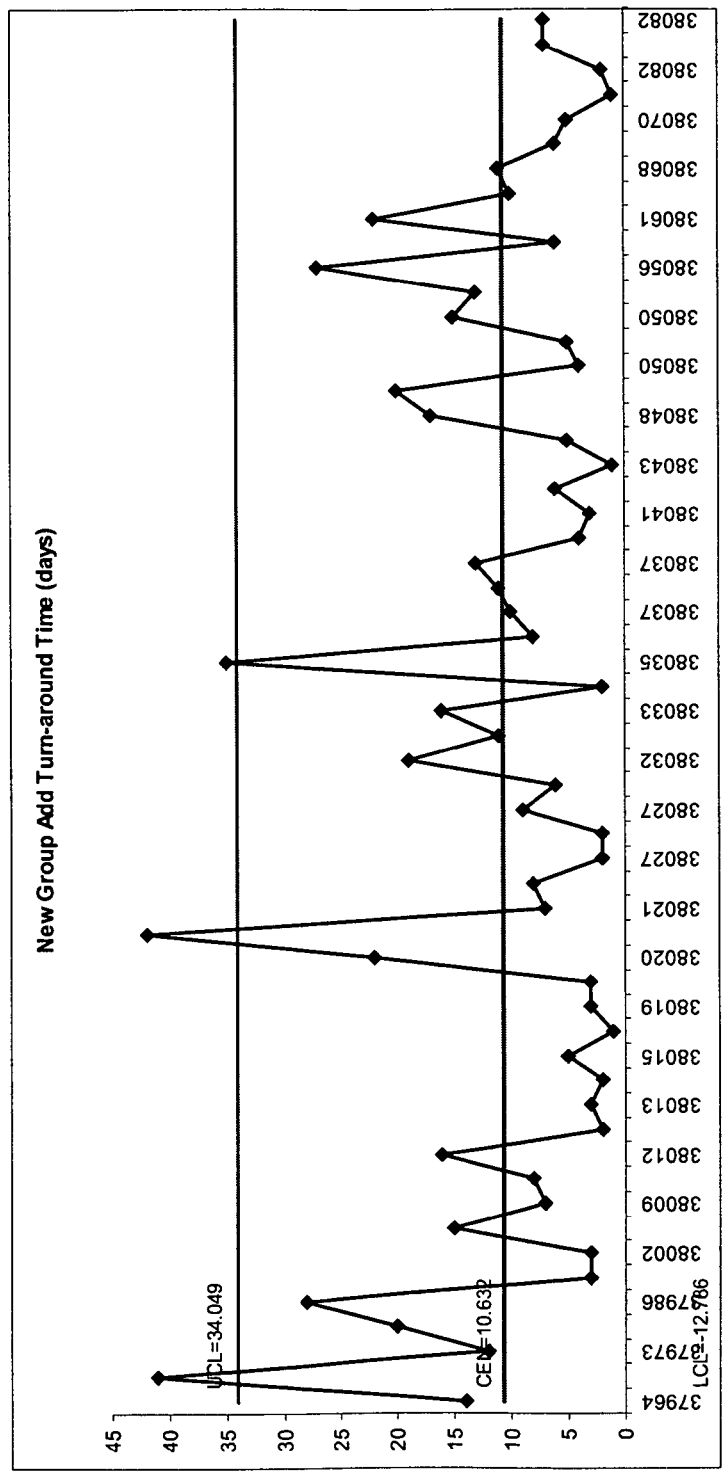
Figure 49:
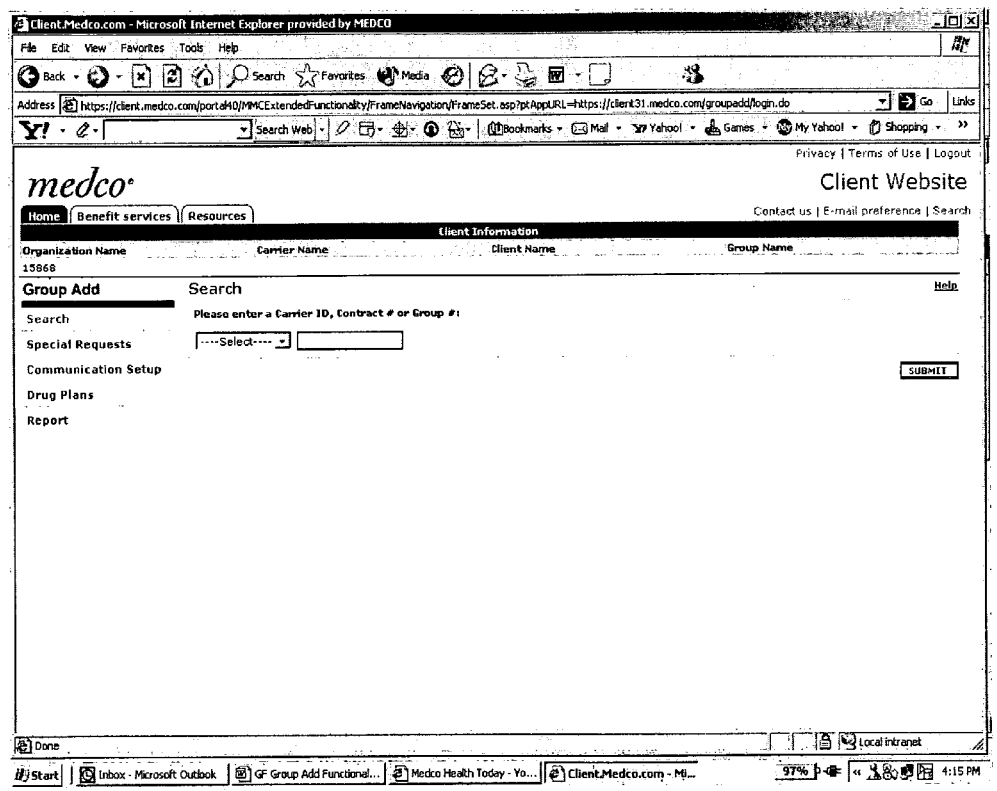
Figure 50:
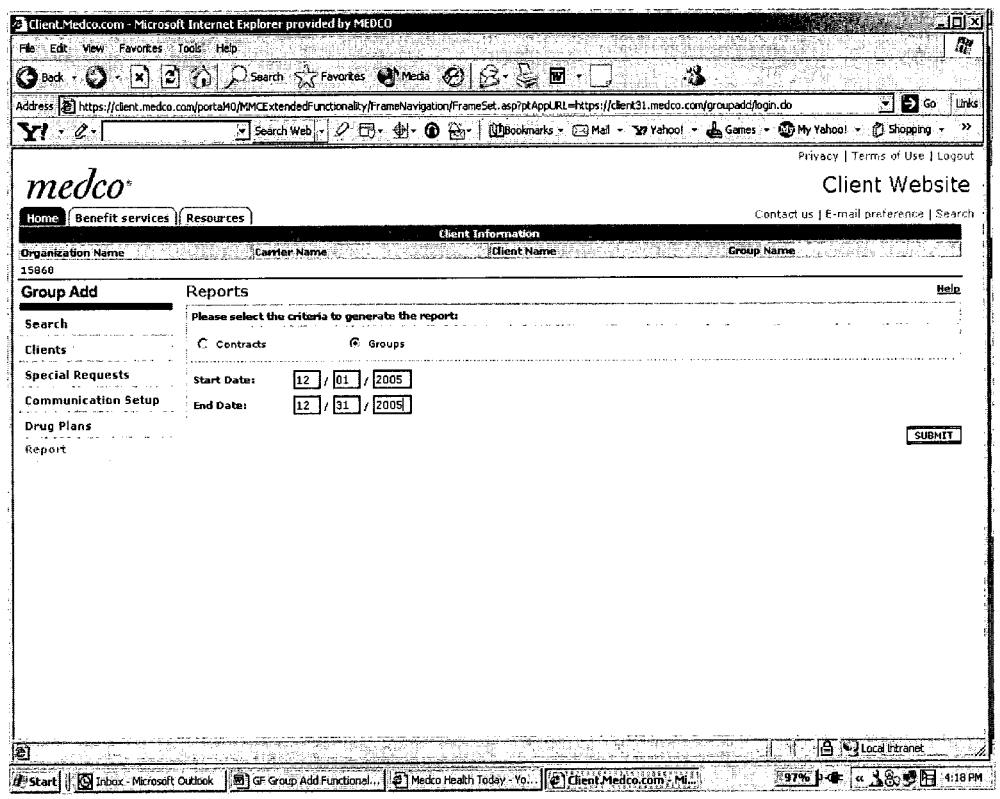
Figure 51:
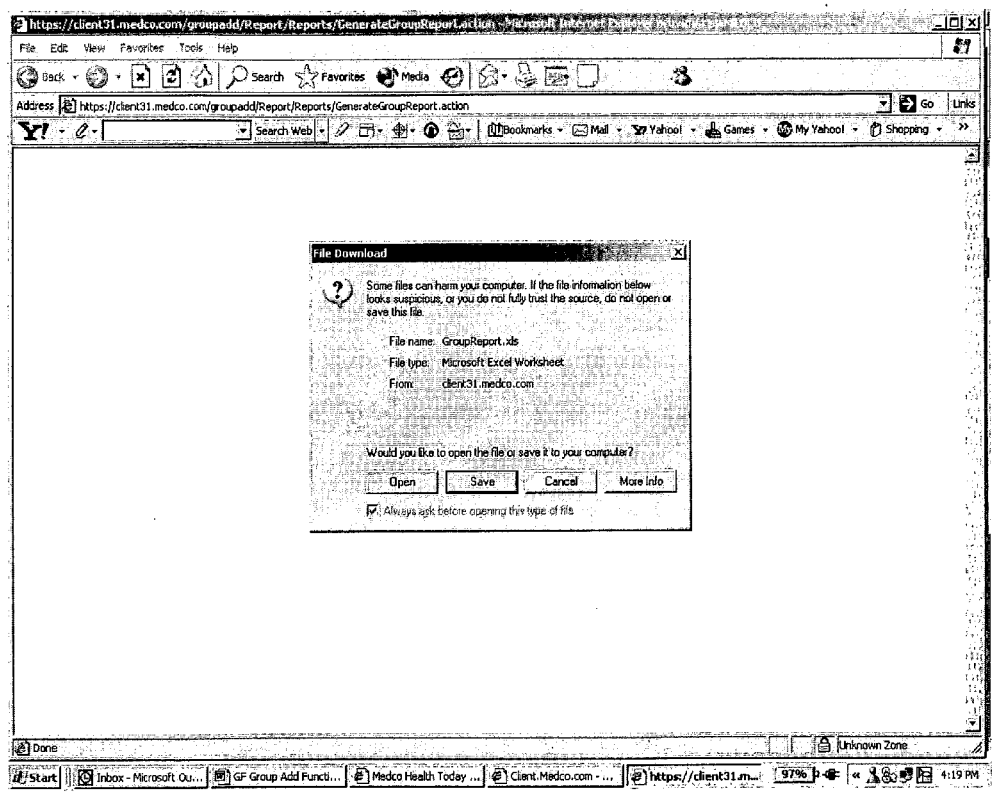
Figure 52:
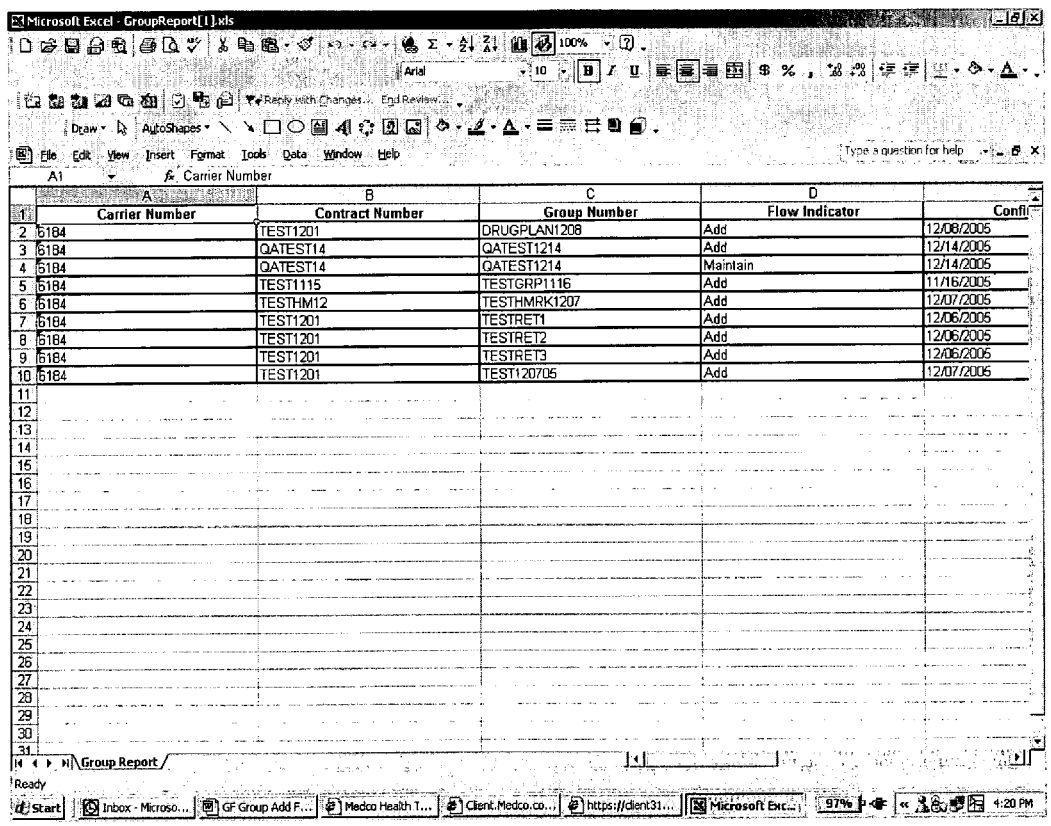

FIG. 34 is an illustrative drug plan screen that may be provided by the prescription benefits management application in accordance with some embodiments of the present invention;

Figure 35:
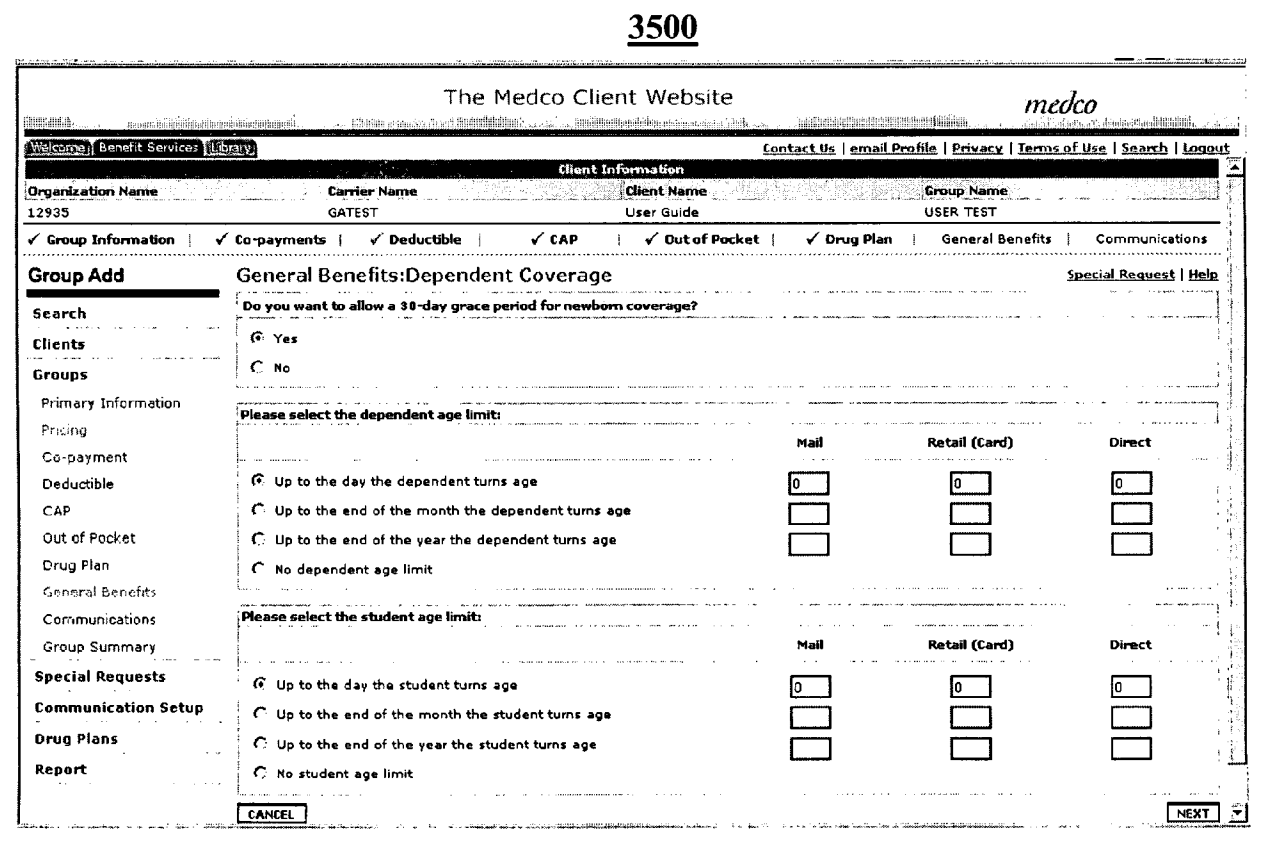

FIG. 35 is an illustrative options screen includes features for newborn coverage, dependent age limit, and/or student age limit that may be provided by the prescription benefits management application in accordance with some embodiments of the present invention;

FIG. 36 is an illustrative options screen includes features for general benefits, refill override options, insulin options, and/or allergy serum options that may be provided by the prescription benefits management application in accordance with some embodiments of the present invention;

Figure 37:
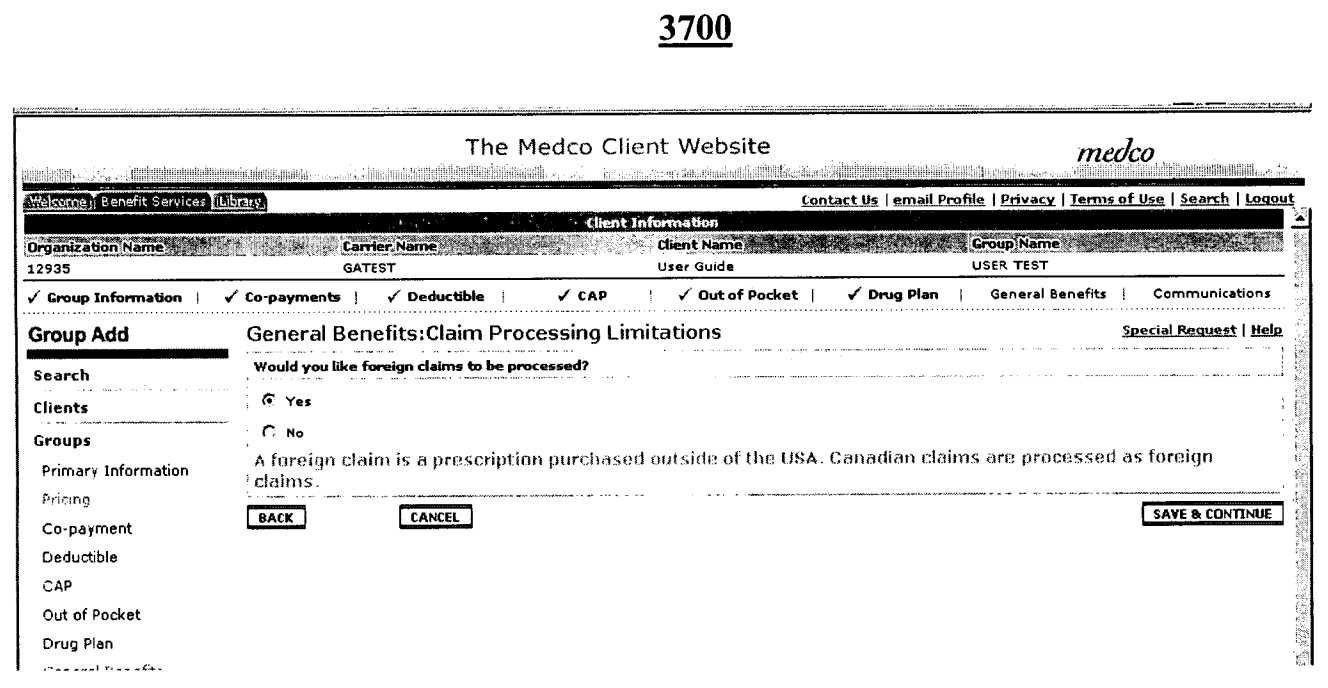

FIG. 37 is an illustrative options screen includes features for claim processing limitations that may be provided by the prescription benefits management application in accordance with some embodiments of the present invention;

FIG. 38 is an illustrative identification card generating screen that may be provided by the prescription benefits management application in accordance with some embodiments of the present invention;

Figure 39:
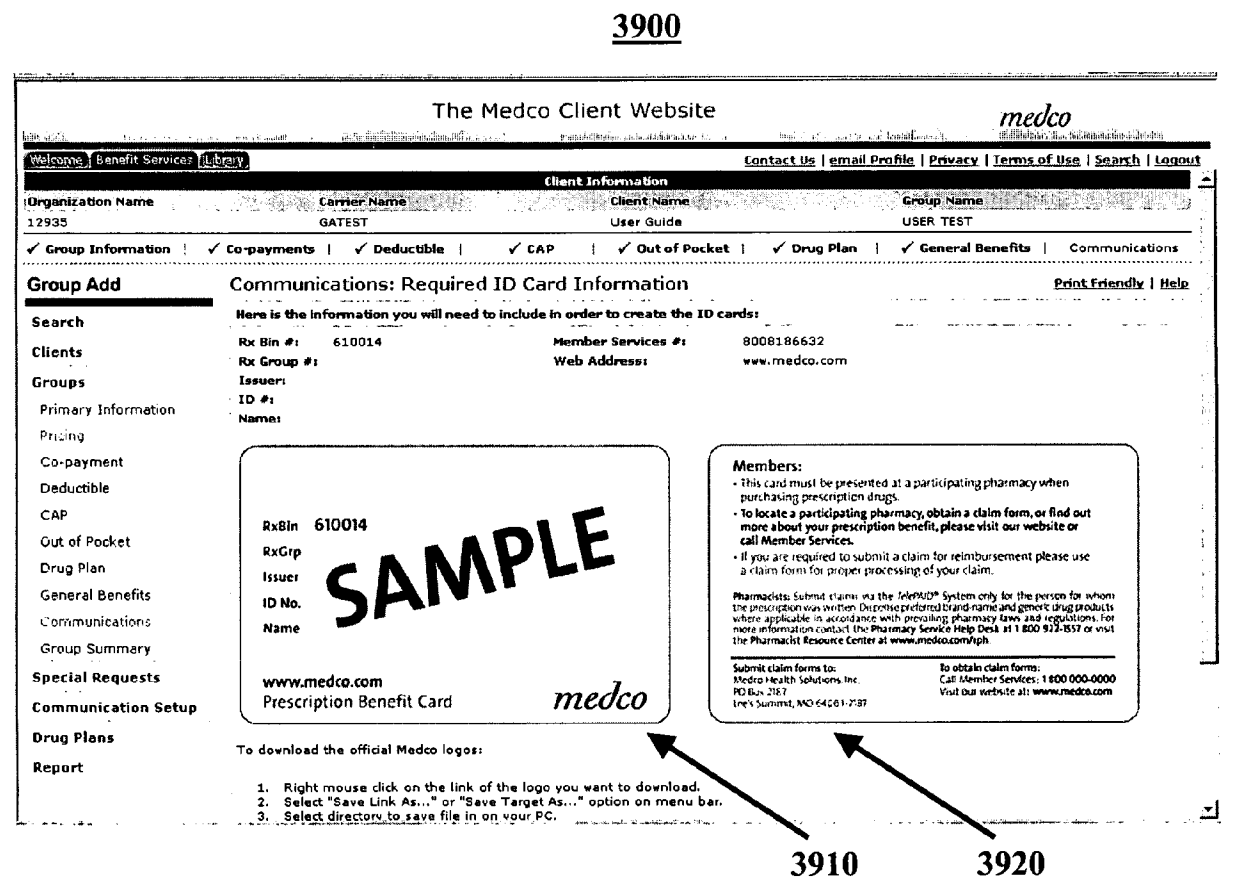

FIG. 39 is an illustrative group member ID card information screen that may be provided by the prescription benefits management application in accordance with some embodiments of the present invention;

FIG. 40 is an illustrative temporary benefit card notification screen that may be provided by the prescription benefits management application in accordance with some embodiments of the present invention;

Figure 41:
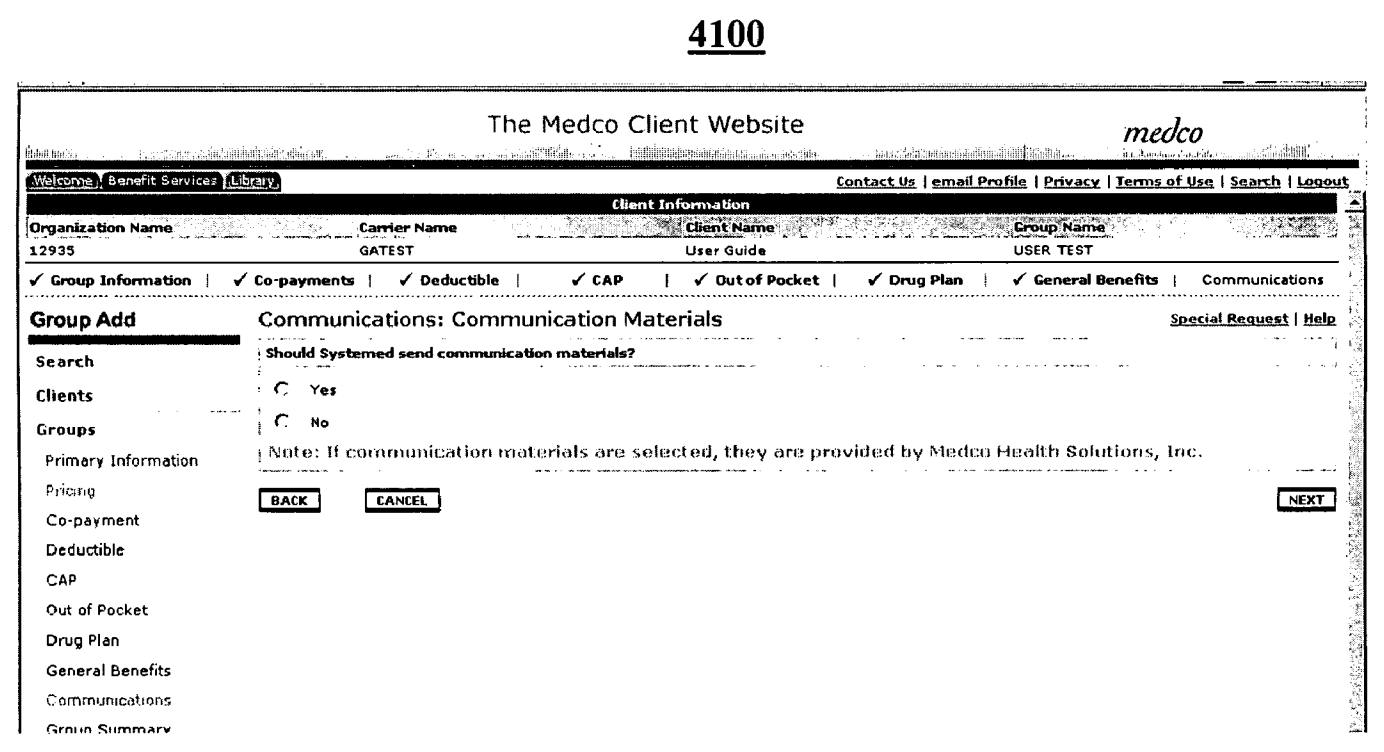
Figure 44:
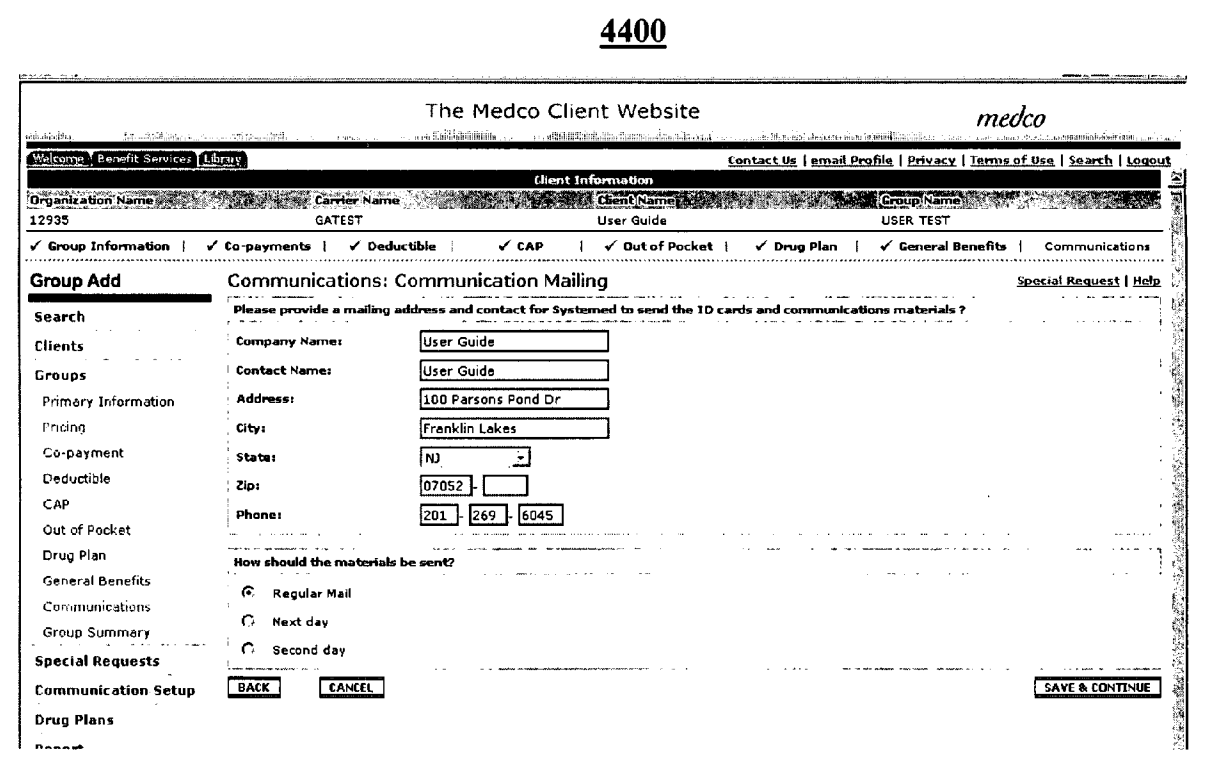

FIGS. 41-44 are illustrative communications materials information screens that may be provided by the prescription benefits management application in accordance with some embodiments of the present invention;

Figure 45:
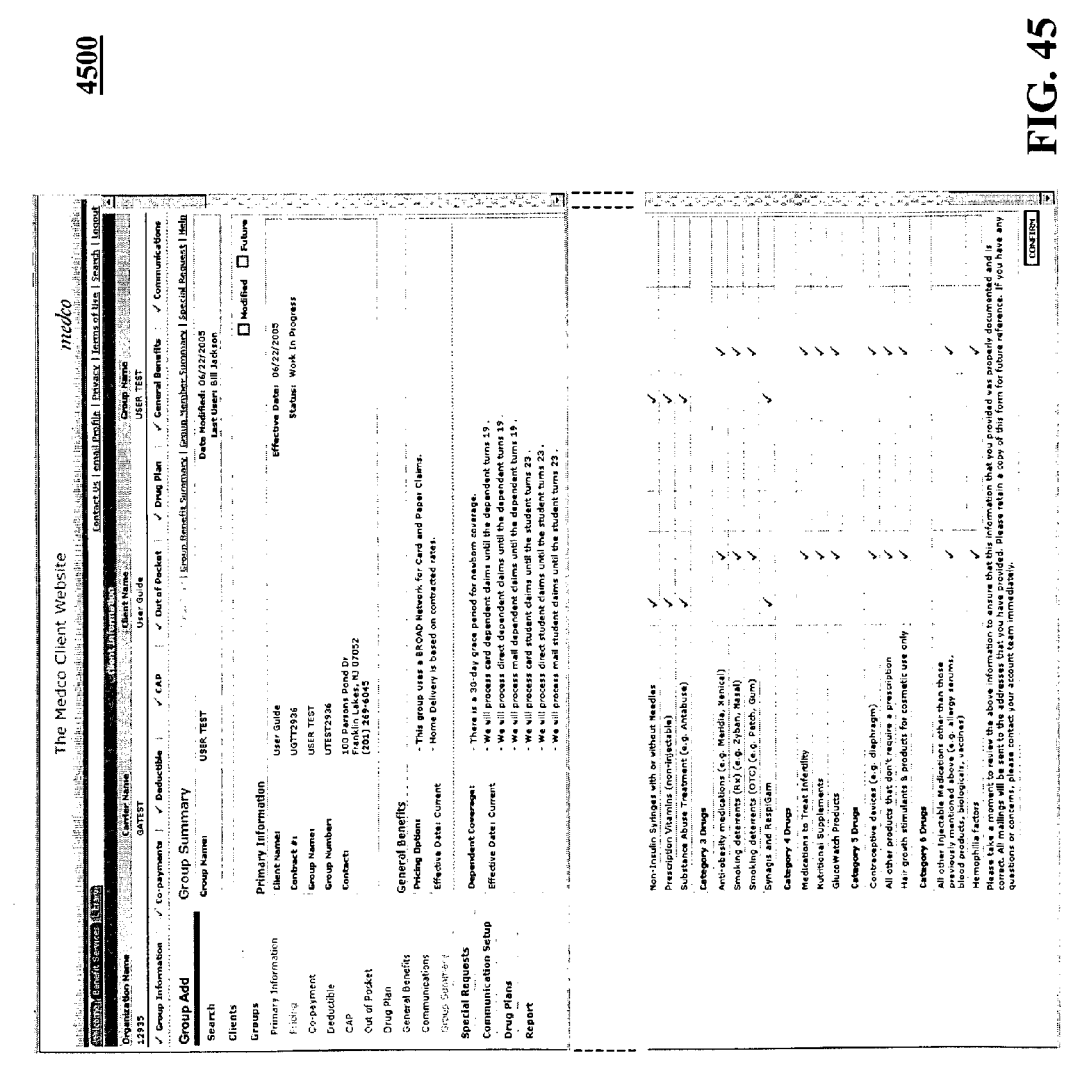

FIG. 45 is an illustrative group summary screen that may be provided by the prescription benefits management application in accordance with some embodiments of the present invention;

FIG. 46 is an illustrative audit trail screen that may be provided by the prescription benefits management application in accordance with some embodiments of the present invention;

Figure 47:
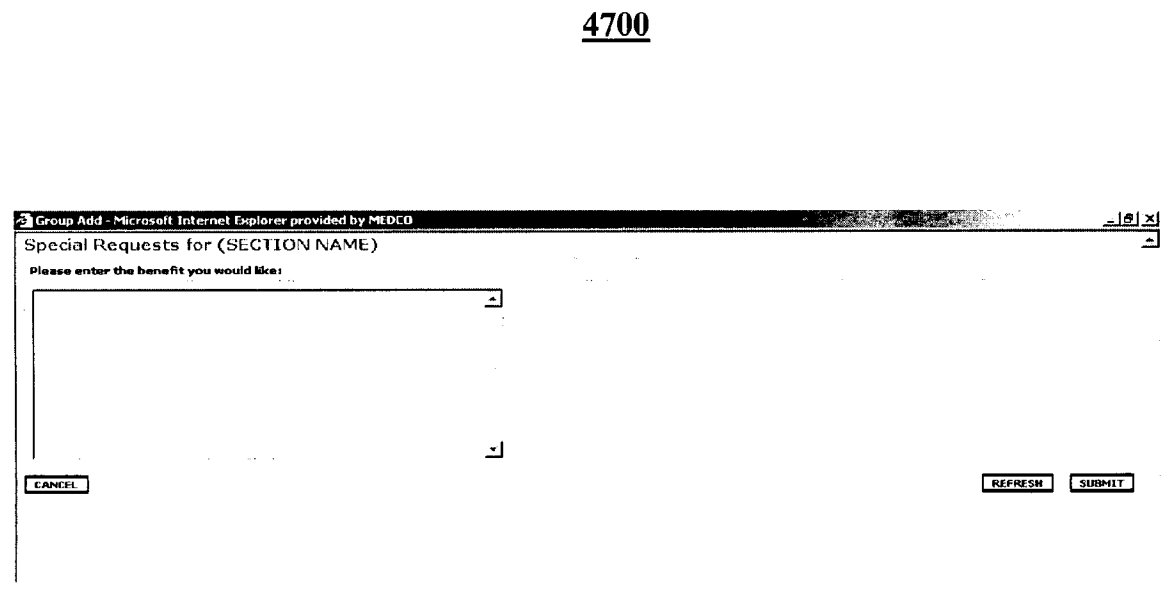

FIG. 47 is an illustrative special requests screen that may be provided by the prescription benefits management application in accordance with some embodiments of the present invention;

FIG. 48 is an illustrative transactions chart that shows the improvement in turn-around-time when using the prescription benefits management application;

FIG. 49 is an illustration of a web interface Contract & Group Add report utility initiation screen;

FIG. 50 is an illustration of a web interface where the user selects Contracts or Groups for the report;

FIG. 51 is an illustration of a web interface where the user may either open the report on-line or save the file;

FIG. 52 is an illustration of a web interface Report Display; and

FIG. 53 is an illustration of a spreadsheet listing a variety of data for the Report Display.

DETAILED DESCRIPTION OF THE INVENTION

The following description includes many specific details. The inclusion of such details is for the purpose of illustration only and should not be understood to limit the invention. Moreover, certain features which are well known in the art are not described in detail in order to avoid complication of the subject matter of the present invention. In addition, it will be understood that features in one embodiment may be combined with features in other embodiments of the invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. Other alterations or modifications of the above processes are also contemplated. For example, further insubstantial approximations of the process and/or algorithms are also considered within the scope of the processes described herein.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

In accordance with the present invention, systems and methods for managing, administering, sponsoring and/or maintaining prescription benefit plans are provided (hereinafter "prescription benefits management application"). A prescription benefits management application may be implemented on the prescription benefits management system of the present invention. The prescription benefits management application may receive information about an existing prescription drug plan or prescription benefit plan. (It should be noted that the term "prescription drug" as used herein may refer to any product or service provided under the prescription drug plan, including, but not limited to, for example, prescription drugs, non-prescription drugs, medical devices, durable medical equipment ("DME"), and/or diabetic supplies.) The plan information may include, for example, plan design information, benefit design information, and/or any other suitable information in connection with the prescription drug plan. The prescription benefits management application may retrieve data in connection with the prescription drug plan, such as claims and membership data. Such data may be stored, for example, in an information warehouse for access by the prescription benefits management application. The prescription benefits management application may, for example, use the retrieved data to assist pharmacists or other authorized users to fill requested prescriptions. In addition, the prescription benefits management application may allow users to perform one or more of the following: add and maintain a client name and primary information, add broker involvement and contact information for the associated broker, setup billing information, add and maintain a group name and primary information, select and maintain program type, select a pharmacy network, select pricing options, setup and maintain member co-payments and/or co-insurance, setup and maintain overrides that allow physicians to indicate that a client or member should not pay for the difference between a brand name drug and a generic drug, create a customized drug plan, and/or allow the user to use any other suitable feature of the prescription benefits management application.

The following FIGS. 1-47 and their accompanying descriptions provide detailed examples of the implementation of the systems and methods of the present invention in accordance with one or more embodiments of the invention.

Figure 1:
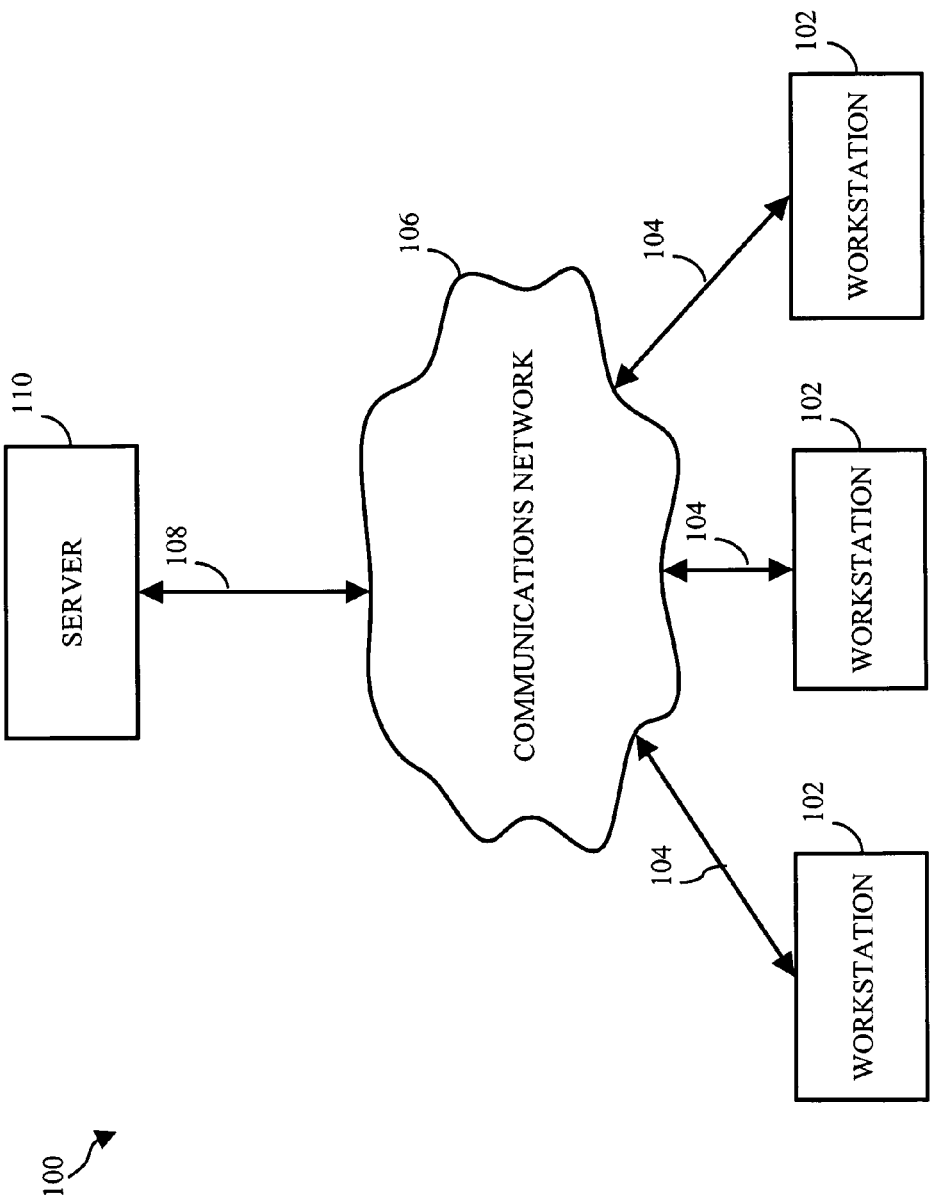
FIG. 1 is a schematic diagram of an illustrative prescription drug plan management system on which a prescription benefits management application may be implemented in accordance with some embodiments of the present invention.

FIG. 1 is a generalized schematic diagram of an illustrative prescription drug plan management system 100 on which a prescription benefits management application may be implemented in accordance with some embodiments of the present invention. As illustrated, system 100 may include one or more workstations 102. Workstations 102 may be local to each other or remote from each other. Workstations 102 are connected by one or more communications links 104 to a communications network 106 that is linked via a communications link 108 to a server 110.

System 100 may include one or more servers 110. Server 110 may be any suitable server for providing access to the prescription benefits management application, such as a processor, a computer, a data processing device, or a combination of such devices. Communications network 106 may be any suitable computer network including the Internet, an intranet, a wide-area network ("WAN"), a local-area network ("LAN"), a wireless network, a digital subscriber line ("DSL") network, a frame relay network, an asynchronous transfer mode ("ATM") network, a virtual private network ("VPN"), or any combination of any of such networks. Communications links 104 and 108 may be any communications links suitable for communicating data between workstations 102 and server 110, such as network links, dial-up links, wireless links, hard-wired links, any other suitable communications links, or a combination of such links. Workstations 102 enable a user to access features of the prescription management application. Workstations 102 may be personal computers, laptop computers, mainframe computers, dumb terminals, data displays, Internet browsers, personal digital assistants ("PDAs"), two-way pagers, wireless terminals, portable telephones, any other suitable access device, or any combination of such devices. Workstations 102 and server 110 may be located at any suitable location. In one embodiment, workstations 102 and server 110 may be located within an organization. Alternatively, workstations 102 and server 110 may be distributed between multiple organizations.

Figure 2:
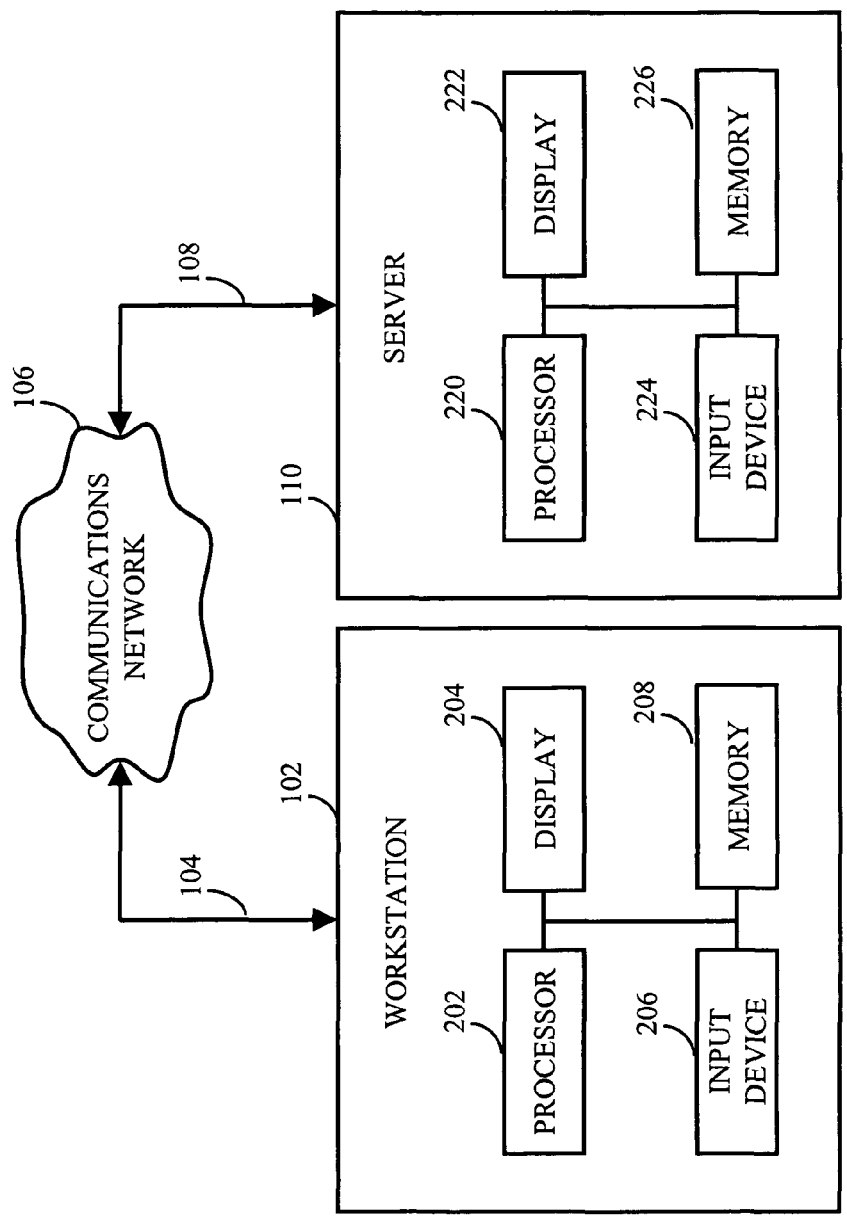
FIG. 2 is a schematic diagram of an illustrative workstation and server as provided, for example, in FIG. 1 in accordance with some embodiments of the present invention.

The server and, for example, one of the workstations, which are depicted in FIG. 1, are illustrated in more detail in FIG. 2. Referring to FIG. 2, workstation 102 may include processor 202, display 204, input device 206, and memory 208, which may be interconnected. In a preferred embodiment, memory 208 contains a storage device for storing a workstation program for controlling processor 202.

Processor 202 uses the workstation program to present on display 204 the application and the data received through communications link 104 and commands and values transmitted by a user of workstation 102. It should also be noted that data received through communications link 104 or any other communications links may be received from any suitable source, such as WebServices. Input device 206 may be a computer keyboard, a cursor-controller, dial, switchbank, lever, or any other suitable input device as would be used by a designer of input systems or process control systems.

Server 110 may include processor 220, display 222, input device 224, and memory 226, which may be interconnected. In a preferred embodiment, memory 226 contains a storage device for storing data received through communications link 108 or through other links, and also receives commands and values transmitted by one or more users. The storage device further contains a server program for controlling processor 220.

In some embodiments, the prescription benefits management application may include an application program interface (not shown), or alternatively, the application may be resident in the memory of workstation 102 or server 110. In another suitable embodiment, the only distribution to workstation 102 may be a graphical user interface ("GUI") which allows a user to interact with the prescription benefits management application resident at, for example, server 110.

In one particular embodiment, the prescription benefits management application may include client-side software, hardware, or both. For example, the application may encompass one or more Web-pages or Web-page portions (e.g., via any suitable encoding, such as HyperText Markup Language ("HTML"), Dynamic HyperText Markup Language ("DHTML"), Extensible Markup Language ("XML"), JavaServer Pages ("JSP"), Active Server Pages ("ASP"), Cold Fusion, or any other suitable approaches).

Although the prescription benefits management application is described herein as being implemented on a workstation and/or server, this is only illustrative. The application may be implemented on any suitable platform (e.g., a personal computer ("PC"), a mainframe computer, a dumb terminal, a data display, a two-way pager, a wireless terminal, a portable telephone, a portable computer, a palmtop computer, an H/PC, an automobile PC, a laptop computer, a personal digital assistant ("PDA"), a combined cellular phone and PDA, etc.) to provide such features.

It will also be understood that the detailed description herein may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are generally machine operations, however, user assisted or performed operations may also be used in combination with the processes described herein. Useful machines for performing the operation of the present invention include general purpose digital computers or similar devices.

The present invention also relates to apparatus for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

The system according to the invention may include a general purpose computer, or a specially programmed special purpose computer. The user may interact with the system via e.g., a personal computer or over PDA, e.g., the Internet, an Intranet, etc. Either of these may be implemented as a distributed computer system rather than a single computer. Similarly, the communications link may be a dedicated link, a modem over a POTS line, the Internet and/or any other method of communicating between computers and/or users. Moreover, the processing could be controlled by a software program on one or more computer systems or processors, or could even be partially or wholly implemented in hardware.

Although a single computer may be used, the system according to one or more embodiments of the invention is optionally suitably equipped with a multitude or combination of processors or storage devices. For example, the computer may be replaced by, or combined with, any suitable processing system operative in accordance with the concepts of embodiments of the present invention, including sophisticated calculators, hand held, laptop/notebook, mini, mainframe and super computers, as well as processing system network combinations of the same. Further, portions of the system may be provided in any appropriate electronic format, including, for example, provided over a communication line as electronic signals, provided on CD and/or DVD, provided on optical disk memory, etc.

Any presently available or future developed computer software language and/or hardware components can be employed in such embodiments of the present invention. For example, at least some of the functionality mentioned above could be implemented using Visual Basic, C, C++ or any assembly language appropriate in view of the processor being used. It could also be written in an object oriented and/or interpretive environment such as Java and transported to multiple destinations to various users.

The prescription benefits management application allows a user (e.g., a benefits administrator) to maintain and modify a contract (e.g., a client) or a group for a prescription drug plan. In response to receiving a request to add or modify a contract and/or a group, a prescription benefits management application may retrieve data relating to the contract or group and allow the user to input information relating to the contract or group, input broker information, input billing information, select a pharmacy network, select pricing options for the prescription plan, create a customized prescription plan, input brand/generic difference overrides, etc. In some embodiments, the modifications and/or additions made to a contract or group may be transmitted to a pharmacist, thereby allowing the pharmacist to fill one or more prescriptions in real-time or upon updating the system (e.g., within 48 to 72 hours).

Figure 3:
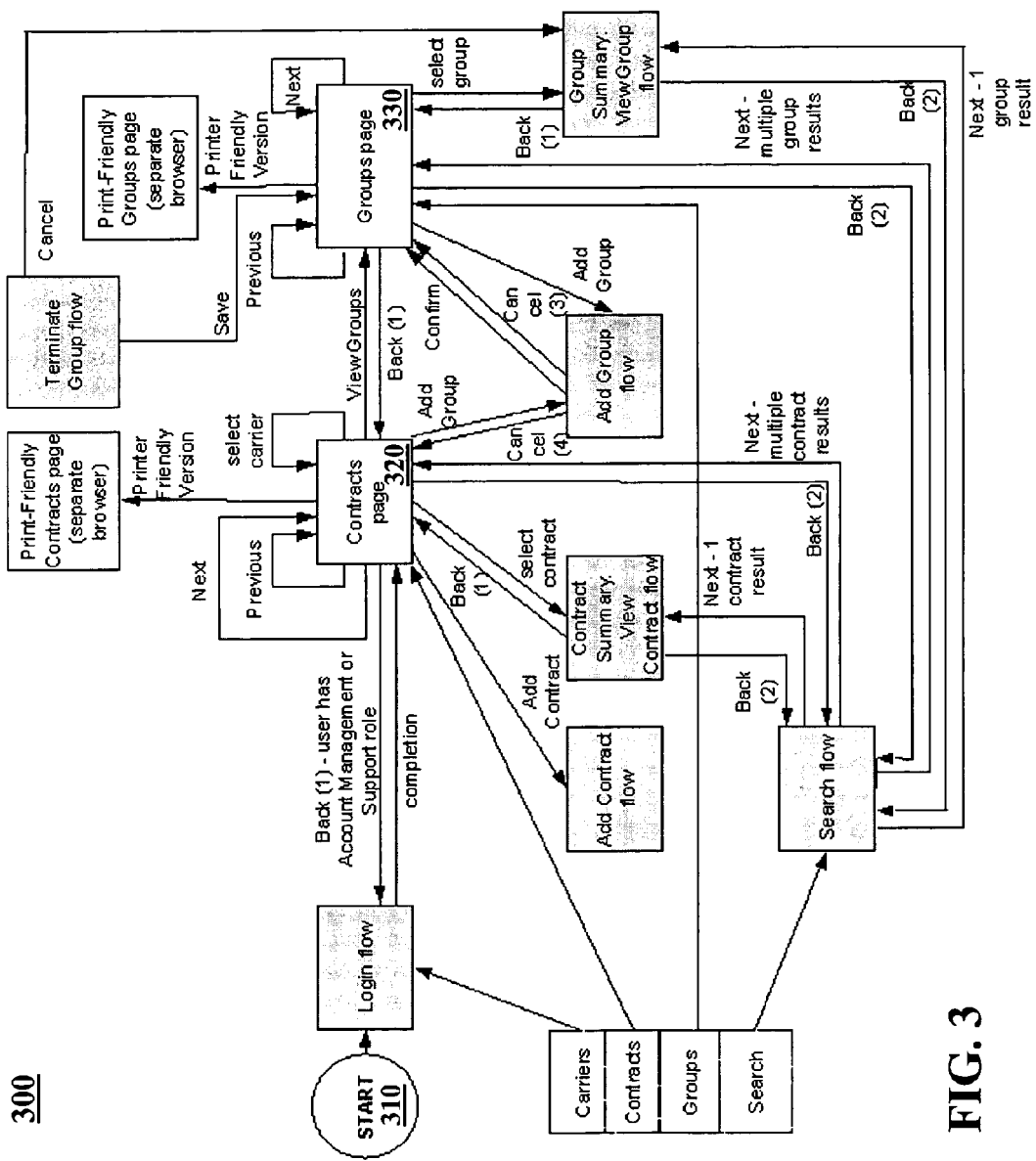
FIG. 3 is an illustrative flow diagram that demonstrates the transmission of data throughout an illustrative prescription drug management system in accordance with some embodiments of the present invention.

Turning now to FIG. 3, a block diagram is shown for illustrating a menu hierarchy and processes of a prescription benefits management system in accordance with some embodiments of the present invention. The prescription benefits management system is designed to provide users with the ability to efficiently and conveniently manage and implement a prescription benefits management application. This includes, for example, allowing the user to browse information relating to the contract, information relating to the group members, browse coverage information, input broker information, input billing information, select a pharmacy network, select pricing options for the prescription plan, create a customized prescription plan, input brand/generic difference overrides, and/or generating summary documents. The prescription benefits management application may be accessed by various users including, but not limited to, patients, clients (e.g., employers, healthcare providers, etc.), administrators, pharmacists, and physicians in order to obtain and review information regarding prescription benefits and coverage information.

As shown in FIG. 3, the prescription benefits management application provides the user with a menu 310 that allows the user to access various information and perform tasks necessary to manage prescription benefits and coverage information. For example, contracts page 320 may provide the user with the opportunity to maintain and/or manage one or more contracts (e.g., add a contract, view a contract summary, modify a contract, etc.). In another example, groups page 330 may provide the user with the opportunity to maintain and manage one or more groups (e.g., add a new group, view a group summary, modify a group, select a pharmacy network, select pricing options for the prescription plan, create a customized prescription plan, and/or input brand/generic difference overrides).

In some embodiments, the prescription benefits management application provides users with an initial login. The login may be used, for example, to request a user name and password. The login may be used to verify that the user is authorized to access the prescription benefits management application. In some embodiments, the login may be used to automatically establish access rights for particular users. For example, a benefits administrator may have the authority to change, modify, or create information stored on the prescription benefits management application. In another example, a client accessing the prescription benefits management application may have the authority to view information relating to the client's contract.

In some embodiments, the prescription benefits management application allows a user to add a contract (e.g., client) to their existing carrier or healthcare provider, add groups to an existing plan design and contract, and/or modify an existing group's plan design. The user may perform one of these functions by, for example, accessing a home page (e.g., the Benefit Services home page) and selecting the appropriate button (e.g., "I Want To . . . Add Groups or Benefit Changes") using any suitable user input device (e.g., user input device 206 of FIG. 2). In response to the user entering the updated information, the prescription benefits management application may process the user's updated prescription benefit and coverage information and update the prescription benefits management application in a predetermined amount of time (e.g., within 48 to 72 hours).

Figure 4:
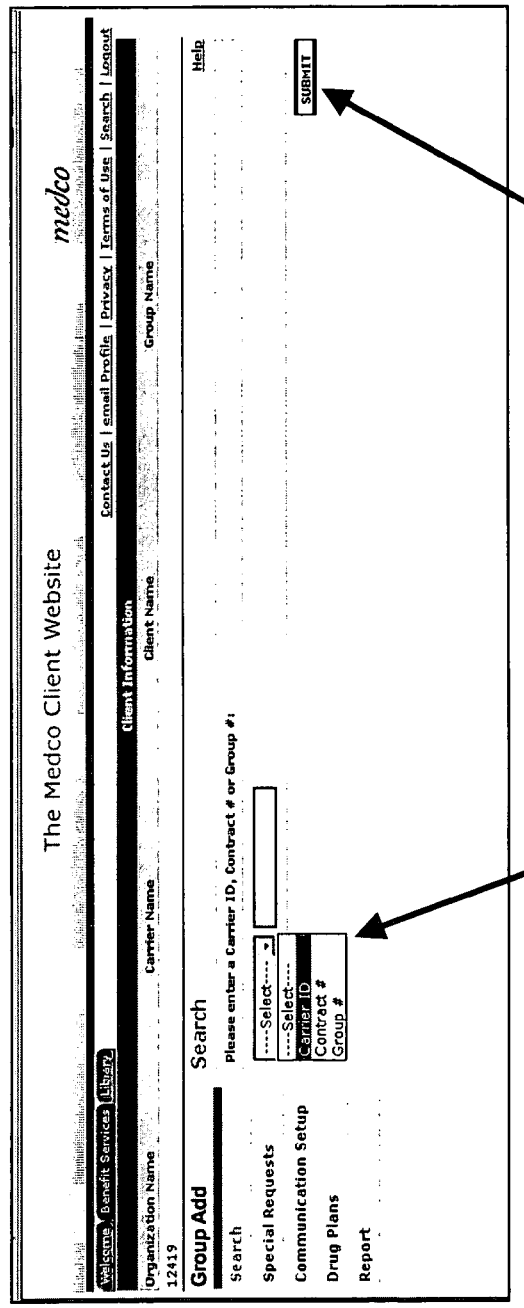
FIG. 4 is an illustrative search screen that may be provided by the prescription benefits management application in accordance with some embodiments of the present invention.

In response to the user accessing the home page and selecting the "I Want To . . . Add Groups or Benefit Changes" button, the prescription benefits management application may provide the user with an illustrative search screen 400 (FIG. 4). As shown, screen 400 of FIG. 4 is designed to be provided on a computer display (e.g., display 204 of workstation 102 or display 222 of server 110 of FIGS. 1 and 2). However, it should be noted that the format and contents of the screens that follow may be modified to accommodate different platforms, if desired. It should also be noted that some, all, or alternatives to the following screens may be provided to a user of the prescription benefits management application in accordance with the present invention.

Illustrative search screen 400 of FIG. 4 provides a user with the ability to perform a number of searches. As shown in FIG. 4, the user may perform a search request based on a Carrier ID, Contract #, and a Group #. In response to the user inputting a carrier number, a contract number, a group number, and/or any other suitable information for identifying one or more prescription benefit plans, the prescription benefits management application provides the user with the corresponding search results. For example, in response to the user inputting a Carrier ID into a search field 410 and selecting a "Submit" button 420, the prescription benefits management application may perform the search and provide the user a list of clients corresponding to the Carrier ID. Alternatively, the user may be provided with a client summary page (e.g., in response to inputting a contract number) or a group summary page (e.g., in response to inputting a group number). It should be noted that any other suitable interface element (such as a menu selection, link, option, or other interface element) or suitable searching paradigm may also be used.

Figure 5:
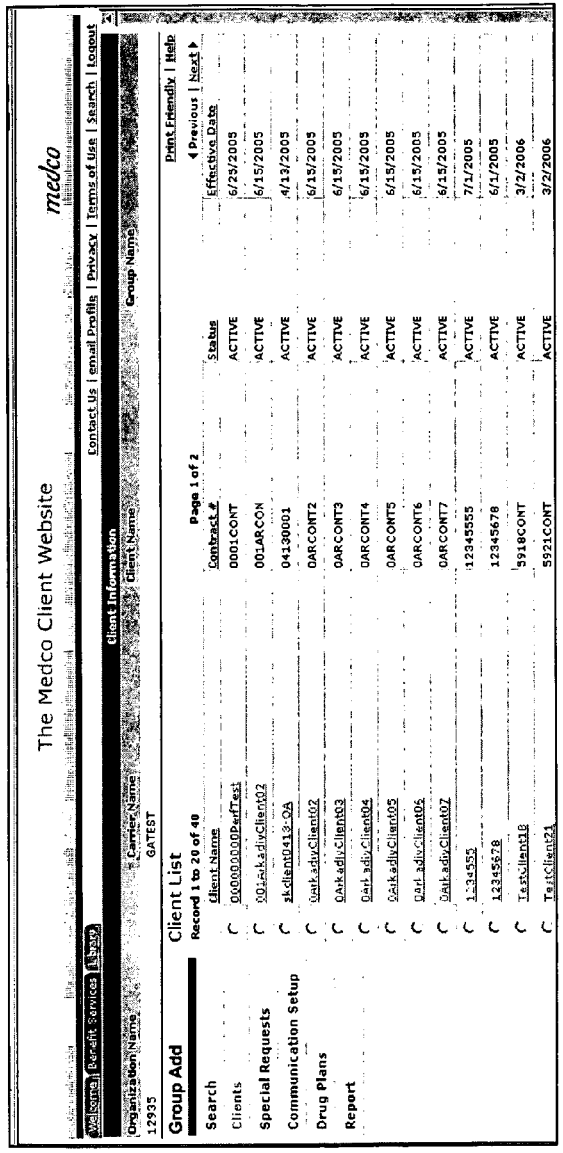
FIG. 5 is an illustrative search results screen that may be provided by the prescription benefits management application in accordance with some embodiments of the present invention.

An example of an illustrative search results screen 500 is shown in FIG. 5. Based at least in part on the user's access rights, the prescription benefits management application may provide the user with, for example, a list of client names and their associated contract number, status, and effective date. Using any suitable interface element, the user may select one of the search results from screen 500. In response to selecting one of the search results, the prescription benefits management application may provide the user with access to additional information relating to the corresponding client, such as a contract number, status of the client, address information, billing information, plan details, comments from the healthcare provider, or any other suitable information. The additional information may include any suitable content, such as text, graphics, video, audio, animations, or any other suitable content.

In some embodiments, the prescription benefits management application may allow the user to add a client or a contract to the existing carrier. Using the prescription benefits management application, the user may add the new client name and primary information, add broker involvement and contact information, setup billing information (e.g., provide information relating to responsibility for paying the prescription benefits manager, administrator and/or sponsor).

Figure 6:
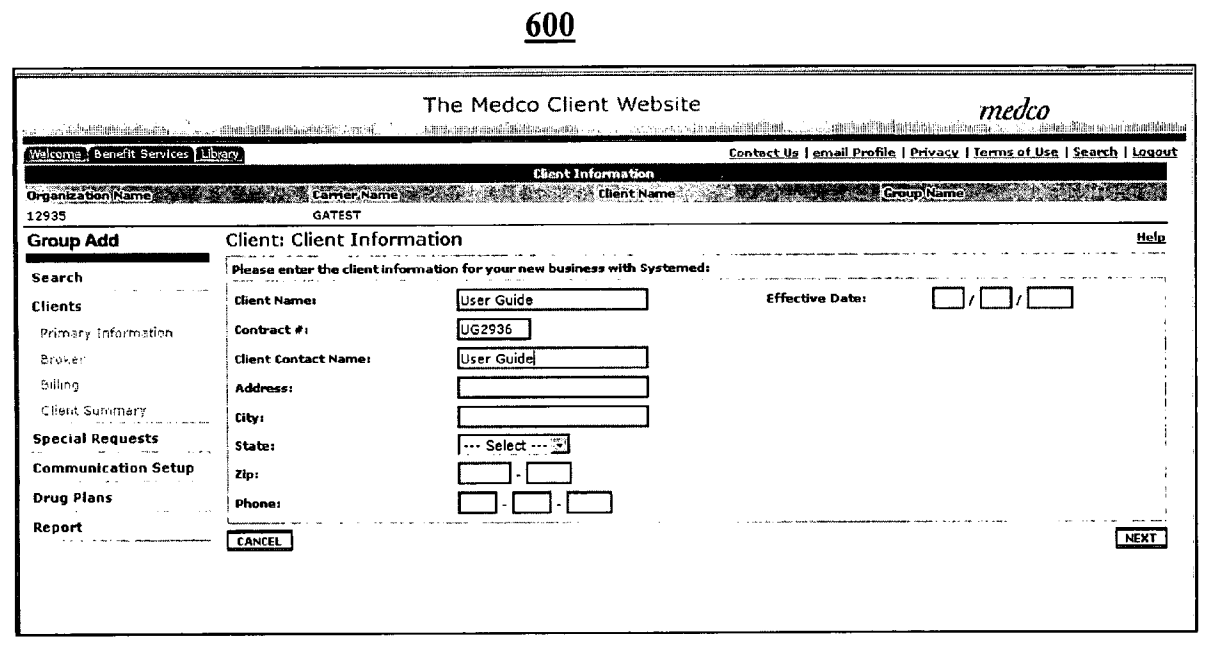

In response to the user selecting an "Add Client" button, the prescription benefits management application may provide the user with a client content information screen 600 as shown in FIG. 6. As shown in FIG. 6, the user is provided with input fields and drop-down lists to enter client contact information (e.g., client name, contract number, client contact name, address information, etc.). It should be noted that the user may be required to enter a contract number that has not been assigned in the prescription benefits management application. Alternatively, the prescription benefits management application may provide the user with an error message in response to the user entering a contract number that is not unique.

In response to the user entering the client contact information and selecting a "Next" button, the prescription benefits management application allows the user to indicate whether the new client has a relationship with a broker. For example, if a commission should be paid to a broker by the healthcare provider or benefits manager, the prescription benefits management application allows the user to indicate the user's involvement with the broker (e.g., by selecting "Yes" from a broker involvement screen 700 of FIG. 7 and entering information relating to the broker in broker information screen 800 of FIG. 8).

In some embodiments, the broker may be provided with access to the prescription benefits management application. When the broker administers the member eligibility, the broker administrator will have the same access as the Third Party Administrator and Health Plan provider.

Figure 9:
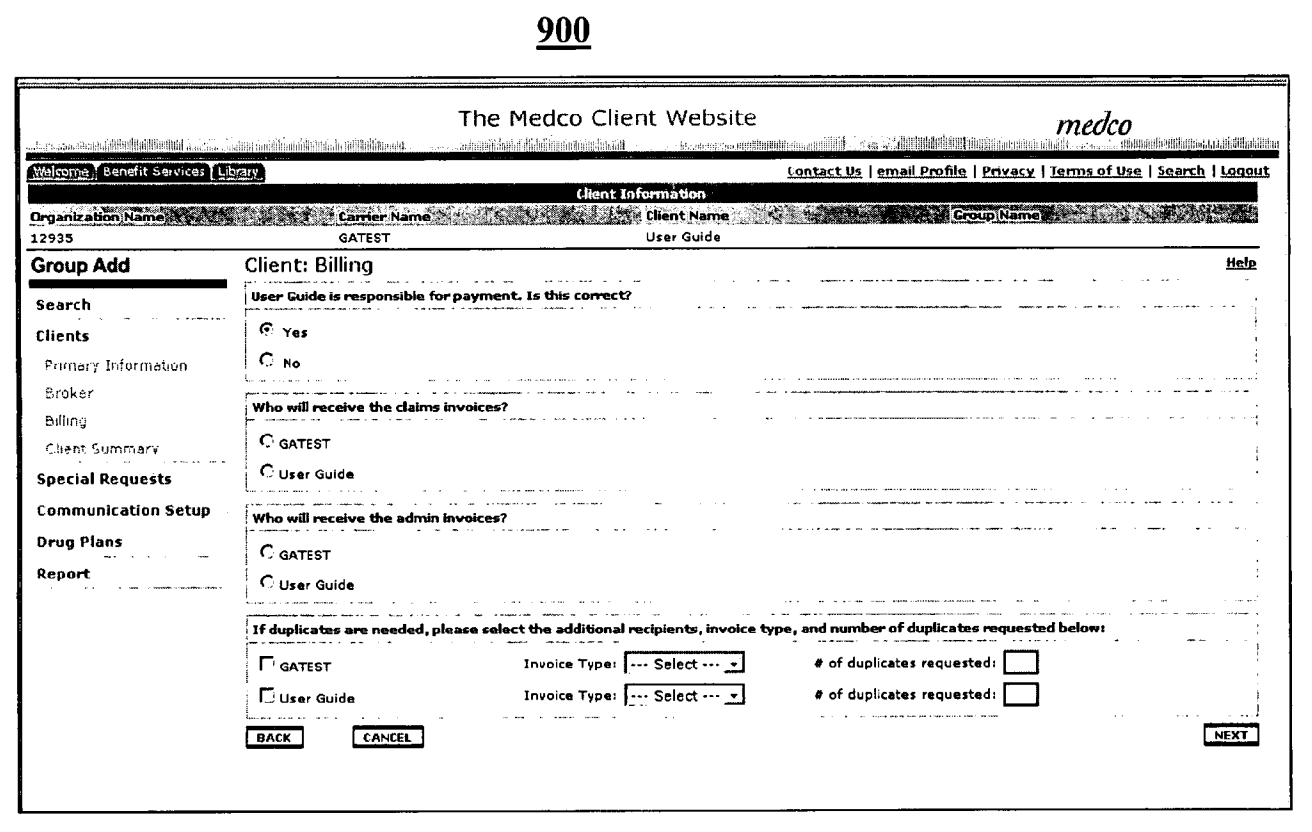

In some embodiments, the prescription benefits management application may allow the user to enter billing information (e.g., indicate the entity responsible to pay for claims under the new contract). As shown in FIG. 9, the prescription benefits management application may provide the user with a billing information screen 900. Using the information entered in screen 900, the prescription benefits management application may send the user and/or any other suitable entity a printed or electronic (e.g., via e-mail) invoice. In some embodiments, the prescription benefits management application may populate one or more of the fields in screen 900 based on the user's information (e.g., carrier number, the user's company information, etc.). However, any other suitable approach may also be used, such as, for example, the prescription benefits management application may provide the user with a table of clients and/or carriers and their respective information.

Figure 10:
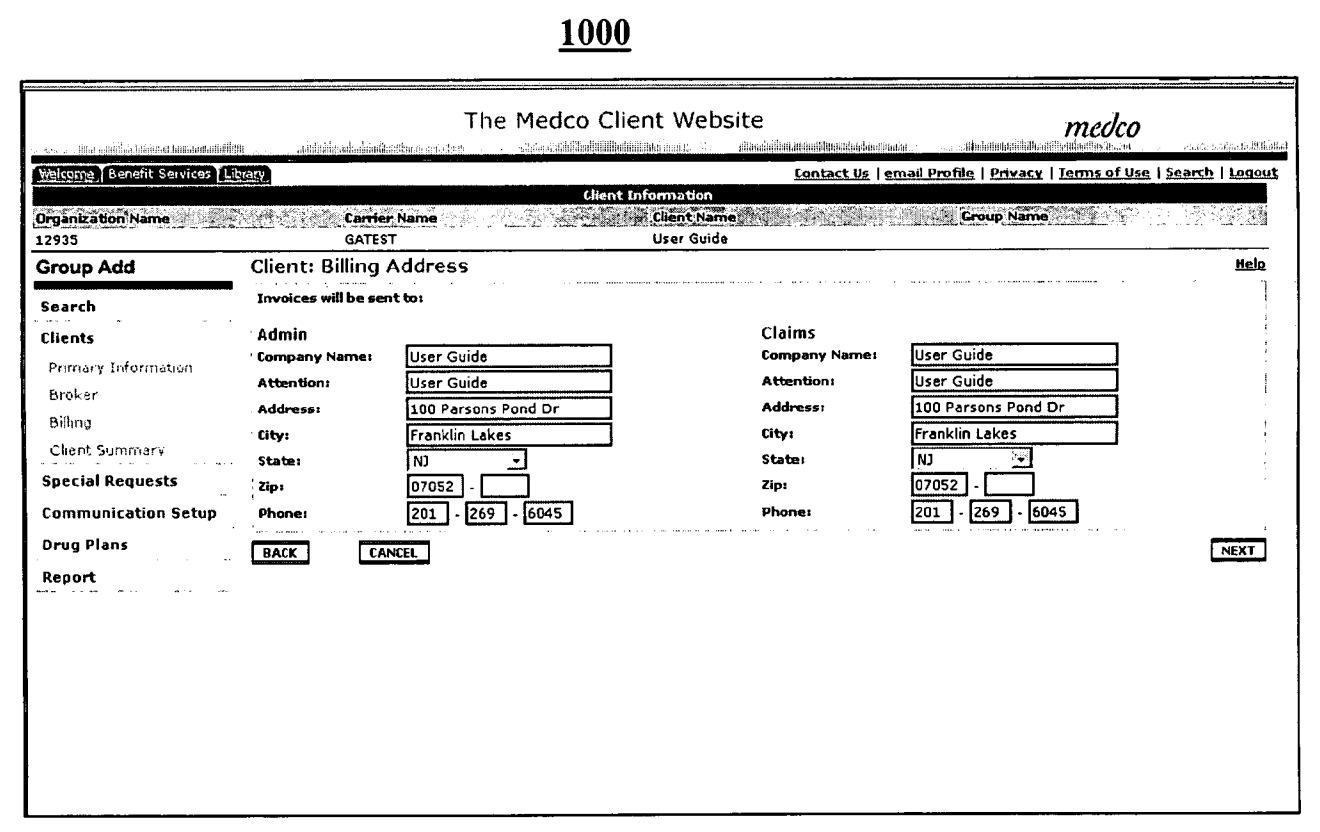

In response to the user entering information into billing information screen 900, the prescription benefits management application may allow the user to input billing address information using billing address screen 1000 of FIG. 10. Alternatively, the prescription benefits management application may populate one or more of the fields in screen 1000 based on the user's information.

Figure 11:
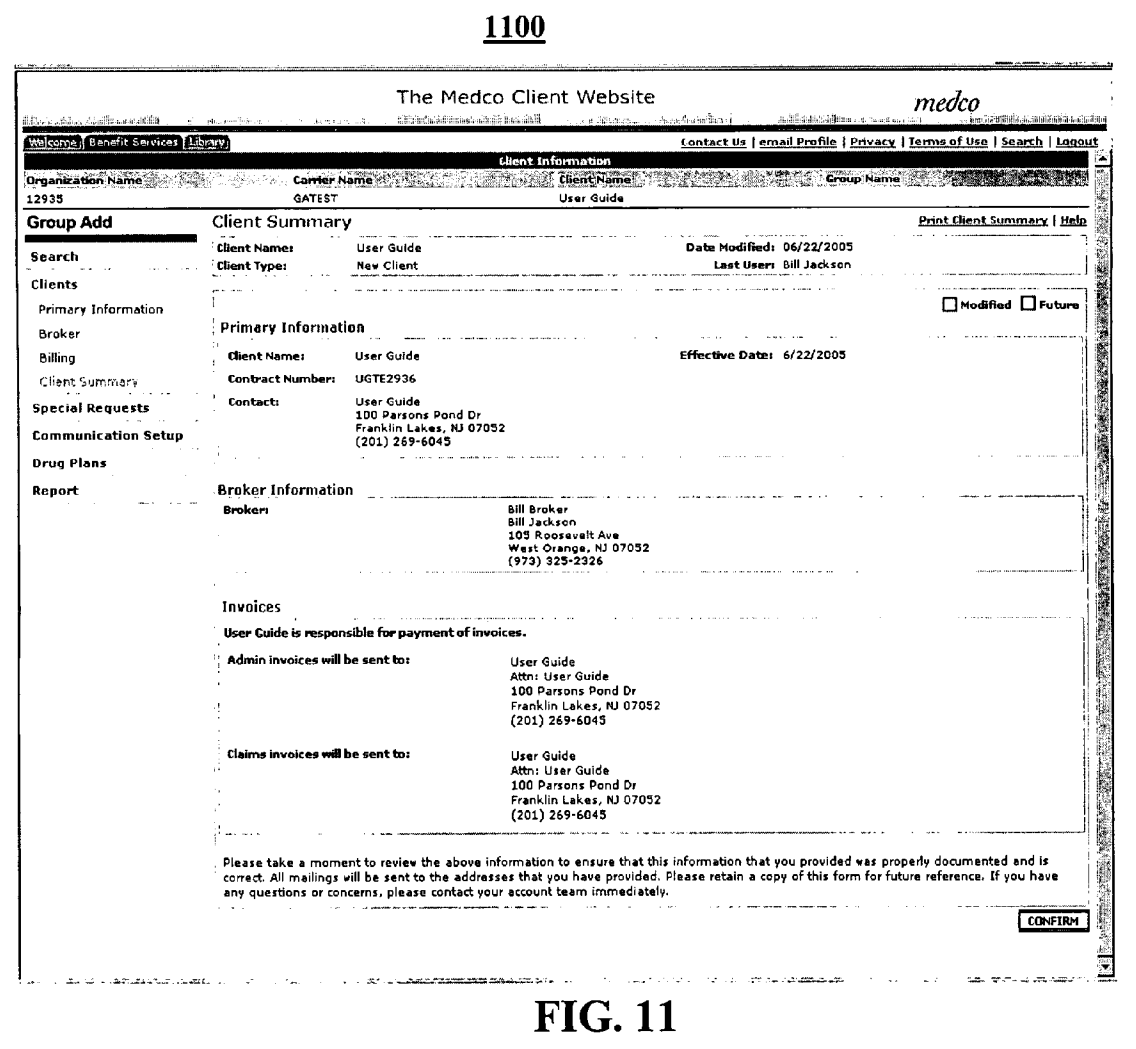

As shown in FIG. 11, when the user has completed entering the information relating to the new client, the prescription benefits management application may automatically generate a client summary screen 1100. Screen 1100 may include, for example, a detailed summary of the previous selections and inputs made by the user. Screen 1100 may also request that the user review the information in screen 1100 and confirm the addition of the new client. In response to the user selecting a "Confirm" button (or any other suitable interface element), the prescription benefits management application may provide the user with a confirmation message (e.g., via e-mail, on-screen, etc.).

In response to the user adding a new client, the prescription benefits management application may automatically process the received request and information relating to the new client and update the prescription benefits management application within a predetermined time (e.g., real-time, 24 hours, 48 hours, etc.). For example, a client or an employee under the added contract may attempt to fill a prescription at a local pharmacy after the predetermined time.

For example, a pharmacist or other authorized user may access the client's information using the prescription benefits management application. The prescription benefits management application may allow the pharmacist to input the prescription the client is requesting. In response, the prescription benefits management application may determine whether the prescription is covered under the client's drug plan. In addition, the healthcare provider may track the medication prescribed to a client.

In some embodiments, the prescription benefits management application may also allow the user to add and/or maintain a new group to an existing plan. Using the prescription benefits management application, the user may, for example, add a group name, select a program type, pharmacy network, and pricing options for the group, setup member co-payments/co-insurance, setup brand/generic difference overrides, add a deductible, CAP (maximum benefit allowed), and/or a OOP (the maximum benefit that a client is required to pay out of pocket), select a drug plan for the group, setup dependent coverage, and/or perform any other suitable function relating to the group.

In some embodiments, the prescription benefits management application may provide audit reports that allow the user to verify recent changes made to the benefit plan and the user or entity that requested the change.

Figure 13:
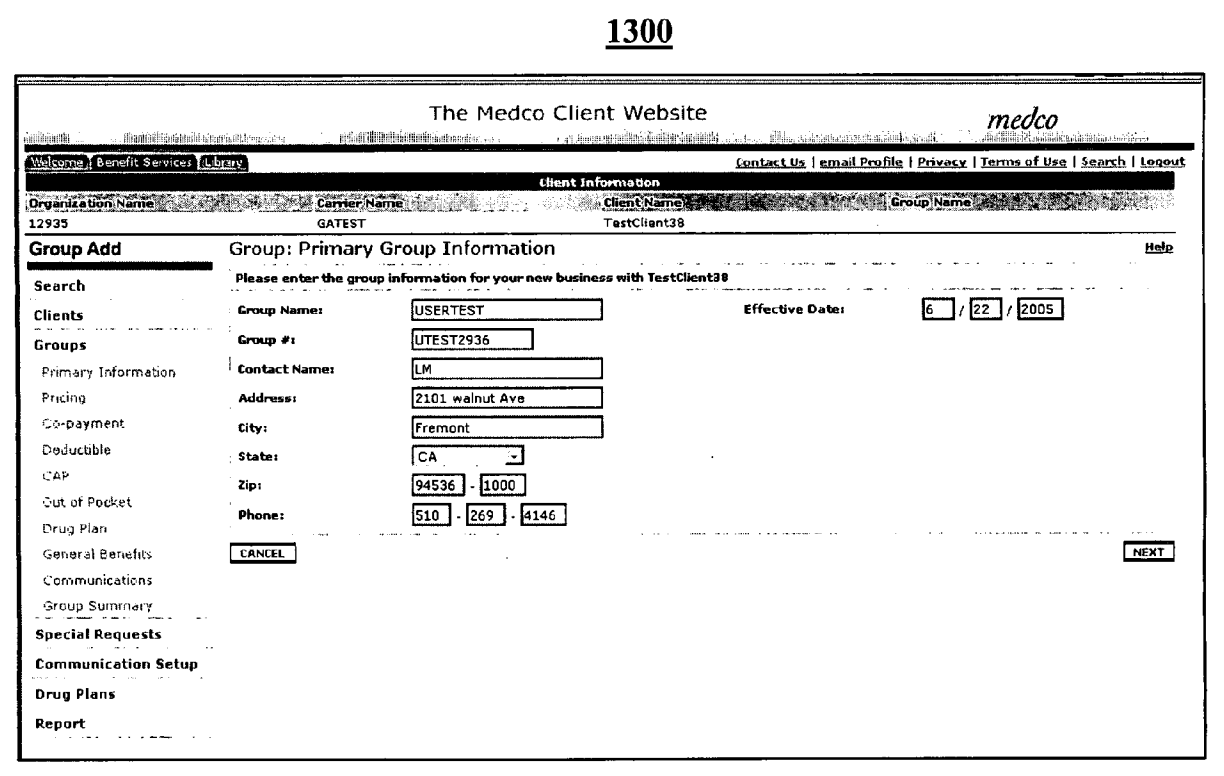

As shown in FIG. 12, the prescription benefits management application provides the user with an illustrative client list screen 1200. In response to the user selecting a client in screen 1200 and selecting "Add Group" button 1210, the prescription benefits management application allows the user to add a new group to an existing client. The prescription benefits management application may provide the user with a group information screen 1300 as shown in FIG. 13. As shown in FIG. 13, the user is provided with input fields and drop-down lists to enter group information (e.g., client name, contract number, client contact name, address information, etc.) for new business with the client (e.g., TestClient38). It should be noted that the user may be required to enter a contract number that has not been assigned in the prescription benefits management application. Alternatively, the prescription benefits management application may provide the user with an error message in response to the user entering a contract number that is not unique.

Figure 14:
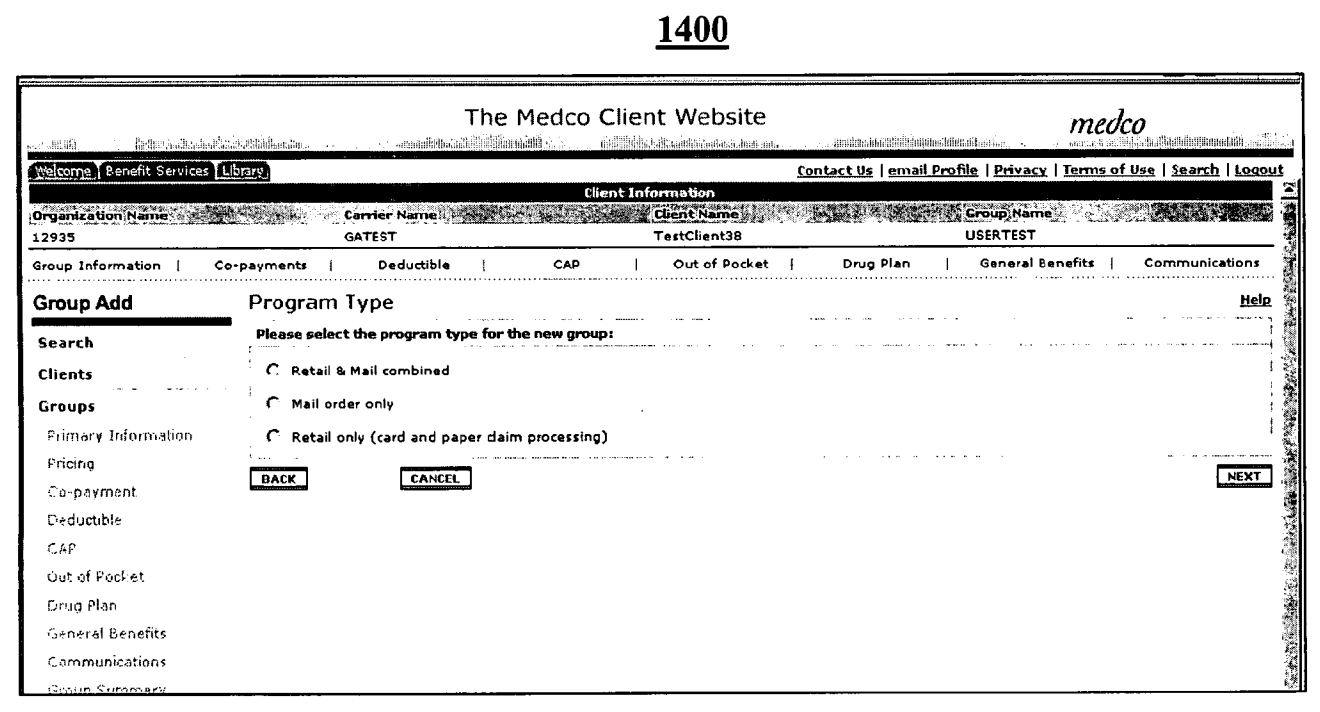

FIG. 14 is an illustrative program selection screen 1400 that may be provided by the prescription benefits management application in accordance with some embodiments of the present invention. Using screen 1400, the prescription benefits management application may provide the user with the opportunity to select the type of program to be applied to the newly added group. As shown in FIG. 14, the user may select between the programs of "Retail & Mall combined," "Mall order only," and/or "Retail only." The type of program selected by the user may determine the pricing of the group's members' prescription at the point of sale by distribution channel.

Figure 15:
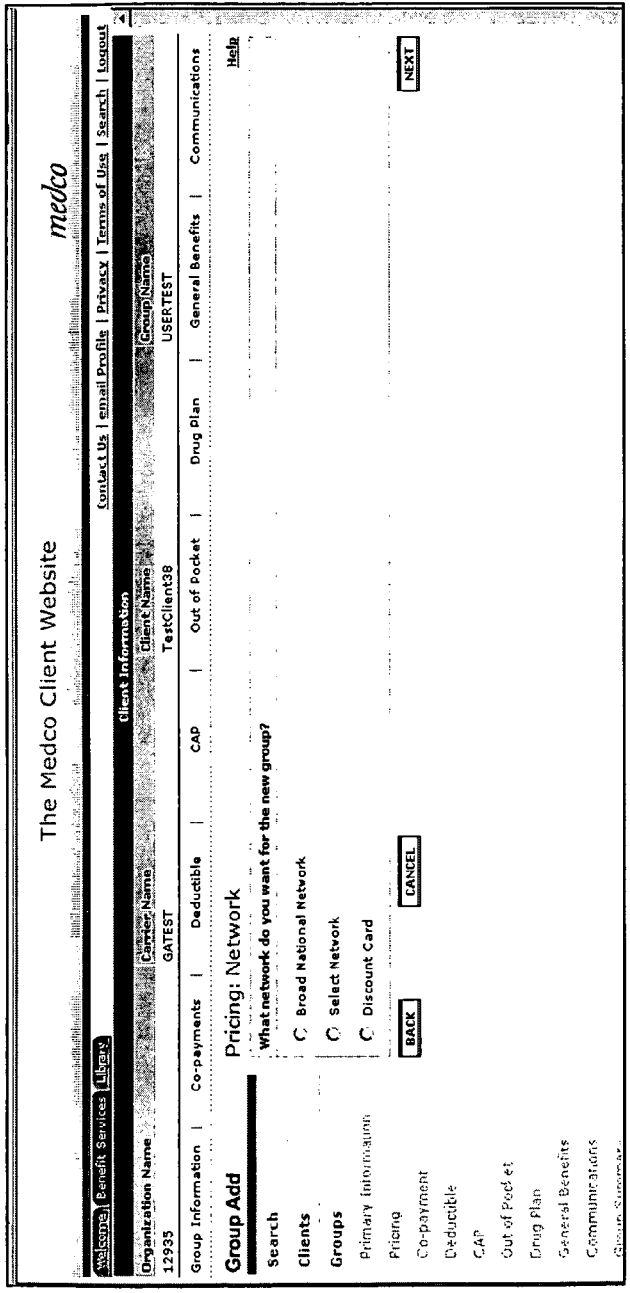
FIG. 15 is an illustrative pricing network screen that may be provided by the prescription benefits management application in accordance with some embodiments of the present invention.

FIG. 15 is an illustrative pricing network screen 1500 that may be provided by the prescription benefits management application in accordance with some embodiments of the present invention. Using screen 1500, the prescription benefits management application may provide the user with the opportunity to select the type of network to be applied to the newly added group. As shown in FIG. 15, the user may select between the networks of "Broad National Network," "Select Network," or "Discount Card." The type of network selected by the user may define the level of participation (e.g., number of pharmacies) that the group's members' prescription benefit is valid.

Figure 16:
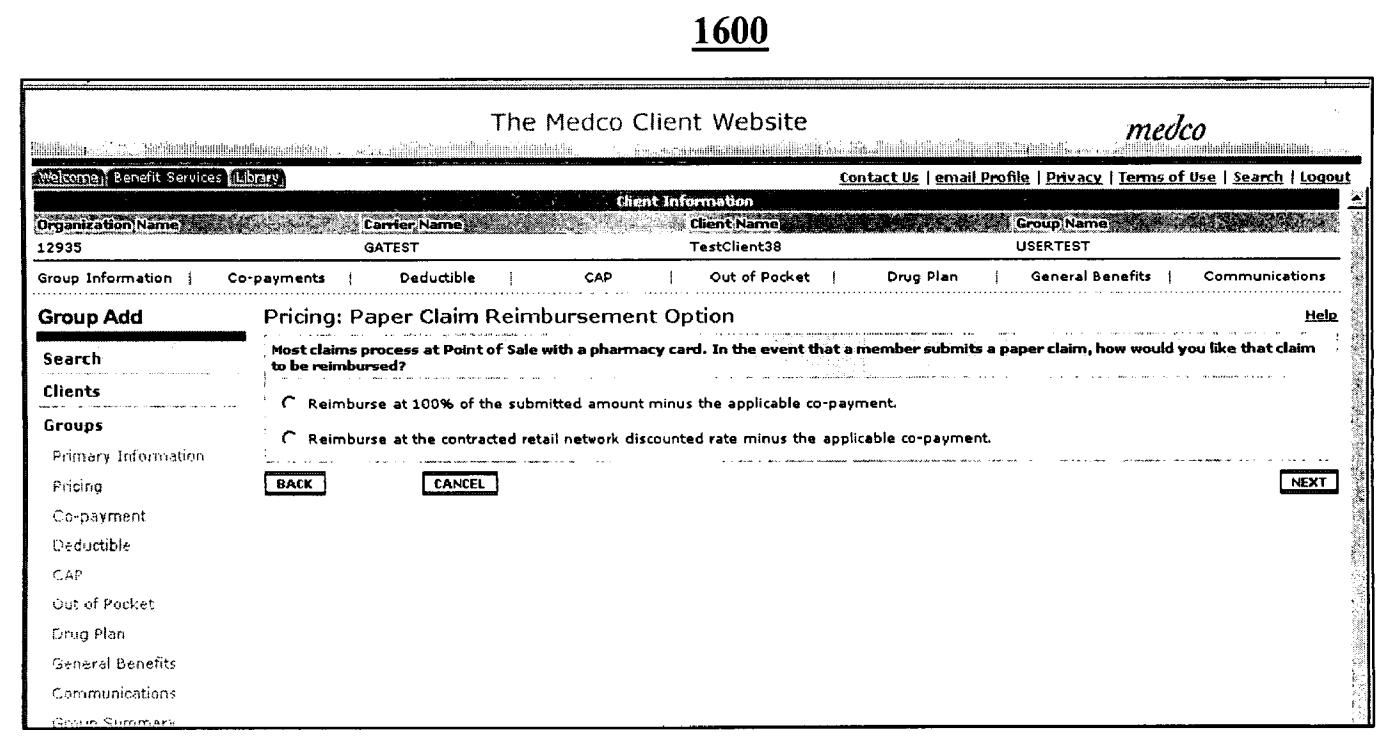

FIG. 16 is an illustrative reimbursement option screen 1600 that may be provided by the prescription benefits management application in accordance with some embodiments of the present invention. Using screen 1600, the prescription benefits management application may provide the user with the opportunity to select how the plan should reimburse group members. For example, as shown in FIG. 16, the user may select how members who have filled a prescription without a pharmacy card or any other suitable card and are submitting a paper claim for reimbursement. Alternatively, the user may provide the member with an agreed-upon discounted rate regardless of whether the member presents a pharmacy card.

Figure 17:
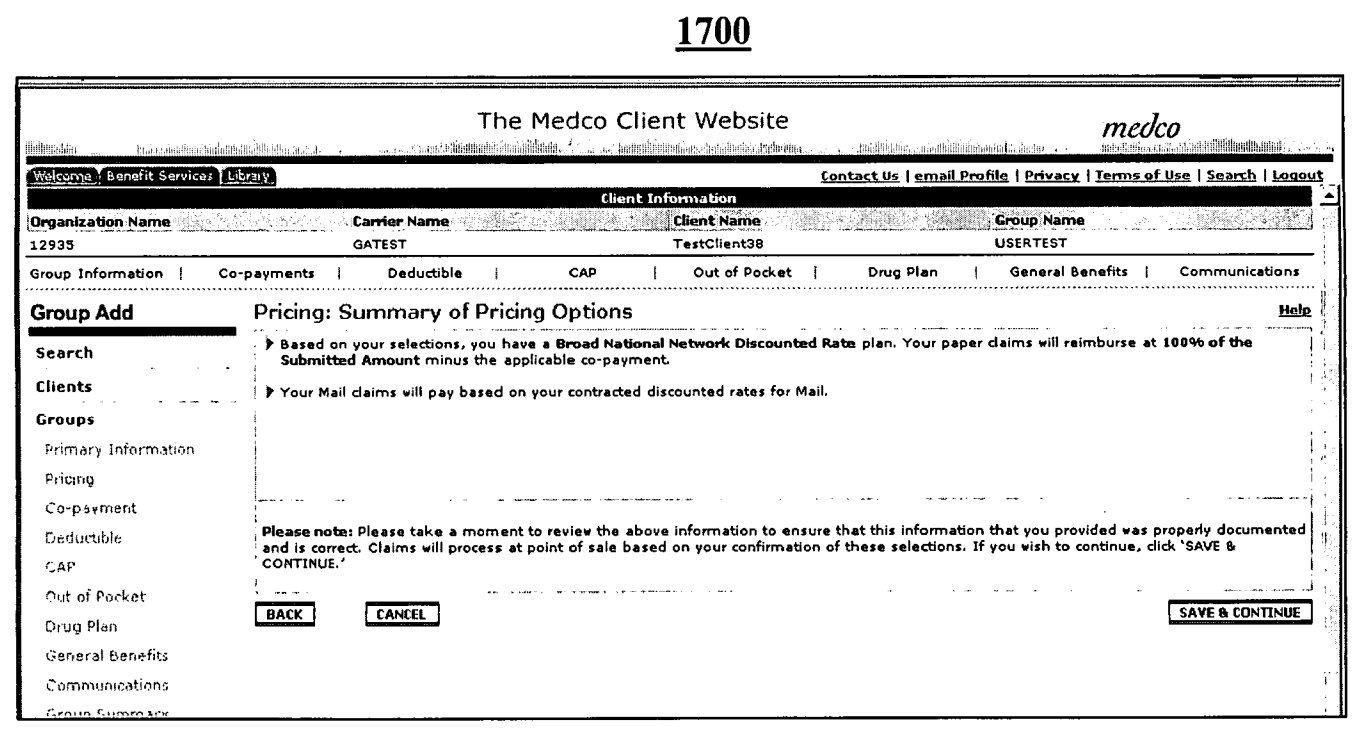

FIG. 17 is an illustrative pricing option summary screen 1700 that may be provided by the prescription benefits management application in accordance with some embodiments of the present invention. As shown in FIG. 17, when the user has completed entering the pricing information relating to the new group, the prescription benefits management application may automatically generate summary screen 1700. Screen 1700 may include, for example, a detailed summary of the previous selections and inputs made by the user. Screen 1700 may also request that the user review the information in screen 1700 and confirm the addition of the pricing information for the new group.

FIGS. 18-24 are illustrative co-payment screens that may be provided by the prescription benefits management application in accordance with some embodiments of the present invention. Using these co-payment screens, the prescription benefits management application provides the user with options for setting up the co-payment program for the group.

Figure 18:
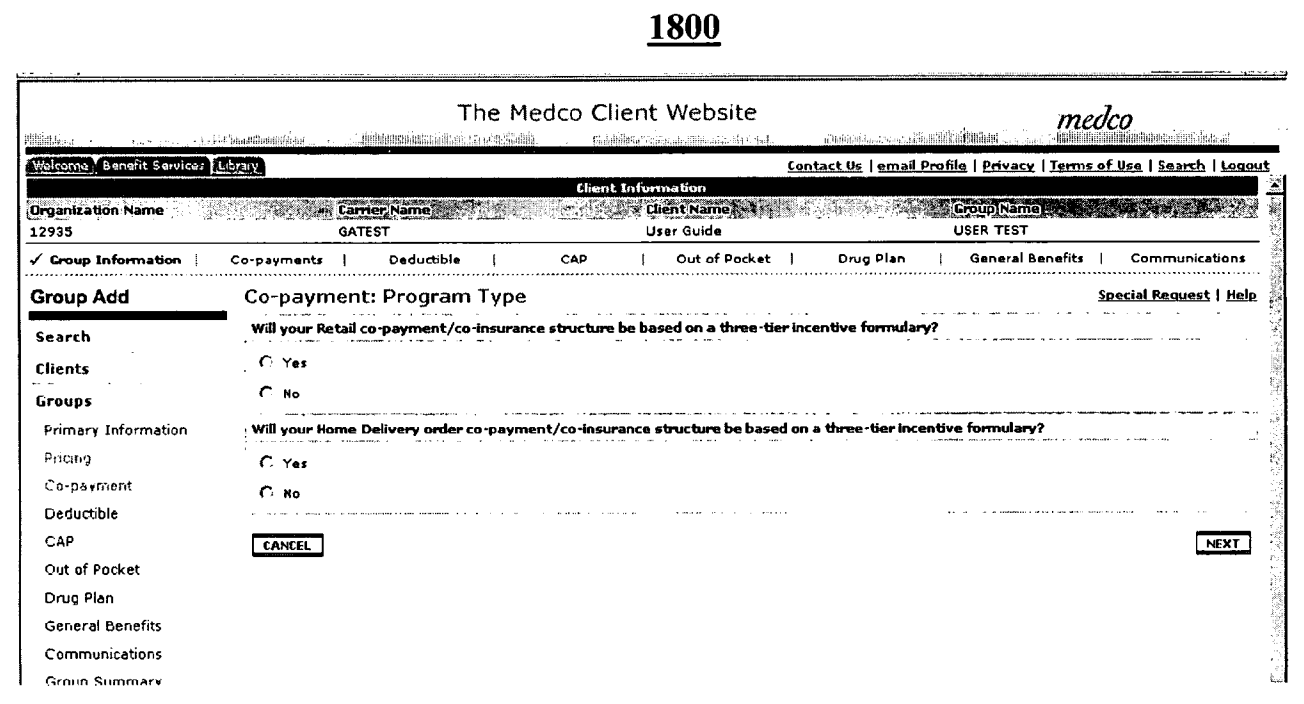

FIG. 18 is an illustrative co-payment program type screen 1800 that may be provided by the prescription benefits management application in accordance with some embodiments of the present invention. Using screen 1800, the prescription benefits management application may allow the user to select the co-payment program type. For example, screen 1800 prompts the user with questions as to whether or not the co-payment or co-insurance structure for mail order and retail prescriptions are to be based on a three-tier incentive formulary by distribution channel (e.g., mail order, retail).

Figure 19:
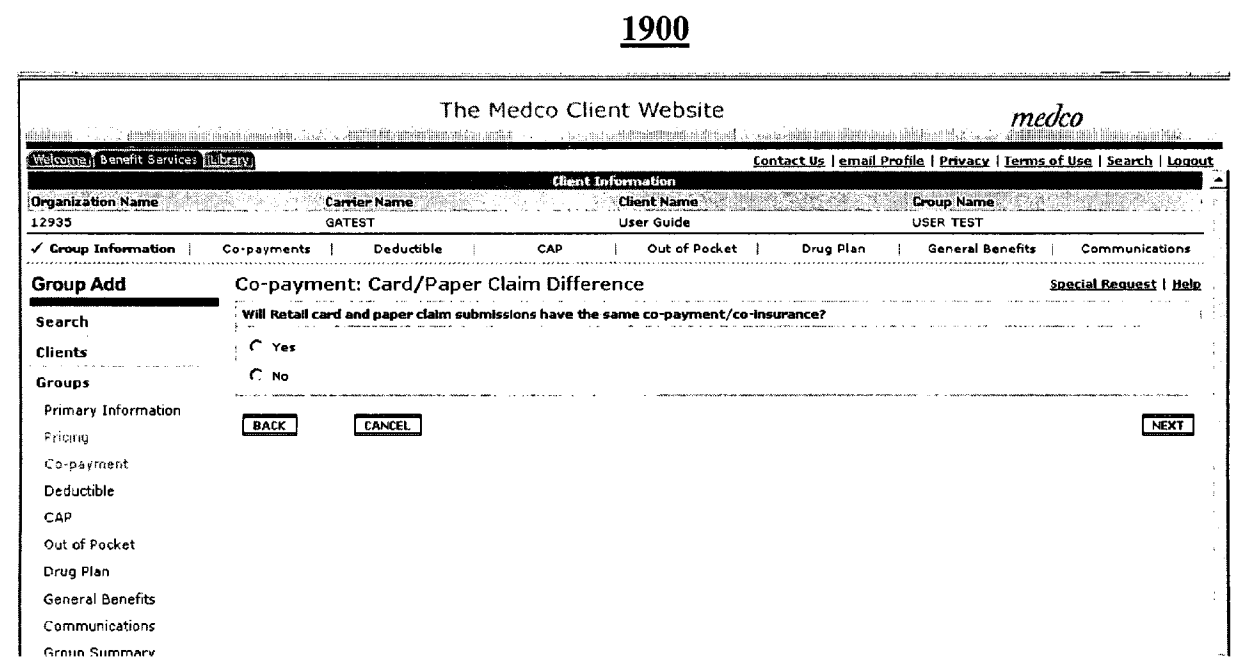

FIG. 19 is an illustrative co-payment claim different screen 1900 that may be provided by the prescription benefits management application in accordance with some embodiments of the present invention. Using screen 1900, the prescription benefits management application may allow the user to indicate differences between submitted claims. For example, screen 1900 prompts the user to answer whether or not the co-payment or co-insurance is the same at retail for prescription purchased using a pharmacy card as opposed to prescriptions that are purchased out-of-pocket and requested for reimbursement by a paper claim.

Figure 20:
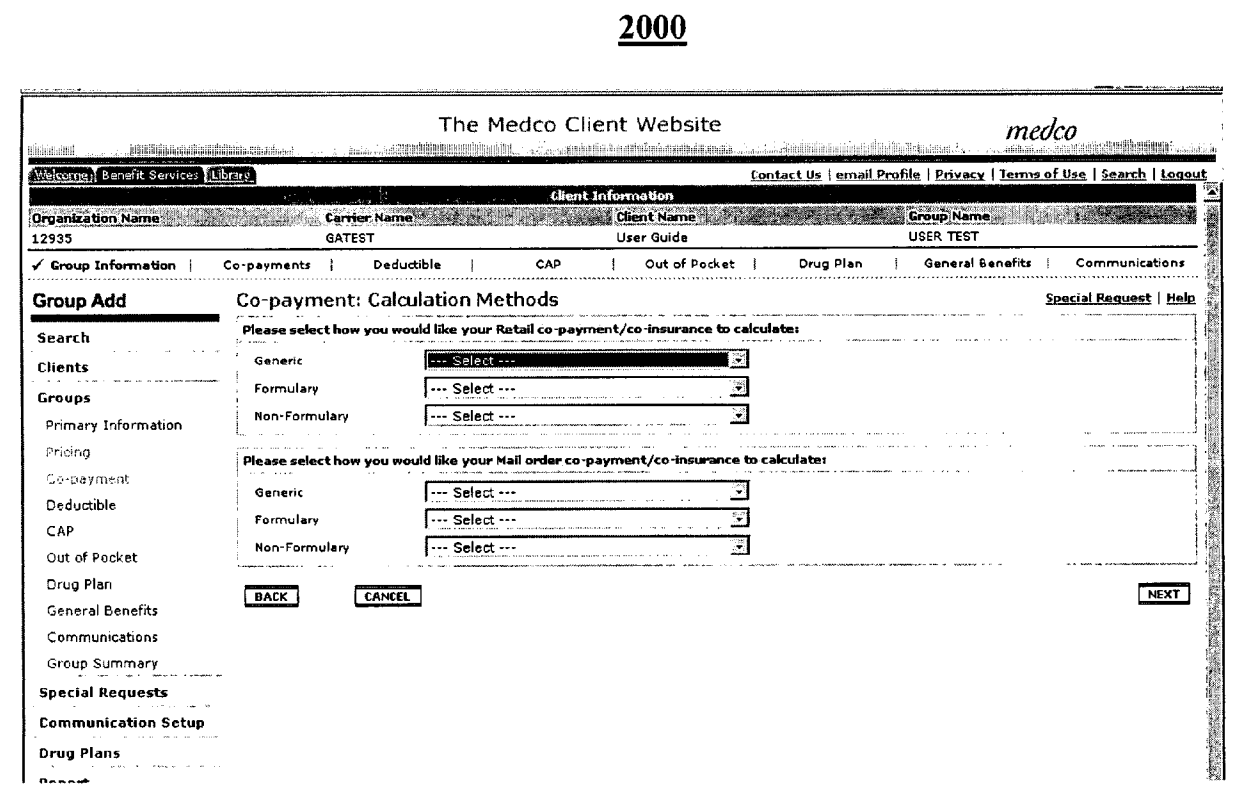
Figure 21:
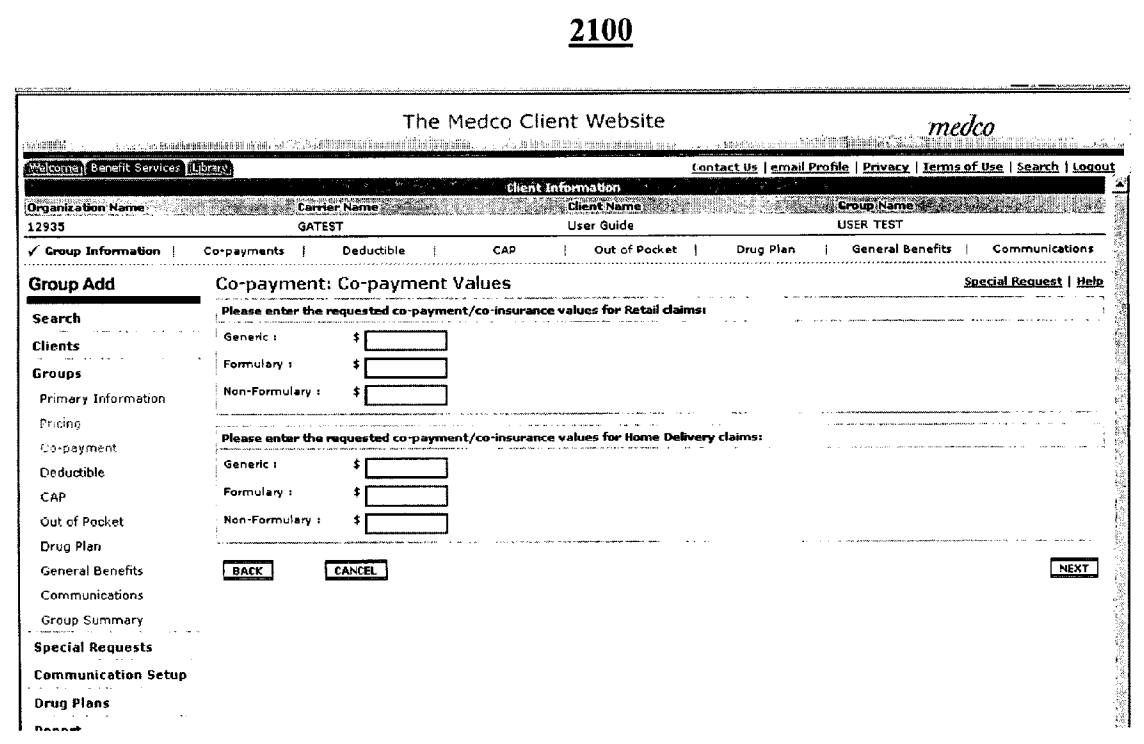

FIG. 20 is an illustrative co-payment calculation screen 2000 that may be provided by the prescription benefits management application in accordance with some embodiments of the present invention. Screen 2000 allows the user to select a co-payment or co-insurance calculation method. For example, if the prescription is purchased using a mail order, the user may select that the co-payment for generic drugs is calculated by a flat dollar amount plus a percentage of the cost of the generic drug. Alternatively, a percent format with or without a maximum allowance may be used to calculate the cost of the co-payment or co-insurance. As shown in FIG. 21, the prescription benefits management application provides the user with an illustrative co-payment values screen 2100. Screen 2100 allows the user to enter co-payment or co-insurance values that will be applied using the selected calculation method (e.g., flat dollar amount).

Figure 22:
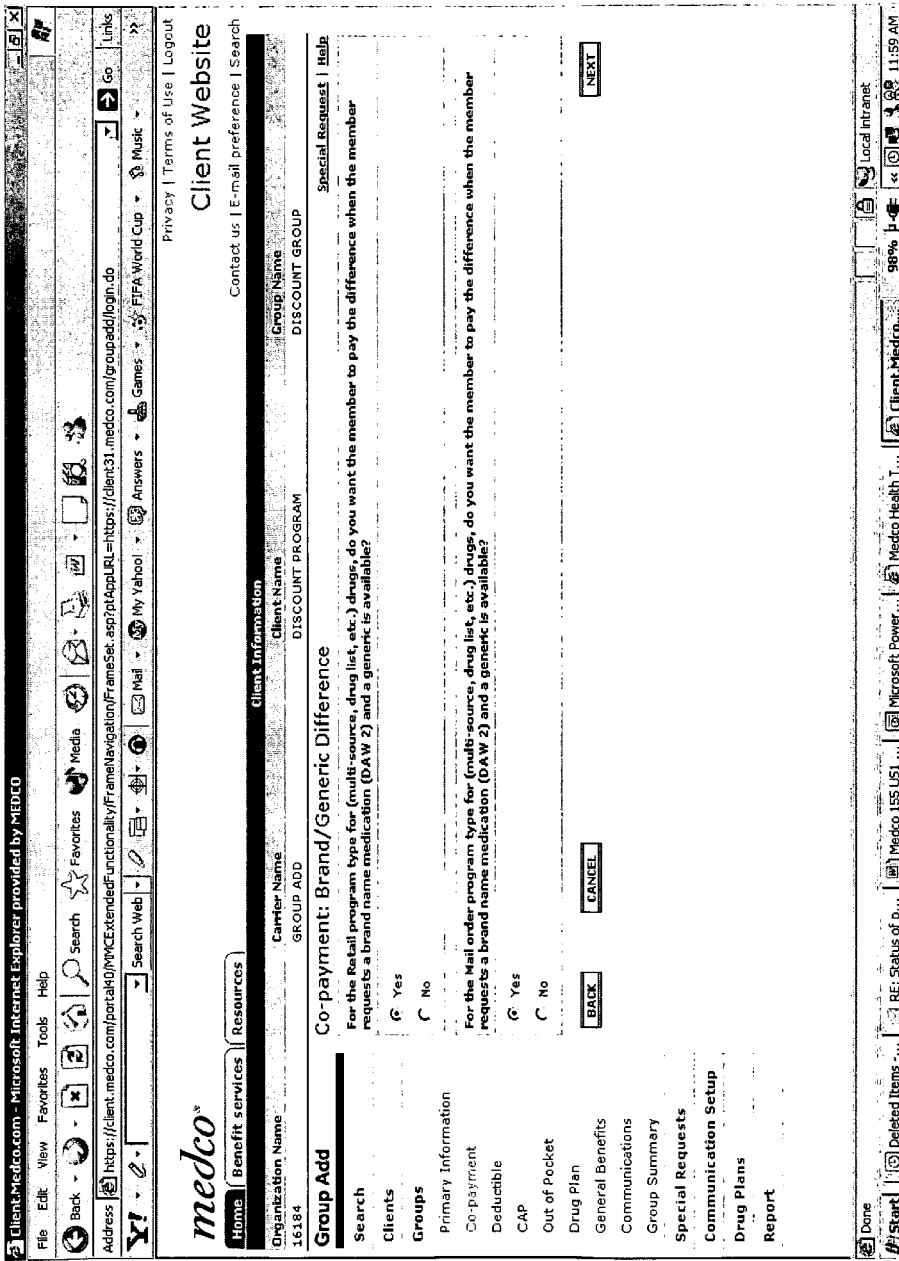
FIGS. 22 and 23 are illustrative Dispense as Written (DAW) physician override prescription instruction information screens that may be provided by the prescription benefits management application in accordance with some embodiments of the present invention.
Figure 24:
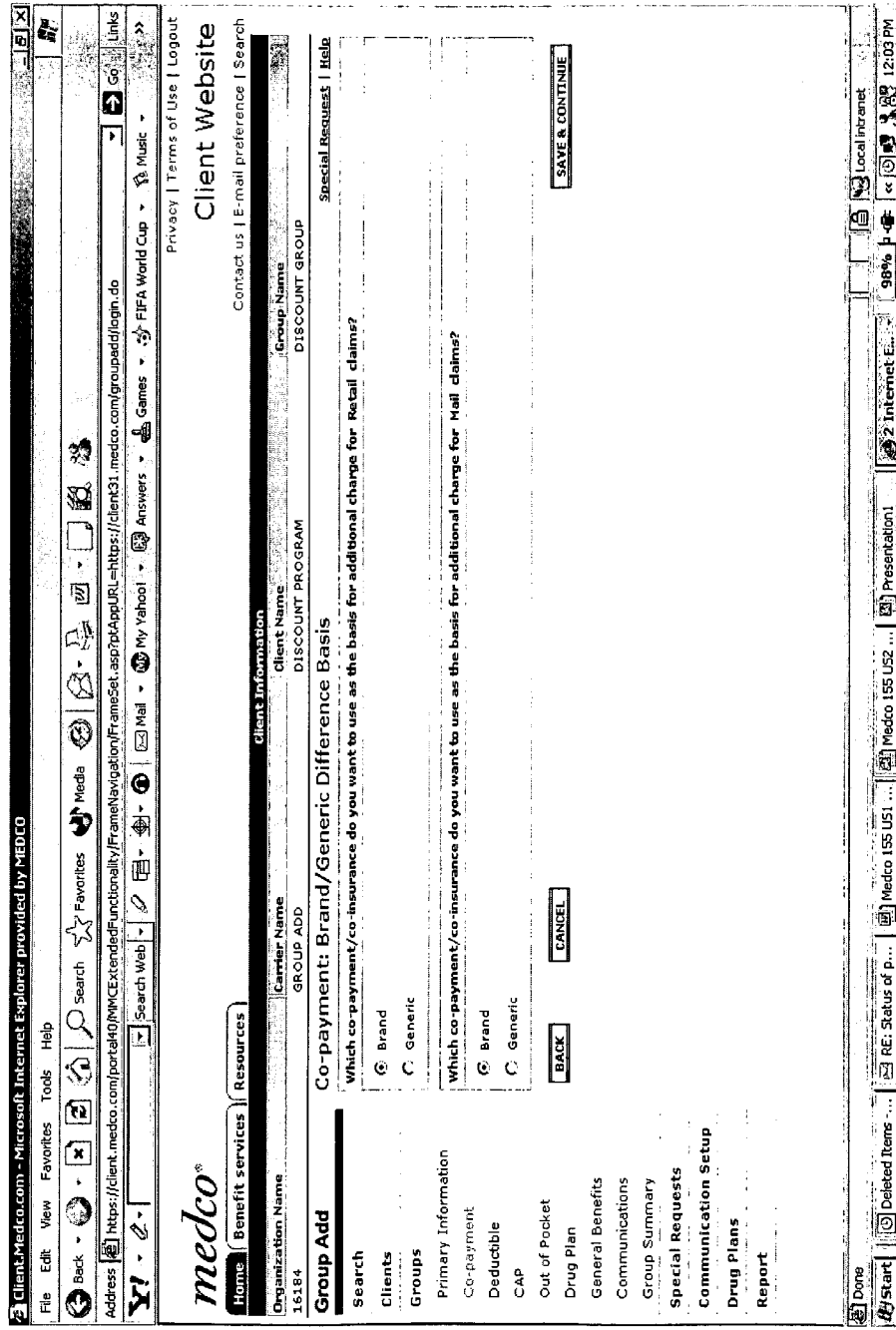
FIG. 24 is an illustrative co-payment calculation screen based DAW physician override selections that may be provided by the prescription benefits management application in accordance with some embodiments of the present invention.

In some embodiments, the prescription benefits management application may allow the user to select whether group members should pay the price difference between brand name drugs and generic drugs. For example, as shown in FIGS. 22 and 24, when a group member selects a brand prescription when a generic prescription is available, the user may request that the group member be charged for the difference between the brand prescription and the generic prescription. Using screen 2400 of FIG. 24, the user may indicate the type of co-payment/co-insurance to use as the basis for an additional charge on a particular type of claim (e.g., a retail claim, a mail claim, etc.).

Figure 23:
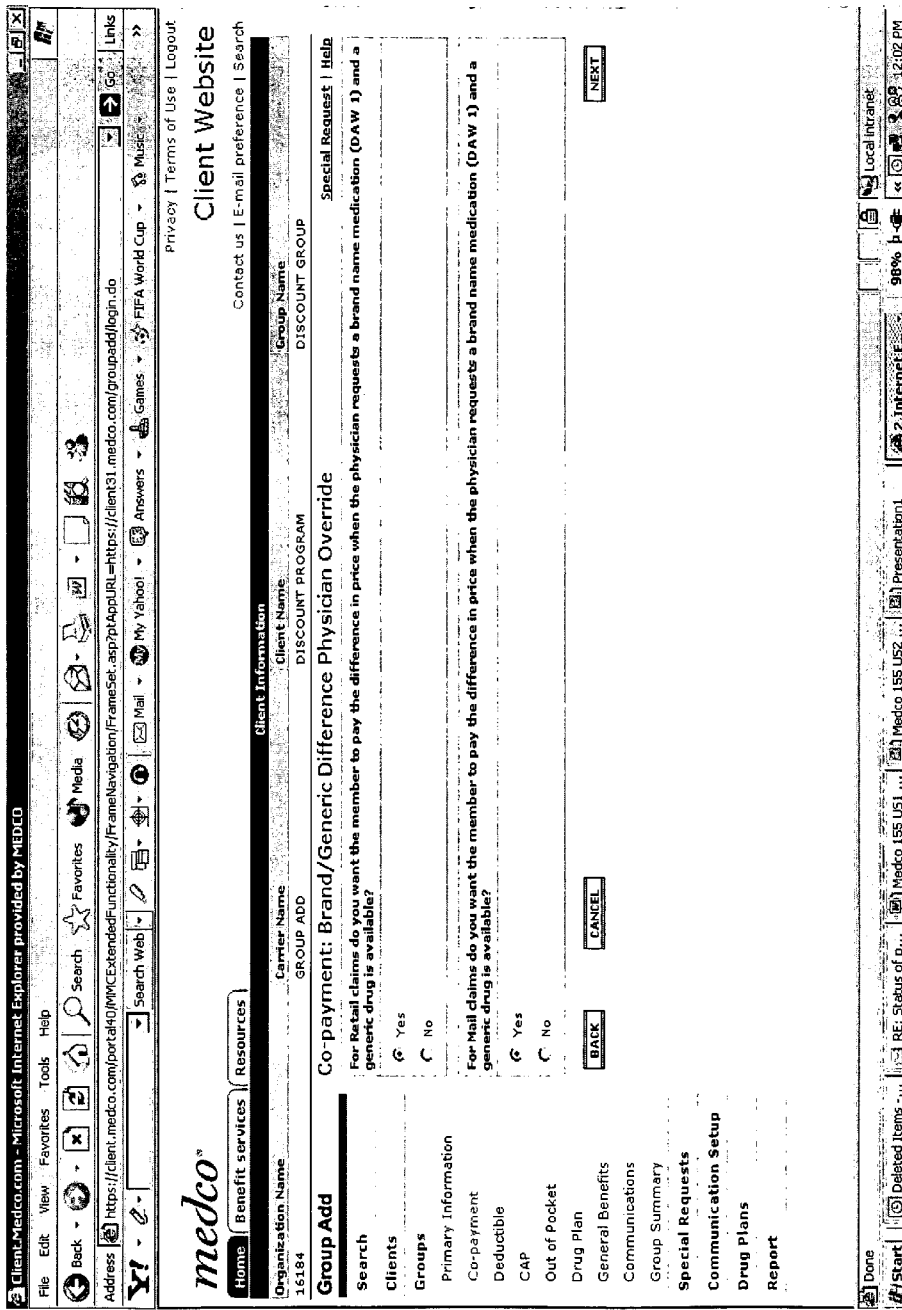

In some embodiments, the prescription benefits management application may allow physicians to override selections made by the user. FIG. 23 shows an illustrative override screen 2300 that allows physicians to make such an override. For example, a physician, using the prescription benefits management application, may override the user's selection that group members should pay the price difference between brand name drugs and generic drugs. In another example, if a pharmacist receives a request to fill a brand prescription and the override option was selected in a member's profile or account, the prescription benefits management application at the pharmacist's workstation (e.g., workstation 102 of FIG. 1) may access the member's profile, determine that the override option was selected, authorize the pharmacist to fill the brand prescription, and automatically print out a label for the brand prescription without charging the group member for the price difference between the brand prescription and the generic prescription. For mail order prescriptions, the prescription benefits management application at the dispensary's workstation may automatically print out a shipping label without charging the group member for the price difference. In yet another example, if a pharmacist receives a request to fill a brand prescription and the override option was not selected in a member's profile or account, the prescription benefits management application at the pharmacist's workstation may access the member's profile, determine that the override option was selected, and prompt the physician to remind the group member that the price difference will be charged should the group member decide to receive the brand prescription as opposed to the generic prescription. For mail order prescriptions, the prescription benefits management application at the dispensary's workstation may transmit an electronic message (e.g., e-mail, text message, etc.) to the group member notifying the group member of the price difference that will be charged.

Figure 25:
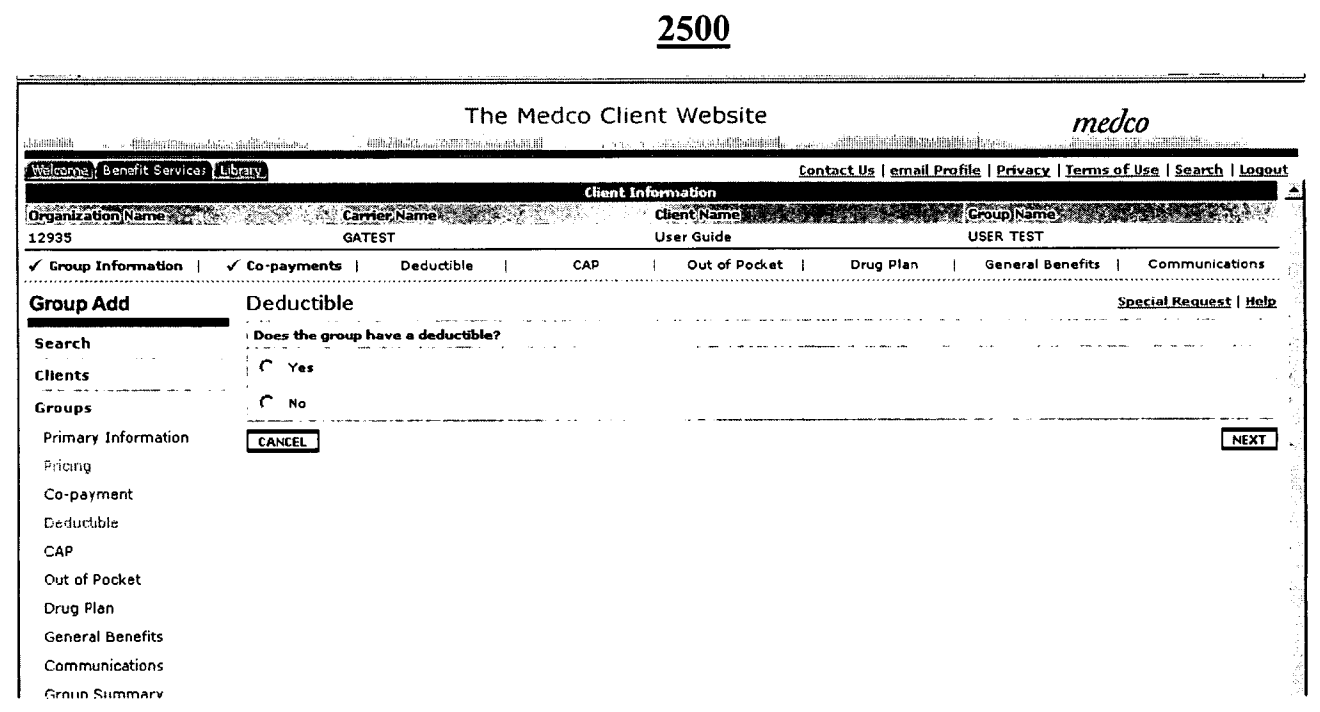
Figure 26:
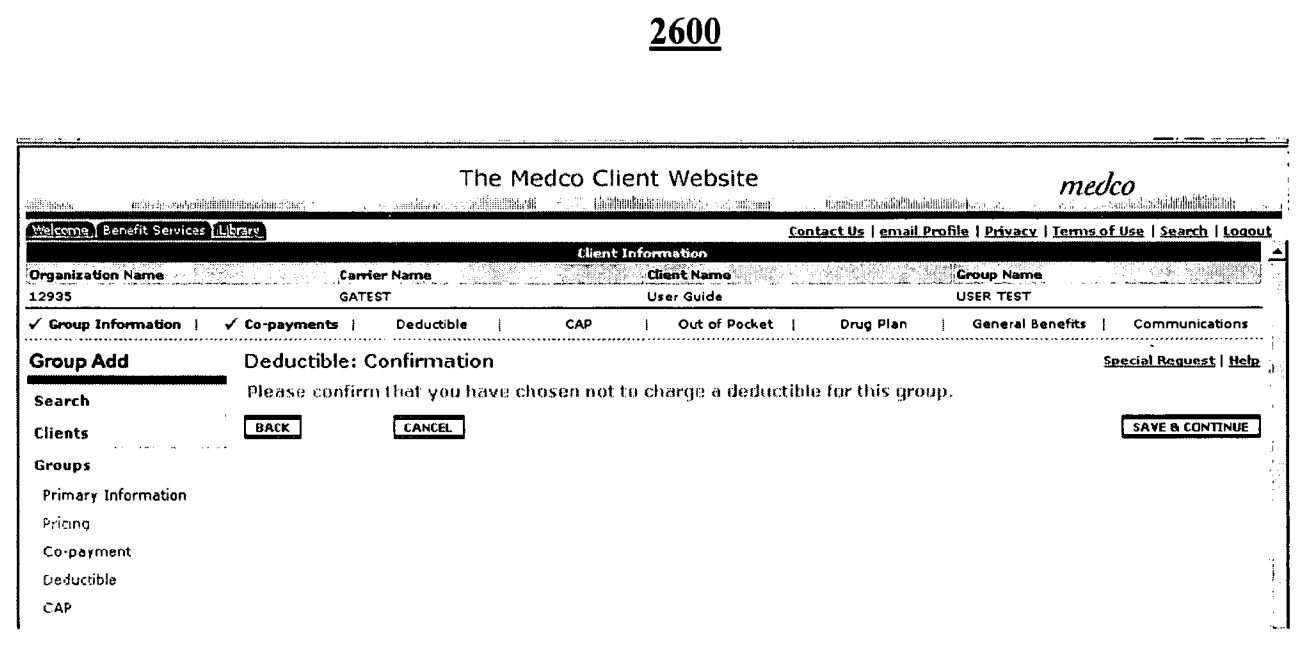
Figure 27:
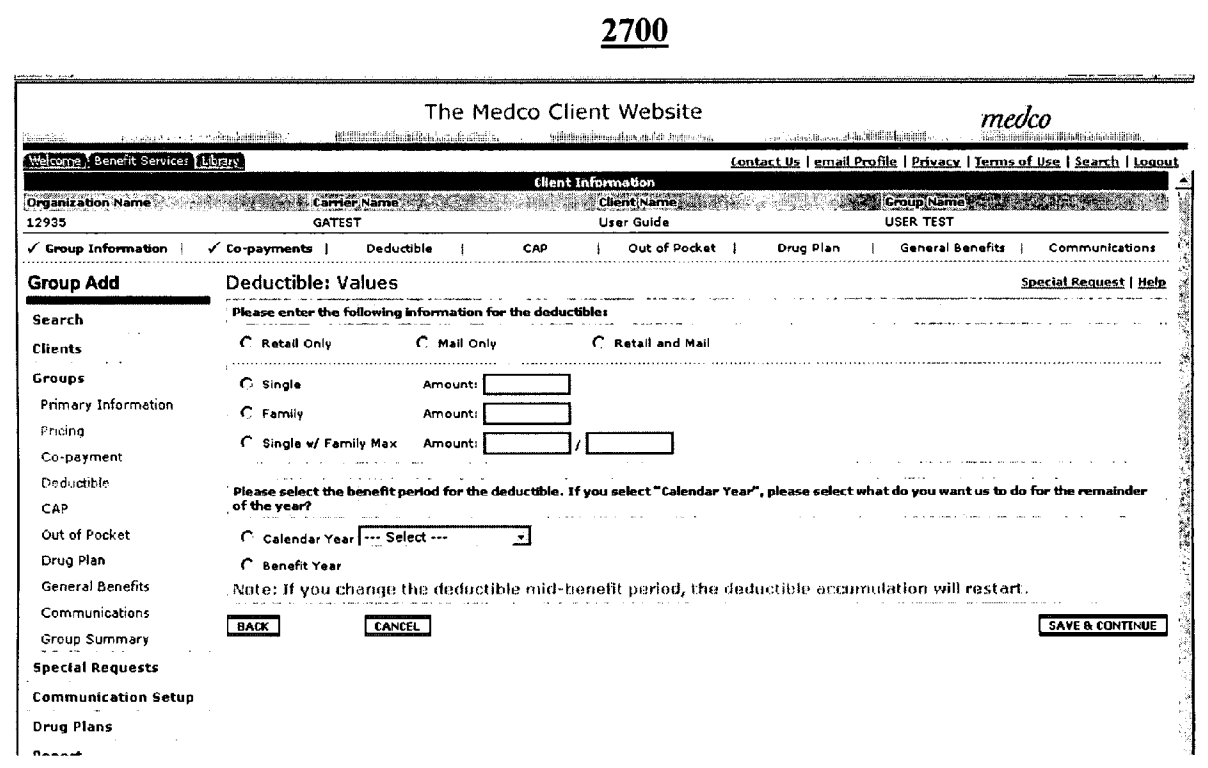

FIGS. 25-27 are illustrative deductible screens that may be provided by the prescription benefits management application in accordance with some embodiments of the present invention. In at least some embodiments, deductibles are cost amounts that a member must reach before their benefits apply. In alternative embodiments, deductibles include, for example, co-pays or any other cost incurred by the members. Prior to reaching a deductible amount (e.g., $500), the member is responsible for the total cost of the claim. In some embodiments, the total cost of the claim may be adjusted by a negotiated client rate. After the deductible is met, the member and the client may share the cost of the claim. For sharing the cost of the claim, the proportion between the member and the client may be predetermine in the benefit plan.

In response to the user indicating that the group does not have a deductible (e.g., by selecting the "No" option and selecting the "Next" button in FIG. 25), the prescription benefits management application may provide the user with a confirmation screen 2600 (FIG. 26). Confirmation screen 2600 may prompt the user to confirm that a deductible is not to be charged to members of this group.

Alternatively, in response to the user indicating that the group does have a deductible (e.g., by selecting the "Yes" option and selecting the "Next" button in FIG. 25), the prescription benefits management application may provide the user with a one or more fields to enter information relating to the deductible for the group. For example, as shown in FIG. 27, the user may indicate the type of claims to apply towards the deductible (e.g., retail claims, mail claims, both retail and mail claims). In addition, the user may select deductible and/or other cost options. Deductible/cost options may include, for example, selecting whether the deductible is to be applied to the individual, family, and/or individual with family CAP (maximum). The deductible options may also allow the user to enter deductible amounts for the selected deductible option. In alternative embodiments, the present invention takes into account benefits banks and/or other types of programs.

In some embodiments, the prescription benefits management application may allow the user to select the benefit period for the deductible. For example, if the user selects "Calendar Year," the prescription benefits management application may prompt the user to waive or charge the deductible for the remainder of the year.

Figure 28:
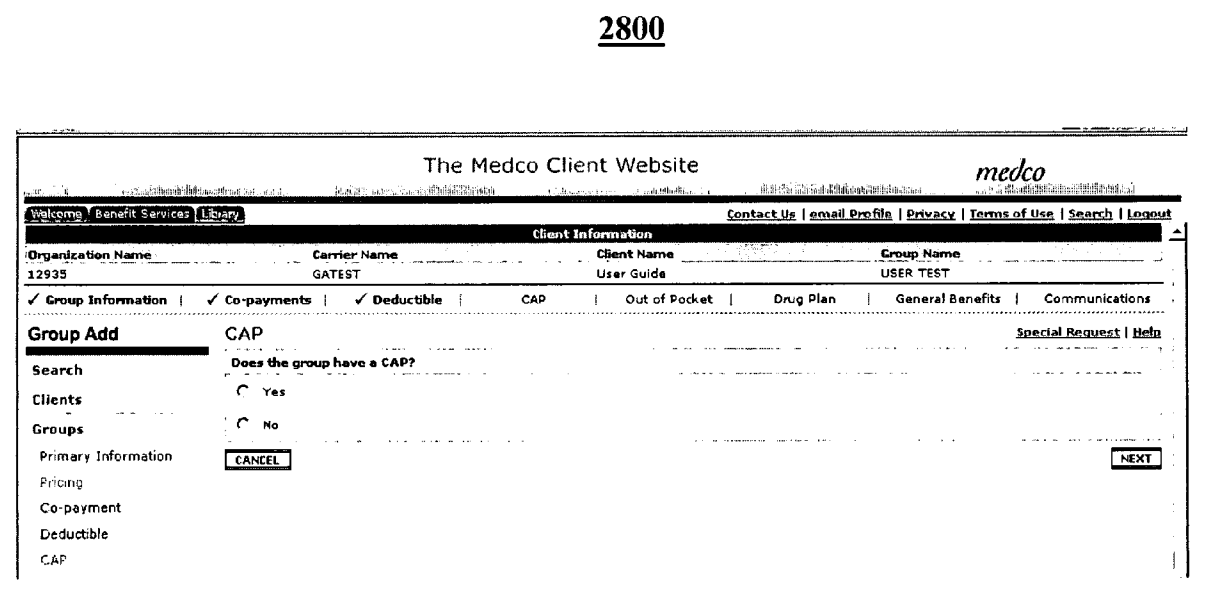
Figure 29:
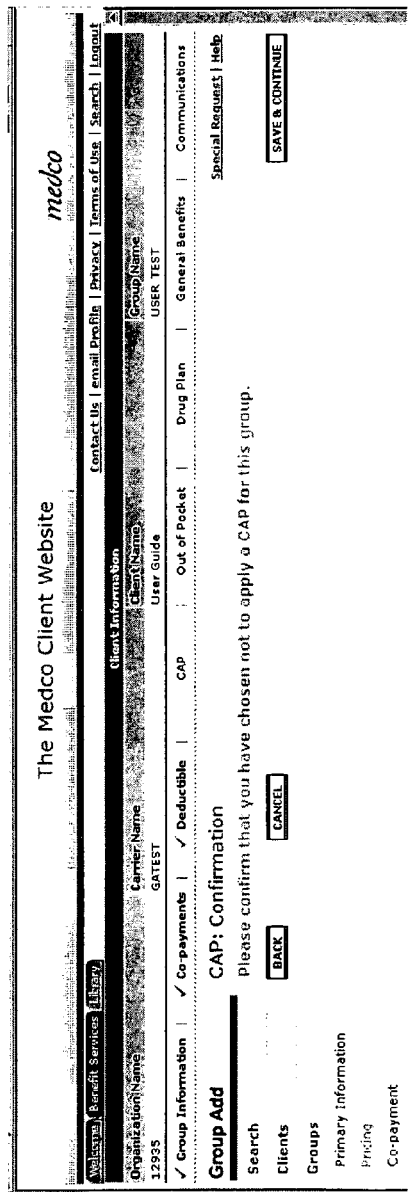
Figure 30:
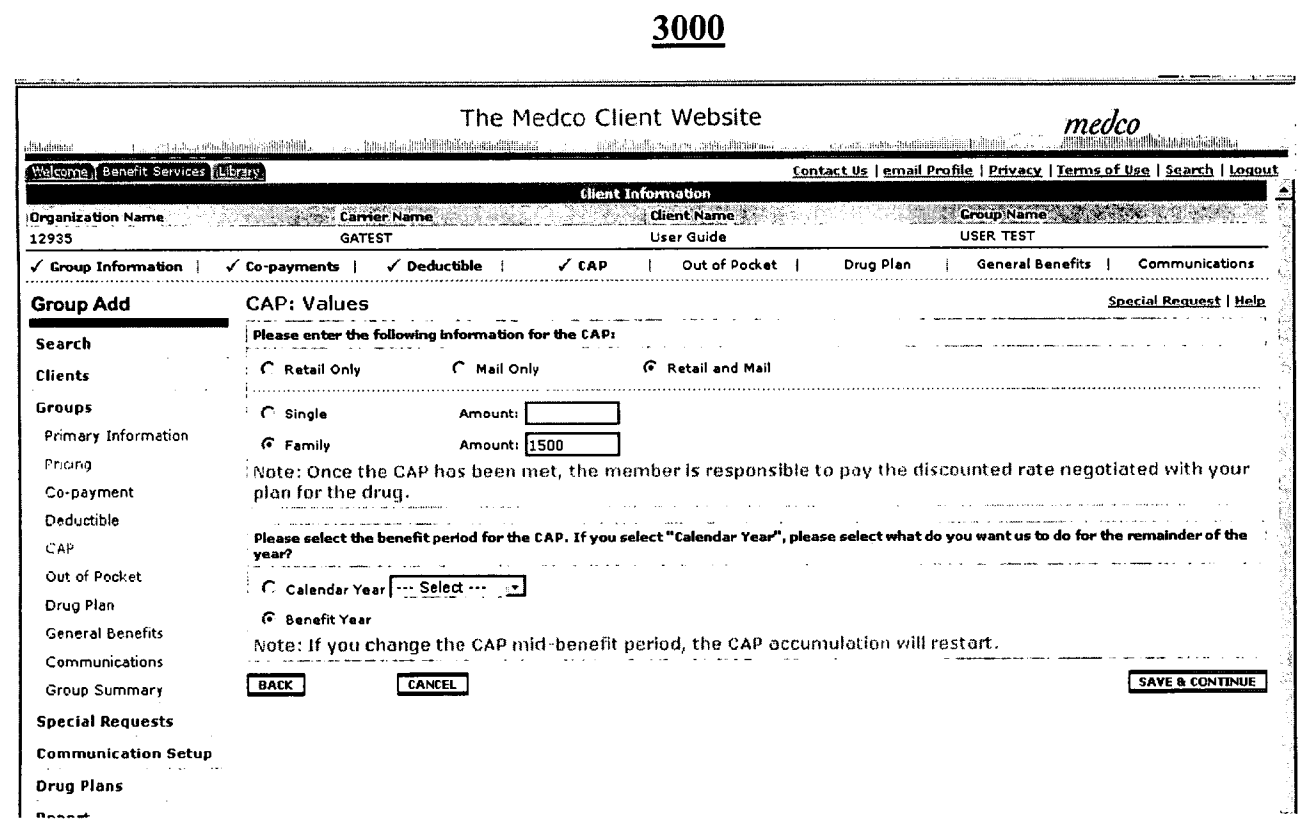

FIGS. 28-30 are illustrative CAP screens that may be provided by the prescription benefits management application in accordance with some embodiments of the present invention. As described previously, a CAP is an approach to limit the benefits allowed to a member or plan participant. The CAP is the maximum benefit allowable by the benefit plan. For example, the CAP may limit the amount a member or family of a member may collect under the benefit plan during a specified period of time.

In response to the user indicating that the group does not have a CAP (e.g., by selecting the "No" option and selecting the "Next" button in FIG. 28), the prescription benefits management application may provide the user with a confirmation screen 2900 (FIG. 29). Confirmation screen 2900 may prompt the user to confirm that a CAP is not to be applied to members of this group.

Alternatively, in response to the user indicating that the group does have a CAP (e.g., by selecting the "Yes" option and selecting the "Next" button in FIG. 28), the prescription benefits management application may provide the user with a one or more fields to enter information relating to the CAP for the group. For example, as shown in FIG. 30, the user may indicate the type of CAP to apply (e.g., retail claims, mail claims, both retail and mail claims). In addition, the user may select CAP options. CAP options may include, for example, selecting whether the CAP is to be applied to the individual, family, and/or individual with family CAP (maximum). The CAP options may also allow the user to enter amounts for the selected CAP (e.g., a $1500 CAP for the family).

In some embodiments, the prescription benefits management application may allow the user to select the benefit period for the CAP. For example, if the user selects "Calendar Year," the prescription benefits management application may prompt the user to indicate a CAP for the remainder of the year.

FIGS. 31-33 are illustrative out-of-pocket (OOP) setup screens that may be provided by the prescription benefits management application in accordance with some embodiments of the present invention. As described previously, an out-of-pocket (OOP) is the maximum amount that a group member or plan participant is required to pay out of the member's own pocket for prescription drugs.

In response to the user indicating that the group does not have an OOP (e.g., by selecting the "No" option and selecting the "Next" button in FIG. 31), the prescription benefits management application may provide the user with a confirmation screen 3200 (FIG. 32). Confirmation screen 3200 may prompt the user to confirm that an OOP is not to be applied to members of this group.

Alternatively, in response to the user indicating that the group does have a deductible (e.g., by selecting the "Yes" option and selecting the "Next" button in FIG. 31), the prescription benefits management application may provide the user with one or more fields to enter information relating to the OOP for the group. For example, as shown in FIG. 33, the user may indicate the type of OOP to apply (e.g., retail claims, mail claims, both retail and mail claims). In addition, the user may select OOP options. OOP options may include, for example, selecting whether the OOP is to be applied to the individual, family, and/or individual with family CAP (maximum). The OOP options may also allow the user to enter amounts for the selected OOP (e.g., $100 out-of-pocket for the family).

In some embodiments, the prescription benefits management application may allow the user to select the benefit period for the OOP. For example, if the user selects "Calendar Year," the prescription benefits management application may prompt the user to indicate a OOP for the remainder of the year.

In some embodiments, the prescription benefits management application may allow the user to customize the drug plan for the new group. FIG. 34 is an illustrative drug plan screen 3400 that may be provided by the prescription benefits management application in accordance with some embodiments of the present invention. As shown in FIG. 34, the prescription benefits management application provides the user with interface elements (e.g., check boxes) to select the supply limit for the drug plan and drug plan coverage options. Using the drug plan coverage options, the user may provide the group members with a customized drug plan tailored to the group members' needs and desires. As shown in FIG. 34, default selections for the drug plan may be pre-selected. However, the prescription benefits management application allows the user to change each option of the drug plan if desired.

For example, if each member negotiates a customized drug plan, pharmacists with access to the prescription benefits management application may review the member's customized drug plan to determine whether a specific drug is covered under the plan. In response to a pharmacist inputting information relating to the requested drug (e.g., the name of the drug, etc.), the prescription benefits management application may automatically access the member's drug plan, determine whether the member's drug plan covers the requested drug, and provides the pharmacist with a notification (e.g., a printed label for the requested drug, a notification that the user is not covered, warning labels for the requested drug, etc.).

In addition to constructing a customized drug plan for the group, the prescription benefits management application may allow the user to setup general benefits for the group. As shown in FIG. 35, the prescription benefits management application provides the user, for example, with options relating to newborn coverage (e.g., a 30-day grace period for newborn dependents under the group member's plan), dependent age limit (e.g., after the dependent reaches the age of 21, the dependent may no longer be covered under the benefit plan), and/or student age limit (e.g., after the student reaches the age of 21, the student may no longer be covered under the benefit plan). As also shown in FIG. 35, each of these options may be divided by distribution channel (e.g., mail order, retail, direct, etc.).

It should be noted that any suitable option may be provided to the user. For example, as shown in FIG. 36, the options provided to the user in setting up general benefits may also include refill override options (e.g., under what circumstances may a pharmacist or benefit administrator allow a refill override), insulin options (e.g., the type of dispensing fee paid on insulin claims), and/or allergy serum options (e.g., whether allergy serum is directly covered by the drug plan). In another example, as shown in FIG. 37, the options provided to the user in setting up general benefits may also include claim processing limitations. The prescription benefits management application may allow the user to select whether the group can process foreign claims.

In some embodiments, the prescription benefits management application generates identification cards for group members. For example, as shown in FIG. 38, the prescription benefits management application provides the user with an illustrative identification card generating screen 3800. Screen 3800 allows the user to select which entity (e.g., the carrier, GATEST, or the benefit administrator, Systemed) is responsible for providing identification cards to the group members.

In response to the user selecting the benefit administrator (e.g., Systemed) and selecting the "Next" button in screen 3800, the prescription benefits management application may provide the user with information relating to the group member in FIG. 39. For example, illustrative identification card screen 3900 may include the RxBin number, card artwork, member instructions, claim forms submission address information, phone number for the benefit provider, webpage address information (e.g., www.medco.com). As shown in screen 3900, a sample identification card (front of the card 3910 and back of the card 3920) is also provided. Once the user is presented with screen 3900, the prescription benefits management application may prompt the user to verify that the information provided on screen 3900 is accurate.

In some embodiments, the prescription benefits management application may allow the user to download a template of the identification card. This allows the user to generate identification cards for each of the group members. Alternatively, the prescription benefits management application may allow the user to use the template to generate temporary identification card. Such a temporary card may be used until the benefit provider provides the group member with a permanent benefit card.

In some embodiments, upon verifying the information provided on screen 3900, the prescription benefits management application may generate a benefit card that is available at the benefit provider's website (e.g., www.medco.com). For example, as shown in FIG. 40, the user may be provided with a notification that a benefit card has been generated and published at the benefit provider's website (e.g., under "Forms & Cards" on the www.medco.com website). In response to downloading and/or printing the benefit card, the group member may use the card at a retail pharmacy for proof of coverage.

As shown in both FIGS. 41-44, the prescription benefits management application may provide the user with communications materials. For example, the user may select which entity (e.g., the benefit provider, the user, the employer, etc.) is responsible for providing member communications. Using illustrative delivery screen 4300 of FIG. 43, the prescription benefits management application allows the user to direct the shipment of the identification cards and/or communications materials. For example, the user may select to bulk ship the identification cards and communication materials to each member of the group. In another example, the user may select to electronically transmit the identification cards and communications materials to each member of the group. It should be noted that any suitable method for transmitting the identification cards and communications materials to the group members and/or the user may be used.

As shown in FIG. 45, when the user has completed entering the information relating to the new group, the prescription benefits management application may automatically generate a group summary screen 4500. Screen 4500 may include, for example, a detailed summary of the previous selections and inputs made by the user (e.g., group name, client name, contract number, general benefits, dependent overage, pricing options, customized drug plan, etc.). Screen 4500 may also request that the user review the information in screen 4500 and confirm the addition of the new group. In response to the user selecting a "Confirm" button (or any other suitable interface element), the prescription benefits management application may provide the user with a confirmation message (e.g., via e-mail, on-screen, etc.).

In response to the user adding a new group, the prescription benefits management application may automatically process the received request and information relating to the new group and update the prescription benefits management application within a predetermined time (e.g., real-time, 24 hours, 48 hours, etc.). For example, a group member under the added group may attempt to fill a prescription at a local pharmacy after the predetermined time. The user (e.g., the employer) or the benefit provider may provide the user with a benefit card and communications materials (e.g., via e-mail). The member may print out the benefit card for use at the local pharmacy. The local pharmacy, using the prescription benefits management application, may access the member's information and determine whether to dispense the requested prescription. In some embodiments, the local pharmacy may access the member's information and dispense the requested prescription without requiring the member to wait until the paperwork associated with the added group has been processed.

For example, a pharmacist or other authorized user may access the member's information using the prescription benefits management application. The prescription benefits management application may allow the pharmacist to input the prescription the member is requesting. In response, the prescription benefits management application may determine whether the prescription is covered under the member's customize drug plan.

In some embodiments, the prescription benefits management application may provide the user with an audit trail (FIG. 46). Using the audit trail, the user may be presented with the activity for the group (e.g., modifications in pricing options, modifications in deductibles, etc.).

When the user is maintaining contracts (e.g., clients), adding a group or a contract, or using any other function or feature of the prescription benefits management application, the user may provide the benefit provider with one or more special requests. As shown in FIG. 47, the prescription benefits management application provides the user with a special request interface screen 4700. Screen 4700 allows the user to transmit requests to the benefit provider.

As shown in FIG. 48, after measuring a given sample of transactions including adding contracts, groups, and group benefits, it was determined that the mean turn-around-time was about 10.632 calendar days. Using the prescription benefits management application, a maximum turn-around-time of 2-3 calendar days is expected.

In at least one embodiment of the present invention, a report utility is provided. In accordance with this embodiment, the user initiates the report request flow by clicking the report button as illustrated in FIG. 49. Next, the user selects Contracts or Groups for the report, enters Start and End Date and clicks SUBMIT, as illustrated in FIG. 50. The user may either open the report on-line or save it (as an Excel file) as illustrated in FIG. 51. FIG. 52 then results with an on-line Report Display. Specifically, the full display, according to at least one embodiment, is illustrated in FIG. 53 listing the following information: carrier number, contract number, group number, flow indicator, confirm date, finalize date, turnaround time, custom drug plan indicator, special request indicator, special request completion date. Examples of the special request field include:

The Group Add application is provides managers, administrators and/or brokers with a quick and easy way to create and maintain contracts and groups. Part of the design of the tool is to hide the complexity of setting up contracts and groups by streamlining the choices that can be made. However, it is inevitable that users want to request benefit options that are not visible in Group Add. Rather than force users to abandon the tool, the Special Request use case allows them to communicate their requirements and still take advantage of the functionality provided by Group Add. The process for handling special requests is a workflow that occurs, for example, outside Group Add, and therefore, outside the 48-hour turnaround time. The special request is communicated to Account Management, who then acts on the request through the appropriate process. Most likely this means making changes to the group or contract in Client Benefit Manager or Modular Copay.

Special requests can be made, for example, while adding or maintaining groups in most sections. Making a special request has an impact on the use case from which it is made. Most likely a special request means that the standard answers to a question in the use case are not an exact fit for the client's needs. Thus, when a special request is made, it suspends the requirement in the calling use case that all questions on the page be answered. The calling use case must add the question(s) that were not answered to the special request. As part of the workflow, Account Management must ensure that the unanswered questions are all covered by the special request. If not, they must follow up with the client, as necessary.

As described hereinabove, the prescription benefits management application of the present invention may allow users to create, edit, and maintain client contracts and/or group benefits.

It is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Although the present invention has been described and illustrated in the foregoing exemplary embodiments, it is understood that the present disclosure has been made only by way of example, and that numerous changes in the details of implementation of the invention may be made without departing from the spirit and scope of the invention, which is limited only by the claims which follow.

What is claimed is:

1. A computer-implemented method for administering prescription drug benefits implemented by a pharmaceutical benefits management computer system, the method comprising at least one of the sequential, non-sequential and sequence independent steps of:
    electronically receiving by the pharmaceutical benefits management computer system a request from a user computing device to access an account for a client administering prescription drug benefits for a plurality of members responsive to a prescription drug plan, wherein the account comprises one or more contracts;
    storing account information in a computer database accessible to the pharmaceutical benefits management computer system;
    in response to receiving the request, electronically transmitting by the pharmaceutical benefits management computer system to the user computing device the account information, wherein the account information comprises information relating to each contract;
    receiving a request from the user computing device to add a new contract associated with the client to the account;
    in response to receiving the request, providing the user computing device with an opportunity to input information relating to the new contract associated with a client, wherein the information relating to the new contract comprises first information relating to prescription benefits and coverage, second information relating to a broker, and third information relating to billing; and
    processing by the pharmaceutical benefits management computer system the information received from the user computing device comprising the first information relating to the prescription benefits and coverage, the second information relating to a broker, and the third information relating to billing;
    transmitting a notification of the inputted information relating to the new contract to a user at a second user computing device; and
    automatically generating by the pharmaceutical benefits management computer system the new contract and generating a contract summary for display on the user computing device.

2. The method of claim 1, further comprising transmitting the information relating to prescription benefits and coverage using the Internet.

3. The method of claim 1, further comprising associating, by at least one of the system and the user computing device, the broker with the new contract.

4. The method of claim 1, further comprising determining where to deliver invoices relating to prescription benefits and coverage.

5. The method of claim 1, further comprising adding one or more groups to the new contract.

6. The method of claim 5, wherein the adding one or more groups to the new contract further comprises adding the one or more groups comprising at least two clients subscribed to the same prescription drug plan.

7. The method of claim 1, further comprising adding one or more benefits to the new contract.

8. A computer-implemented method for allowing a user to manage prescription drug benefits using a pharmaceutical benefits management computer system, the method comprising at least one of the sequential, non-sequential and sequence independent steps of:
    electronically receiving by the pharmaceutical benefits management computer system a request from a user computing device to access an account for a client administering prescription drug benefits for a plurality of members responsive to a prescription drug plan, wherein the account comprises one or more contracts and wherein each contract includes one or more group members;
    storing account information in a computer storage medium accessible to the pharmaceutical benefits management computer system;
    in response to receiving the request, electronically transmitting by the pharmaceutical benefits management computer system to the user computing device the account information, wherein the account information comprises information relating to each contract;
    receiving a request from the user computing device to add a new group member associated with at least one of the contracts or a new contract associated with the client;
    in response to receiving the request, inputting information relating to the group member, wherein the information relating to the group member comprises at least one of information relating to a type of prescription program, pharmacy network, pricing options, co-payments, prescription overrides, deductibles, drug plan, and prescription benefits and coverage;
    transmitting a notification of the inputted information relating to the new group member to a user at a second user computing device; and
    automatically generating a group comprising at least the group member and generating a group summary for display on the user computing device.

9. The method of claim 8, further comprising generating a customized drug plan.

10. The method of claim 8, further comprising determining at least one of a plurality of generic prescription drugs and a plurality of brand prescription drugs to include in a customized drug plan.

11. The method of claim 8, further comprising transmitting the customized drug plan to the group member.

12. The method of claim 8, further comprising transmitting a prescription card to the group member.

13. The method of claim 8, further comprising indicating to the user computing device that a prescription card is available for the group member.

14. The method of claim 8, further comprising allowing a physician to input difference overrides for a user selection related to the characteristics of a prescription drug plan for a member or group.

15. The method of claim 8, further comprising allowing the user at the user computing device to select a pharmacy network for the group member.

16. The method of claim 8, further comprising automatically transmitting a notification to a pharmacist at another user computing device of the addition of the new group member associated with the at least one of contracts or new contract.

17. A computer-implemented method for allowing a user to manage prescription drug benefits using a pharmaceutical benefits management computer system, the method comprising at least one of the sequential, non-sequential and sequence independent steps of:

electronically receiving by the pharmaceutical benefits management computer system a request from a user computing device to access an account for a client administering prescription drug benefits for a plurality of members responsive to a prescription drug plan, wherein the account comprises one or more contracts and wherein each contract includes one or more group members;

storing account information in a computer database accessible to the pharmaceutical benefits management computer system;

in response to receiving the request, electronically transmitting by the pharmaceutical benefits management computer system to the user computing device the account information, wherein the account information comprises information relating to each contract;

receiving a request from the user computing device to add a new contract associated with the client;

in response to receiving the request, providing the user computing device with an opportunity to input information relating to the new contract, wherein the information relating to the new contract comprises first information relating to prescription benefits and coverage, second information relating to a broker, and third information relating to billing;

receiving a request from the user computing device to modify a group member associated with at least one of an existing contract or a new contract;

in response to receiving the request, providing the user computing device with an opportunity to input information relating to the group member, wherein the information relating to the group member comprises information relating to a type of prescription program, a pharmacy network, pricing options, co-payments, prescription overrides, deductibles, drug plan, and prescription benefits and coverage;

automatically transmitting a notification to a pharmacist at another user computing device of the modification to the group member;

receiving a request from the user computing device of the pharmacist to access the contract of the group member;

in response to receiving the request, transmitting the information relating to the group member to the user computing device of the pharmacist;

allowing the pharmacist to fill one or more prescriptions for the group member using the transmitted information; and processing by the pharmaceutical benefits management computer system the information received form the user computing device comprising the first information relating to the prescription benefits and coverage, the second information relating to a the broker, and the third information relating to billing, and automatically generating by the pharmaceutical benefits management computer system the new contract and generating a contract summary for display on the user computing device.

18. The method of claim 17, further comprising adding a plurality of pharmacy networks by the prescription benefits management system in accordance with a user's request, and receiving from the user a selection of a pharmacy network for the group member from the plurality of pharmacy networks responsive to the rules associated with the group.

19. The method of claim 18, further comprising receiving from a physician difference overrides to override a user selection related to the characteristics of a prescription drug plan for a member or group.

20. The method of claim 18, further comprising receiving from the user computing device a selection of a pharmacy network for the group member.

21. The method of claim 17, wherein the transmitting the notification to the pharmacist further comprises transmitting at least one of information regarding a requested drug, a notification of the member's coverage relative to the requested drug or warning information associated with the requested drug.

22. A computer-implemented method for allowing a user to manage prescription drug benefits using a pharmaceutical benefits management computer system for third party prescription benefits administrators, prescription benefits health plans, and prescription benefit broker-direct markets for web-based transmission of prescription benefit and coverage information for at least one of new contracts and groups, the method comprising at least one of the sequential, non-sequential and sequence independent steps of:

electronically receiving by the pharmaceutical benefits management computer system a request from a user computing device to access an account for a client administering prescription drug benefits for a plurality of members responsive to a prescription drug plan, wherein the account comprises one or more contracts and wherein each contract includes one or more group members;

storing account information in a computer accessible to the pharmaceutical benefits management computer system;

in response to receiving the request, electronically transmitting by the pharmaceutical benefits management computer system to the user computing device the account information, wherein the account information comprises information relating to each contract;

receiving a request from the user computing device to add a group member to one of the contracts;

in response to receiving the request, providing the user computing device with an opportunity to input information relating to the group member, wherein the information relating to the group member comprises information relating to a type of prescription program, a pharmacy network, pricing options, co-payments, prescription overrides, deductibles, drug plan, and prescription benefits and coverage;
automatically transmitting a notification to a pharmacist at another user computing device of the modification to the group member;
receiving a request from the user computing device of the pharmacist to access the contract of the group member;
in response to receiving the request, transmitting the information relating to the group member for filling one or more prescriptions for the group member using the transmitted information;
receiving and processing additional requests, including performing the following application functionality:
searching for at least one of contract and group records;
listing contracts;
listing groups;
adding contracts;
adding groups;
adding group benefit choices;
adding group drug plan coverages;
adding group copays;
adding group pricing;
administering contracts;
administering group benefit choices;
administering drug categories;
administering copay;
administering contract and group summary information;
administering on line help information;
administering audit trail information;
terminating the contract;
terminating the group; and
administering user roles supported;
receiving and processing additional requests, including performing the following additional application functionality:
adding and maintaining a client name and primary information;
adding broker involvement and contact information;
determining billing, responsibility to pay the at least one of the prescription benefits manager, the sponsor and the administrator and where to send the invoices;
administering a group name and primary information;
selecting and maintaining program type of prescription coverage, including mail order, retail, and both mail order and retail;
selecting pharmacy network including networks of retail pharmacies contracted by the at least one of the prescription benefits manager, sponsor and administrator;
selecting and determining pricing options including how prescription claims will be priced at point of sale;
setting up and administering member co-payments and co-insurance;
setting up and administering brand and generic difference overrides based on physician DAW;
adding and determining deductible, cost CAP, and Out Of Pocket (OOP) limitations;
selecting and determining Prescription Drug Coverage (Drug Plan) and days supply coverage for program type;
setting up and administering dependent coverage;
setting up and administering general benefits including overrides of specific benefit plan rules at point of sale; and
automatically creating summary documents containing the users' selections for adding a contract, a group, and group benefits.

23. A system for administering prescription drug benefits, using a prescription benefit management system for a plurality of prescription benefit selections offered by at least one prescription benefit provider and administered by at least one prescription benefit administrator performed by at least a user of the prescription benefit administrator, comprising:
a prescription benefits management system for a plurality of prescription benefit selections offered by at least one prescription benefit provider and administered by at least one prescription benefit administrator, storing case records containing information regarding patients and prescription coverage activities for the patient;
a communication device operatively coupled to said prescription benefits management system for providing access to said prescription benefits management system over one or more electronic communication networks; and
a user computing device for accessing said prescription benefits management system from a remote location via said one or more electronic communication networks;
said prescription benefits management system being configured to:
access an account, wherein the account comprises one or more contracts;
in response to receiving the request, providing the user computing device with account information, wherein the account information comprises information relating to each contract;
receiving a request from the user computing device to add a new contract to the account for a client administering prescription drug benefits for a plurality of members responsive to a prescription drug plan;
in response to receiving the request, providing the user computing device with an opportunity to input information relating to the new contract, wherein the information relating to the new contract comprises first information relating to prescription benefits and coverage, second information relating to a broker, and third information relating to billing; and
automatically generating the new contract and generating a contract summary for display on the user computing device.

24. The system of claim 23, wherein said prescription benefits management system transmits the information relating to prescription benefits and coverage using the Internet.

25. The system of claim 23, wherein said prescription benefits management system associates, by at least one of the system and the user computing device, the broker with the new contract.

26. The system of claim 23, wherein said prescription benefits management system determines where to deliver invoices relating to prescription benefits and coverage.

27. The system of claim 23, wherein said prescription benefits management system adds one or more groups to the new contract.

28. The system of claim 23, wherein said prescription benefits management system adds one or more benefits to the new contract.

29. A system for administering prescription drug benefits, using a prescription benefit management system for a plurality of prescription benefit selections offered by at least one prescription benefit provider and administered by at least one prescription benefit administrator performed by at least a user of the prescription benefit administrator, comprising:
a prescription benefits management system for a plurality of prescription benefit selections offered by at least one prescription benefit provider and administered by at least one prescription benefit administrator, storing case records containing information regarding patients and prescription coverage activities for the patient;

a communication device operatively coupled to said prescription benefits management system for providing access to said prescription benefits management system over one or more electronic communication networks; and a user computing device for accessing said prescription benefits management system from a remote location via said one or more electronic communication networks;

said prescription benefits management system being configured to:

receive a request from the user computing device to access an account for a client administering prescription drug benefits for a plurality of members responsive to a prescription drug plan, wherein the account comprises one or more contracts and wherein each contract includes one or more group members;

in response to receiving the request, provide the user computing device with account information, wherein the account information comprises information relating to each contract;

receive a request from the user computing device to add a new contract associated with the client to the account;

receive a request from the user computing device to add a new group member associated with at least one of the contracts or a new contract;

in response to receiving the request, input information relating to the group member, wherein the information relating to the new contract comprises at least one of information relating to a type of prescription program, pharmacy network, pricing options, co-payments, prescription overrides, deductibles, drug plan, and prescription benefits and coverage; and automatically generate a group comprising at least the group member and generating a group summary for display on the user computing device.

30. The system of claim 29, wherein said prescription benefits management system generates a customized drug plan.

31. The system of claim 29, wherein said prescription benefits management system determines at least one of a plurality of generic prescription drugs and a plurality of brand prescription drugs to include in a customized drug plan.

32. The system of claim 29, wherein said prescription benefits management system transmits the customized drug plan to the group member.

33. The system of claim 29, wherein said prescription benefits management system transmits a prescription card to the group member.

34. The system of claim 29, wherein said prescription benefits management system indicates to the user computing device that a prescription card is available for the group member.

35. The system of claim 29, wherein said prescription benefits management system enables a physician to input difference overrides for each drug in a drug plan.

36. The system of claim 29, wherein said prescription benefits management system enables the user at the user computing device to select a pharmacy network for the group member.

37. A system for administering prescription drug benefits, using a prescription benefit management system for a plurality of prescription benefit selections offered by at least one prescription benefit provider and administered by at least one prescription benefit administrator performed by at least a user of the prescription benefit administrator, comprising:

prescription benefits management means for a plurality of prescription benefit selections offered by at least one prescription benefit provider and administered by at least one prescription benefit administrator, storing case records containing information regarding patients and prescription coverage activities for the patient;

communication means for providing access to said prescription benefits management means over one or more electronic communication networks; and user device means for accessing said prescription benefits management means from a remote location via said one or more electronic communication networks;

said prescription benefits management means for:

accessing an account for a client administering prescription drug benefits for a plurality of members responsive to a prescription drug plan, wherein the account comprises one or more contracts;

in response to receiving the request, providing the user device means with account information, wherein the account information comprises information relating to each contract;

receiving a request from the user device means to add a new contract associated with the client to the account;

in response to receiving the request, providing the user device means with an opportunity to input information relating to the new contract, wherein the information relating to the new contract comprises first information relating to prescription benefits and coverage, second information relating to a broker, and third information relating to billing; and automatically generating the new contract and generating a contract summary for display on the user device means.

38. A system for at least one of managing and administering prescription drug benefits, using a prescription benefit management system for a plurality of prescription benefit selections offered by at least one prescription benefit provider and administered by at least one prescription benefit administrator performed by at least a user of the prescription benefit administrator, comprising:

prescription benefits management means for a plurality of prescription benefit selections offered by at least one prescription benefit provider and administered by at least one prescription benefit administrator, storing case records containing information regarding patients and prescription coverage activities for the patient;

communication device means for providing access to said prescription benefits management means over one or more electronic communication networks; and a user device means for accessing said prescription benefits management means from a remote location via said one or more electronic communication networks;

said prescription benefits management means for:

receiving a request from the user device means to access an account for a client administering prescription drug benefits for a plurality of members responsive to a prescription drug plan, wherein the account comprises one or more contracts and wherein each contract includes one or more group members;

in response to receiving the request, providing the user device means with account information, wherein the account information comprises information relating to each contract;

receiving a request from the user device means to add a new group member associated with at least one of the contracts or a new contract associated with the client;

in response to receiving the request, inputting information relating to the group member, wherein the information relating to the group member comprises at least one of information relating to a type of prescription program, pharmacy network, pricing options, co-payments, prescription overrides, deductibles, drug plan, and prescription benefits and coverage; and automatically generating a group comprising at least the group member and generating a group summary for display on the user device means.

* * * * *